US007064248B2

(12) United States Patent
Lundquist et al.

(10) Patent No.: US 7,064,248 B2
(45) Date of Patent: *Jun. 20, 2006

(54) METHOD OF PREPARING FERTILE TRANSGENIC CORN PLANTS BY MICROPROJECTILE BOMBARDMENT

(75) Inventors: Ronald C. Lundquist, Minnetonka, MN (US); David A. Walters, Bloomington, MN (US); Julie A. Kirihara, Bloomington, MN (US)

(73) Assignee: DeKalb Genetics Corp., DeKalb, IL (US)

( * ) Notice: Subject to any disclaimer, the term of this patent is extended or adjusted under 35 U.S.C. 154(b) by 738 days.

This patent is subject to a terminal disclaimer.

(21) Appl. No.: 09/818,921

(22) Filed: Mar. 27, 2001

(65) Prior Publication Data

US 2001/0032344 A1 Oct. 18, 2001

Related U.S. Application Data

(60) Division of application No. 08/619,077, filed on Mar. 20, 1996, now Pat. No. 6,331,665, which is a division of application No. 08/285,488, filed on Aug. 3, 1994, now Pat. No. 5,508,468, which is a continuation of application No. 07/636,089, filed on Dec. 28, 1990, now abandoned, which is a continuation-in-part of application No. 07/508,045, filed on Apr. 11, 1990, now Pat. No. 5,484,956, which is a continuation-in-part of application No. 07/467,983, filed on Jan. 22, 1990, now abandoned, and a continuation-in-part of application No. 08/677,695, filed on Jul. 10, 1996.

(51) Int. Cl.
*A01H 5/00* (2006.01)
*C12N 15/82* (2006.01)

(52) U.S. Cl. ...................................... 800/302; 800/279

(58) Field of Classification Search ................ 800/279, 800/288, 293, 302, 278
See application file for complete search history.

(56) References Cited

U.S. PATENT DOCUMENTS

| | | | | |
|---|---|---|---|---|
| 4,370,160 | A | 1/1983 | Ziemelis | 71/117 |
| 4,399,216 | A | 8/1983 | Axel et al. | 435/6 |
| 4,520,113 | A | 5/1985 | Gallo et al. | 436/504 |
| 4,535,060 | A | 8/1985 | Comai | 435/172.3 |
| 4,536,475 | A | 8/1985 | Anderson | 435/172.3 |
| 4,559,301 | A | 12/1985 | Turner et al. | 435/76 |
| 4,559,302 | A | 12/1985 | Ingolia | 435/172.3 |
| 4,581,847 | A | 4/1986 | Hibberd et al. | 47/58 |
| 4,634,665 | A | 1/1987 | Axel et al. | 435/68 |
| 4,642,411 | A | 2/1987 | Hibberd et al. | 800/1 |
| 4,665,030 | A | 5/1987 | Close | 435/240 |
| 4,666,844 | A | 5/1987 | Cheng | 435/240 |
| 4,683,202 | A | 7/1987 | Mullis | 435/91 |
| 4,708,818 | A | 11/1987 | Montagnier et al. | 435/5 |
| 4,727,028 | A | 2/1988 | Santerre et al. | 435/240.2 |
| 4,743,548 | A | 5/1988 | Crossway et al. | 435/172.3 |
| 4,761,373 | A | 8/1988 | Anderson et al. | 435/172.3 |
| 4,806,483 | A | 2/1989 | Wang | 435/240.49 |
| 4,885,357 | A | 12/1989 | Larkins et al. | 530/373 |
| 4,886,878 | A | 12/1989 | Larkins et al. | 536/26 |
| 4,940,835 | A | 7/1990 | Shah et al. | 800/205 |
| 4,945,050 | A | 7/1990 | Sanford et al. | 435/172.1 |
| 4,956,282 | A | 9/1990 | Goodman et al. | 435/69.51 |
| 4,971,908 | A | 11/1990 | Kishore et al. | 435/172.1 |
| 5,001,060 | A | 3/1991 | Peacock et al. | 435/172.3 |
| 5,004,863 | A | 4/1991 | Umbeck | 800/205 |
| 5,013,658 | A | 5/1991 | Dooner et al. | 435/172.3 |
| 5,015,580 | A | 5/1991 | Christou et al. | 435/172.3 |
| 5,034,322 | A | 7/1991 | Rogers et al. | 435/172.3 |
| 5,036,006 | A | 7/1991 | Sanford et al. | 435/170.1 |
| 5,049,500 | A | 9/1991 | Arnizen et al. | 435/172.3 |
| 5,077,399 | A | 12/1991 | Brauer et al. | 536/27 |
| 5,082,767 | A | 1/1992 | Hatfield et al. | 435/6 |
| 5,094,945 | A | 3/1992 | Comai | 435/172.3 |
| 5,097,093 | A | 3/1992 | Vandeventer et al. | 800/200 |
| 5,110,732 | A | 5/1992 | Benfey et al. | 435/172.3 |
| 5,134,074 | A | 7/1992 | Gordon et al. | 435/240.4 |
| 5,145,777 | A | 9/1992 | Goodman et al. | 435/172.3 |
| 5,164,310 | A | 11/1992 | Smith et al. | 435/172.3 |
| 5,177,010 | A | 1/1993 | Goldman et al. | 435/172.2 |
| 5,187,073 | A | 2/1993 | Goldman et al. | 435/172.3 |
| 5,187,267 | A | 2/1993 | Comai et al. | 536/23.1 |
| 5,188,642 | A | 2/1993 | Shah et al. | 47/58 |
| 5,188,958 | A | 2/1993 | Moloney et al. | 435/240.4 |
| 5,196,342 | A | 3/1993 | Donovan | 435/320.1 |
| 5,215,912 | A | 6/1993 | Hoffman | 435/240.4 |
| 5,231,020 | A | 7/1993 | Jorgensen et al. | 435/172.3 |
| 5,240,841 | A | 8/1993 | Johnston et al. | 435/172.3 |

(Continued)

FOREIGN PATENT DOCUMENTS

AU 80893/87 12/1988

(Continued)

OTHER PUBLICATIONS

Green et al, 1975, Crop Science 15:417-421.*

(Continued)

*Primary Examiner*—Anne Kubelik
(74) *Attorney, Agent, or Firm*—Fulbright & Jaworski, L.L.P.

(57) ABSTRACT

A method of preparing fertile transgenic *Zea mays* (corn) plants which stably express DNA encoding a *Bacillus thuringiensis* endotoxin, so as to impart insect resistance to the fertile transgenic plants is taught. The method comprises bombarding regenerable corn cells with DNA-coated microprojectiles, wherein the DNA is adjusted to be more efficiently expressed in corn than the native *B. thuringiensis sequence*, and regenerating a fertile transgenic plants from the transformed cells.

26 Claims, 8 Drawing Sheets

U.S. PATENT DOCUMENTS

| | | | |
|---|---|---|---|
| 5,250,515 A | 10/1993 | Fuchs et al. | 514/12 |
| 5,254,799 A | 10/1993 | De Greve et al. | 800/205 |
| 5,258,300 A | 11/1993 | Glassman et al. | 435/240 |
| 5,268,463 A | 12/1993 | Jefferson | 536/23.7 |
| 5,272,072 A | 12/1993 | Kaneko et al. | 435/172.3 |
| 5,273,894 A | 12/1993 | Strauch et al. | 435/129 |
| 5,276,268 A | 1/1994 | Strauch et al. | 800/205 |
| 5,278,325 A | 1/1994 | Strop et al. | 554/12 |
| 5,290,924 A | 3/1994 | Last et al. | 536/24.1 |
| 5,302,523 A | 4/1994 | Coffee et al. | 435/172.1 |
| 5,310,667 A | 5/1994 | Eichholtz et al. | 435/172.3 |
| 5,350,689 A | 9/1994 | Shillito et al. | 435/240.47 |
| 5,352,605 A | 10/1994 | Fraley et al. | 435/240.4 |
| 5,367,110 A | 11/1994 | Galili et al. | 800/205 |
| 5,371,003 A | 12/1994 | Murry et al. | 435/172.3 |
| 5,371,015 A | 12/1994 | Sanford et al. | 435/287 |
| 5,380,831 A | 1/1995 | Adang et al. | 536/23.71 |
| 5,384,253 A | 1/1995 | Krzyzek et al. | 435/172.3 |
| 5,405,765 A | 4/1995 | Vasil et al. | 435/172.3 |
| 5,422,254 A | 6/1995 | Londesborough et al. | 435/97 |
| 5,436,389 A | 7/1995 | Pfund | 800/200 |
| 5,436,393 A | 7/1995 | Rocha-Sosa et al. | 800/205 |
| 5,451,513 A | 9/1995 | Maliga et al. | 435/172.3 |
| 5,464,763 A | 11/1995 | Schilperoort et al. | 435/172.3 |
| 5,472,869 A | 12/1995 | Krzyzek et al. | 435/240.4 |
| 5,484,956 A | 1/1996 | Lundquist et al. | 800/205 |
| 5,489,520 A | 2/1996 | Adams et al. | 435/172.3 |
| 5,491,288 A | 2/1996 | Chaubet et al. | 800/205 |
| 5,495,071 A | 2/1996 | Fischhoff et al. | 800/205 |
| 5,500,365 A | 3/1996 | Fischhoff et al. | 435/240.4 |
| 5,508,468 A | 4/1996 | Lundquist et al. | 800/205 |
| 5,516,668 A | 5/1996 | Maruta | 435/172.3 |
| 5,538,877 A | 7/1996 | Lundquist et al. | 435/172.3 |
| 5,538,880 A | 7/1996 | Lundquist et al. | 435/172.3 |
| 5,545,545 A | 8/1996 | Gengenbach et al. | 435/172.3 |
| 5,550,318 A | 8/1996 | Adams et al. | 800/205 |
| 5,554,798 A | 9/1996 | Lundquist et al. | 800/205 |
| 5,559,223 A | 9/1996 | Falco et al. | 536/23.1 |
| 5,561,236 A | 10/1996 | Leemans et al. | 800/205 |
| 5,563,324 A | 10/1996 | Tarczynski et al. | 800/205 |
| 5,565,347 A | 10/1996 | Fillatti et al. | 435/172.3 |
| 5,567,600 A | 10/1996 | Adang et al. | 536/23.71 |
| 5,567,862 A | 10/1996 | Adang et al. | 800/205 |
| 5,576,203 A | 11/1996 | Hoffman | 435/172.3 |
| 5,578,702 A | 11/1996 | Adang | 530/350 |
| 5,580,716 A | 12/1996 | Johnston et al. | 435/5 |
| 5,580,761 A | 12/1996 | Greatbatch et al. | 435/91.32 |
| 5,589,615 A | 12/1996 | De Clercq et al. | 800/205 |
| 5,589,616 A | 12/1996 | Hoffman | 800/205 |
| 5,591,616 A | 1/1997 | Hiei et al. | 435/172.3 |
| 5,593,963 A | 1/1997 | Van Ooijen et al. | 514/12 |
| 5,595,733 A | 1/1997 | Carswell et al. | 424/93.21 |
| 5,596,131 A | 1/1997 | Horn et al. | 800/205 |
| 5,623,067 A | 4/1997 | Vandekerckhove et al. | 361/24.1 |
| 5,625,136 A | 4/1997 | Koziel et al. | 800/205 |
| 5,641,664 A | 6/1997 | D'Halluin et al. | 435/172.3 |
| 5,641,876 A | 6/1997 | McElroy et al. | 536/24.1 |
| 5,677,474 A | 10/1997 | Rogers | 800/205 |
| 5,693,507 A | 12/1997 | Daniell et al. | 435/172.3 |
| 5,743,477 A | 4/1998 | Walsh et al. | 424/94.6 |
| 5,773,691 A | 6/1998 | Falco et al. | 800/205 |
| 5,780,708 A | 7/1998 | Lundquist et al. | 800/205 |
| 5,780,709 A | 7/1998 | Adams et al. | 800/205 |
| 5,886,244 A | 3/1999 | Tomes et al. | 800/293 |
| 5,990,387 A | 11/1999 | Tomes et al. | 800/293 |
| 5,990,390 A | 11/1999 | Lundquist et al. | 800/302 |
| 6,013,863 A | 1/2000 | Lundquist et al. | 800/293 |
| 6,020,539 A | 2/2000 | Goldman et al. | 800/294 |
| 6,025,545 A | 2/2000 | Lundquist et al. | 800/293 |
| 6,258,999 B1 | 7/2001 | Tomes et al. | 800/300.1 |

FOREIGN PATENT DOCUMENTS

| | | |
|---|---|---|
| CA | 2032443 | 6/1991 |
| EP | 0126537 | 11/1984 |
| EP | 0131623 | 1/1985 |
| EP | 0141373 | 5/1985 |
| EP | 0142924 | 5/1985 |
| EP | 0154204 | 9/1985 |
| EP | 0160390 | 11/1985 |
| EP | 0174791 | 3/1986 |
| EP | 0189707 | 8/1986 |
| EP | 0193259 | 9/1986 |
| EP | 0202668 | 11/1986 |
| EP | 0204549 | 12/1986 |
| EP | 0242236 | 10/1987 |
| EP | 0242246 | 10/1987 |
| EP | 0299552 | 1/1988 |
| EP | 0257472 | 3/1988 |
| EP | 0262971 | 4/1988 |
| EP | 0269601 | 6/1988 |
| EP | 0270356 | 6/1988 |
| EP | 0271408 | 6/1988 |
| EP | 0275069 | 7/1988 |
| EP | 0275957 | 7/1988 |
| EP | 0280400 | 8/1988 |
| EP | 0282164 | 9/1988 |
| EP | 0289479 | 11/1988 |
| EP | 0290395 | 11/1988 |
| EP | 0292435 | 11/1988 |
| EP | 0301749 | 2/1989 |
| EP | 0331855 | 9/1989 |
| EP | 0334539 | 9/1989 |
| EP | 0335528 | 10/1989 |
| EP | 0348348 | 12/1989 |
| EP | 0353908 | 2/1990 |
| EP | 0359472 | 3/1990 |
| EP | 0359617 | 3/1990 |
| EP | 0360750 | 3/1990 |
| EP | 0385962 | 9/1990 |
| EP | 0408403 | 1/1991 |
| EP | 0420358 | 4/1991 |
| EP | 0424047 | 4/1991 |
| EP | 0459643 | 5/1991 |
| EP | 0442174 | 8/1991 |
| EP | 0442175 | 8/1991 |
| EP | 0452269 | 11/1991 |
| EP | 0469273 | 2/1992 |
| EP | 0485970 | 5/1992 |
| EP | 0589110 | 3/1994 |
| EP | 0620281 | 10/1994 |
| GB | 2159173 | 11/1985 |
| WO | 85/01856 | 5/1985 |
| WO | 85/02972 | 7/1985 |
| WO | 85/02973 | 7/1985 |
| WO | 86/01536 | 3/1986 |
| WO | 86/03776 | 7/1986 |
| WO | 87/04181 | 7/1987 |
| WO | 87/05629 | 9/1987 |
| WO | 88/08034 | 10/1988 |
| WO | 89/04371 | 5/1989 |
| WO | 89/10396 | 11/1989 |
| WO | 89/11789 | 12/1989 |
| WO | 89/12102 | 12/1989 |
| WO | 90/01551 | 2/1990 |
| WO | 90/01869 | 3/1990 |
| WO | 90/02801 | 3/1990 |
| WO | 90/10691 | 8/1990 |
| WO | 90/10725 | 9/1990 |
| WO | 91/02071 | 2/1991 |
| WO | 91/04270 | 4/1991 |
| WO | 91/04323 | 4/1991 |
| WO | 91/00183 | 5/1991 |
| WO | 91/10725 | 7/1991 |

| | | |
|---|---|---|
| WO | 91/16432 | 10/1991 |
| WO | 92/06205 | 4/1992 |
| WO | 92/09696 | 6/1992 |
| WO | 92/12250 | 7/1992 |
| WO | 92/14822 | 9/1992 |
| WO | 92/17580 | 10/1992 |
| WO | 92/19731 | 11/1992 |
| WO | 93/06220 | 4/1993 |
| WO | 93/07278 | 4/1993 |
| WO | 93/08682 | 5/1993 |
| WO | 93/09237 | 5/1993 |
| WO | 93/14210 | 7/1993 |
| WO | 93/19190 | 9/1993 |
| WO | 93/21335 | 10/1993 |
| WO | 94/08031 | 4/1994 |
| WO | 94/10315 | 5/1994 |
| WO | 94/14970 | 7/1994 |
| WO | 94/20628 | 9/1994 |
| WO | 94/21805 | 9/1994 |
| WO | 95/06128 | 3/1995 |
| WO | 95/13389 | 5/1995 |
| WO | 95/30005 | 11/1995 |
| WO | 96/00789 | 1/1996 |
| WO | 97/22703 | 6/1997 |
| WO | 97/47731 | 12/1997 |

OTHER PUBLICATIONS

Green, 1982, Proc. Fifth Internal. Cong. Plant Tiss. and Cell Cult., pp. 107-108.*
Vasil et al, 1987, Theor. Appl. Genet. 73:793-798.*
Rhodes et al, 1988, BioTechnol. 6:56-60.*
Potrykus, 1990, BioTechnol. 8:535-542.*
Armstrong, C.L., et al., "Genetic and Cytogenetic Variation in Plants Regenerated from Organogenic and Friable, Embryogenic Tissue Cultures in Maize", *Biol. Abstracts, 85*, Abstract No. 117662, p. 22, (1988).
Poehlman, J.M., *In: Breeding Field Crops, 3rd Edition*, AVI Publishing Company, Inc., Westport, CT, p. 452, (1988).
Van den Broeck, G., et al., "Targeting of a Foreign Protein to Chloroplasts by Fusion to the Transit Peptide from the Small Subunit of Ribulose 1,5-biphosphate Carboxylase", *Nature, 313*, 358-363, (Jan. 31, 1985).
U.S. Appl. No. 07/205,155, filed Jun. 10, 1988, Tomes et al.
U.S. Appl. No. 07/392,176, filed Aug. 9, 1989, Adams et al.
U.S. Appl. No. 07/513,298, filed Apr. 17, 1990, Adams et al.
Abbe, E.C., et al., "The Growth of the Shoot Apex in Maize: Embryogeny", *American Journal of Botany, 41*, 285-293, (Apr. 1954).
Abe, K., et al., "Molecular Cloning of a Cysteine Proteinase Inhibitor of Rice (Oryzacystatin)", *The Journal of Biological Chemistry, 262*, 16793-16797, (Dec. 15, 1987).
Adang, M.J., et al., "Characterized Full-Length and Truncated Plasmid Clones of the Crystal Protein of *Bacillus thuringiensis* subsp. *kurstaki* HD-73 and Their Toxicity to *Manduca sexta*", *Gene, 36*, 289-300, (1985).
Adang, M.J., et al., "Expression of a *Bacillus thuringiensis* Insecticidal Crystal Protein Gene in Tobacco Plants", *Molecular Strategies for Crop Protection*, Arntzen, C.J., et al. (eds.), Alan R. Liss, Inc., New York, 345-353, (1987).
Ahokas, H., "Electrophoretic Transfection of Cereal Grains with Exogenous Nucleic Acid", Abstracts, Soc. Biochem. Biophys. Microbio. Fen., Biotieteen Paivat (Bioscience Days), Technical University of Helsinki, Espoo, Finland, p. 2, (1989).
Ahokas, H., "Transfection of Germinating Barley Seed Electrophoretically with Exogenous DNA", *Theor. Appl. Genet., 77*, 469-472, (1989).

Akella, V., et al., "Expression in Cowpea Seedings of Chimeric Transgenes after Electroporation into Seed Derived Embryos", *Plant Cell Rep., 12*, 110-117, (1993).
Al-Feel, W., et al., "Cloning of the Yeast FAS3 Gene and Primary Structure of Yeast Acetyl-CoA Carboxylase", *Proc. Natl. Acad. Sci. USA, 89*, 4534-4538, May (1992).
Altenbach, S.B., et al., "Cloning and Sequence Analysis of a cDNA Encoding a Brazil Nut Protein Exceptionally Rich in Methionine", *Plant Mol. Biol., 8*, 239-250, (1987).
Altenbach, S.B., et al., "Enhancement of the Methionine Content of Seed Proteins by the Expression of a Chimeric Gene Encoding a Methionine-Rich Protein in Transgenic Plants", *Plant Mol. Biol., 13*, 513-522, (1989).
Ampe, C., et al., "The Amino-Acid Sequence of the 2S Sulphur-Rich from Seed of Brazil Nut (*Bertholletia excelsa* H.B.K.)", *Eur. J. Biochem., 159*, 597-604, (1986).
Anderson, J.M., et al., "The Encoded Primary Sequence of a Rice Seed ADP-glucose Pyrophosphorylase Subunit and Its Homology to the Bacterial Enzyme", *The Journal of Biological Chemistry, 264*, 12238-12242, (Jul. 25, 1989).
Anderson, P.C., et al., "Herbicide-Tolerant Mutants of Corn", *Genome, 31*, 994-999, (1989).
Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J., 252*, 199-206, (1988).
Angus, T.A., "Implications of Some Recent Studies of *Bacillus thuringiensis*—A Personal Purview", *Proceedings of the 4th International Colloquium on Insect Pathology*, College Park, MD, 183-189, (Aug. 25-28, 1970).
Armaleo, D., et al., "Biolistic Nuclear Transformation of *Saccharomyces cerevisiae* and Other Fungi", *Curr. Genet., 17*, 97-103, (1990).
Armstrong, C.L., et al., "Development and Availability of Germplasm with High Type II Culture Formation Response", *Maize Genetics Cooperation Newsletter, 65*, 92-93, (Mar. 1, 1991).
Armstrong, C.L., et al., "Establishment and Maintenance of Friable, Embryogenic Maize Callus and the Involvement of L-Proline", *Planta, 164*, 207-214, (1985).
Armstrong, C.L., et al., "Genetic and Cytogenetic Variation in Plants Regenerated from Organogenic and Friable, Embryogenic Tissue Cultures in Maize", *Crop Science, 28*, 363-369, (1988).
Arondel, V., et al., "Map-Based Cloning of a Gene Controlling Omega-3 Fatty Acid Desaturation in Arabidopsis", *Science, 258*, 1353-1355, (Nov. 20, 1992).
Aronson, A.I., et al., "Bacillus thuringiensis and Related Insect Pathogens", *Microbiological Reviews, 50*, 1-24, (Mar. 1986).
Aronson, J.N., et al., "Toxic Trypsin Digest Fragment from the *Bacillus thuringiensis* Parasporal Protein", *Applied and Environmental Microbiology, 53*, 416-421, (Feb. 1987).
Atanassova, R., et al., "A 126 bp Fragment of a Plant Histone Gene Promoter Confers Preferential Expression in Meristems of Transgenic Arabidopsis", *The Plant Journal, 2*, 291-300, (1992).
Aves, K., et al., "Transformation of an Elite Maize Imbred Through Microprojectile Bombardment of Regenerable Embryonic Callus", *In Vitro Cell. Develop Bio., 28A*, Abstract No. P-1134, p. 124A, (1992).
Bagga, S., et al., "Accumulation of 15-kilodalton zein in novel protein bodies in transgenic tobacco", *Plant Physiol.*, vol. 107, pp. 13-23, (1995).

Barker, R.F., et al., "Nucleotide Sequence of the T-DNA Region from the *Agrobacterium tumefaciens* Octopine Ti Plasmid pTi15955", *Plant Mol. Biol. 2*, 335-350, (1983).

Bartels, D., et al., "An ABA and GA Modulated Gene Expressed in the Barley Embryo Encodes and Aldose Reductase Related Protein", *EMBO Journal, 10*, 1037-1043, (May 1991).

Bartley, G.E., et al., "Molecular Cloning and Expression in Photosynthetic Bacteria of a Soybean cDNA Coding for Phytoene Desaturase, an Enzyme of the Carotenoid Biosynthesis Pathway", *Proc. Natl. Acad. Sci. USA, 88*, 6532-6536, (Aug. 1991).

Barton, K.A., et al., "*Bacillus thuringiensis* delta-Endotoxin Expressed in Transgenic *Nicotiana tabacum* Provides Resistance to Lepidopteran Insects", *Plant Physiol., 85*, 1103-1109, (1987).

Barton, K.A., et al., "Production of *Bacillus thuringiensis* Insecticidal Proteins in Plants", *Transgenic Plants, vol. 1*, Kung, S.-D., et al., (eds.), Academic Press, Inc., San Diego, CA, 297-315, (1993).

Beauregard, M., et al., "Design, Expression, and Initial Characterization of MB1, a De Novo Protein Enriched in Essential Amino Acids", *Bio/Technology, 13*, 974-981, (Sep. 1995).

Beerman, F., et al., "Tyrosinase as a Marker for Transgenic Mice", *Nuc. Acids. Res., 19*, 958, (1991).

Belanger, F.C., et al., "Molecular Basis for Allelic Polymorphism of the Maize Globulin-1 Gene", *Genetics, 129*, 863-872, (1991).

Benner, M.S., et al., "Genetic Analysis of Methionine-Rich Storage Protein Accumulation in Maize", *Theor. Appl. Genet., 78*, 761-767, (1989).

Bernasconi, P., et al., "Functional Expression of *Arabidopsis thaliana* Anthranilate Synthase Subunit I in *Escherichia coli*", *Plant Physiol., 106(1),*, 353-358, (1994).

Bevan, M., et al., "A Chimaeric Antibiotic Resistance Gene as a Selectable Marker for Plant Cell Transformation", *Nature, 304*, 184-187, (1983).

Bevan, M., et al., "Structure and Transcription of the Nopaline Synthase Gene Region of T-DNA", *Nuc. Acids Res., 11*, 369-385, (1983).

Binns, A.N., "*Agrobacterium*-Mediated Gene Delivery and the Biology of Host Range Limitations", *Physiologia Plantarum, 79*, 135-139, (1990).

Birk, Y., et al., "Separation of a Tribolium-Protease Inhibitor from Soybeans on a Calcium Phosphate Column", *Biochem. Biophys. Acta, 67*, 326-328, (Feb. 12, 1963).

Bishop, D.H., et al., "Genetically Engineered Viral Insecticides—A Progress Report 1986-1989", *Pestic. Sci., 27*, 173-189, (1989).

Bishop, J.E., "Two Teams Plane Genes into Corn", *The Wall Street Journal*, B1, (Apr. 1990).

Bohlmann, J., et al., "Purification and cDNA cloning of anthranilate synthase from Ruta graveolens: modes of expression and properties of native and recombinant enzymes", *The Plant Journal*, 7 (3), pp. 491-501, (1995).

Bohnert, H.J., "Coping with Water Deficit—Application of Biochemical Principles", 1995 Plant Physiology Meeting, Abstract No. 20003, (1995).

Bohnert, H.J., et al., "Adaptations to Environmental Stresses", *The Plant Cell, 7*, 1099-1111, (1995).

Bol, J.F., et al., "Plant Pathogenesis-Related Proteins Induced by Virus Infection", *Annu. Rev. Phytopathol., 28*, 113-138, (1990).

Booy, G., et al., "Attempted Pollen-Mediated Transformation of Maize", *J. Physiol., 135*, 319-324, (1989).

Botterman, J., et al., "Engineering Herbicide Resistance in Plants", *Trends in Genetics, 4*, 219-222, (Aug. 1988).

Boulton, M.I., et al., "Specificity of *Agrobacterium*-Mediated Delivery of Maize Streak Virus DNA to Members of the Gramineae", *Plant Mol. Biol., 12*, 31-40, (1989).

Bowler, C., et al., "Superoxide Dismutase and Stress Tolerance", *Annu. Rev. Plant Physiol. Plant Mol. Biol., 43*, 83-116, (1992).

Boyer, J.S., "Water Deficits and Photosynthesis", *In: Water Deficits and Plant Growth, vol. IV*, Kozlowski, T.T., (ed.), Academic Press, New York, pp. 153-190, (1976).

Boylan-Pett, W., et al., "Effectiveness of *Bacillus thuringiensis*-Transgenic Potato Plants for Control of Colorado Potato Beetles, 1991", *Insecticides & Acaricide Tests: 1992, 17*, 124-125, (1992).

Boynton, J.E., et al., "Chloroplast Transformation in Chlamydomonas with High Velocity Microprojectiles", *Science, 240*, 1534-1537, (Jun. 10, 1988).

Brignon, P., et al., "Nuclease Sensitivity and Functional Analysis of a Maize Histone H3 Gene Promoter", *Plant Molecular Biology, 22*, 1007-1015, (1993).

Brill, W.J., "Agricultural Microbiology", *Scientific American, 245*, 199-215, (Sep. 1981).

Brunke, K.J., et al., "Insect Control with Genetically Engineered Crops", *Trends in Biotechnology, 9*, 197-200, (1991).

Bryant, J.A., "At Last: Transgenic Cereal Plants from Genetically Engineered Protoplasts", *Trends in Biotechnology, 6*, 291-292, (Dec. 1988).

Buchanan-Wollaston, V., et al., "Detoxification of the Herbicide Dalapon by Transformed Plants", *J. Cell. Biochem., 13D*, Abstract No. M503, p. 330, (1989).

Burgerjon, A., et al., "Industrial and International Standardization of Microbial Pesticides—I. *Bacillus thuringiensis*", *Entomophaga, 22*, 121-129, (1977).

Busvine, J. R., *A Critical Review of the Techniques for Testing Insecticides*, Table of Contents, Commonwealth Agricultural Bureaux, Slough, England, iii-xi, (1971).

Bytebier, B., et al., "T-DNA Organization in Tumor Cultures and Transgenic Plants of the Monocotyledon *Asparagus officinalis*", *Proc. Natl. Acad. Sci. USA, 84*, 5345-5349, (Aug. 1987).

Caimi, P.G., et al., "Cytosolic Expression of the *Bacillus amyloliquefaciens* SacB Protein Inhibits Tissue Development in Transgenic Tobacco and Potato", *New Phytol., 136*, 19-28, (1997).

Caimi, P.G., et al., "Fructan Accumulation and Sucrose Metabolism in Transgenic Maize Endosperm Expressing a *Bacillus amyloliquefaciens* SacB Gene", *Plant Physiol., 110*, 355-363, (1996).

Calabrese, D.M., et al., "A Comparison of Protein Crystal Subunit Sizes in *Bacillus thuringiensis*", *Canadian Journal of Microbiology, 26*, 1006-1010, (Aug. 1980).

Caligiuri, M.G., et al., "Identification of Amino Acid Residues Involved in Feedback Regulation of the Anthranilate Synthase Complex from *Salmonella typhimurium*", *J. Biol. Chem., 266*, 8328-8335, (May 5, 1991).

Callis, J., et al., "Introns Increase Gene Expression in Cultured Maize Cells", *Genes and Development, 1*, 1183-1200, (1987).

Cao, J., et al., "Transformation of Rice and Maize Using the Biolistic Process", *In: Plant Gene Transfer*, Lamb, C.J., et al., (eds.), Wiley-Liss, Inc., New York, pp. 21-33, (1990).

Caplan, A., et al., "Introduction of Genetic Material into Plant Cells", *Science, 222*, 815-821, (Nov. 18, 1983).

Carozzi, N.B., et al., "Expression of a Chimeric CaMV 35S *Bacillus thuringiensis* Insecticidal Protein Gene in Transgenic Tobacoo", *Plant Molecular Biology, 20*, 539-548, (1992).

Carpita, N.C., "The Biochemistry of "Growing" Cell Walls", *In: Physiology of Cell Expansion During Plant Growth*, Cosgrove, D.J. et al, (eds.), Am. Soc. Plant Physiol., pp. 28-100, (1987).

Casas, A.M., et al., "Transgenic Sorghum Plants via Microprojectile Bombardment", *Proc. Natl. Acad. Sci. USA, 90*, 11212-11216, (Dec. 1993).

Castillo, A.M., et al., "Rapid Production of Fertile Transgenic Plants of Rye (*Secale cereale* L.)", *Bio/technology, 12*, 1366-1371, (Dec. 1994).

Chaleff, R.S., "Induction, Maintenance, and Differentiation of Rice Callus Cultures on Ammonium as Sole Nitrogen Source", *Plant Cell Tissue Organ Culture, 2*, 29-37, (1983).

Chan, M., et al., "*Agrobacterium*-Mediated Production of Transgenic Rice Plants Expressing a Chimeric a-Amylase Promoter/B-Glucuronidase Gene", *Plant Mol. Biol., 22*, 491-506, (1993).

Chandler, V.L., et al., "Two Regulatory Genes of the Maize Anthocyanin Pathway are Homologous: Isolation of B Utilizing R Genomic Sequences", *The Plant Cell, 1*, 1175-1183, (1989).

Charest, P.J., et al., "Factors Affecting the Use of Chloramphenicol Acetyltransferase as a Marker for Brassica Genetic Transformation", *Plant Cell Reports, 7*, 628-631, (1989).

Chasan, R., "Transforming Maize Transformation", *The Plant Cell, 4*, 1463-1464, (1992).

Chourey, P.S., et al., "Callus Formation from Protoplasts of a Maize Cell Culture", *Theor. Appl. Genet., 59*, 341-344, (1981).

Christou, P., et al., "Cotransformation Frequencies of Foreign Genes in Soybean Cell Cultures", *Theor. Appl. Genet., 79*, 337-341, (1990).

Christou, P., et al., "Genetic Transformation of Crop Plants Using Microprojectile Bombardment", *The Plant Journal, 2*, 275-281, (1992).

Christou, P., et al., "Inheritance and Expression of Foreign Genes in Transgenic Soybean Plants", *Proc. Natl. Acad. Sci. USA, 86*, 7500-7504, (Oct. 1989).

Christou, P., et al., "Opine Synthesis in Wild-Type Plant Tissue", *Plant Physiol., 82*, 218-221, (1986).

Christou, P., et al., "Production of Transgenic Rice (*Oryza sativa* L.) Plants from Agronomically Important Indica and Japonica Varieties via Electric Discharge Particle Acceleration of Exogenous DNA into Immature Zygotic Embryos", *Bio/technology, 9*, 957-962, (Oct. 1991).

Christou, P., et al., "Soybean Genetic Engineering—Commercial Production of Transgenic Plants", *Trends in Biotechnology, 8*, 145-151, (1990).

Christou, P., et al., "Stable Transformation of Soybean Callus by DNA-Coated Gold Particles", *Plant Physiol., 87*, 671-674, (1988).

Chu, C., et al., "Establishment of an Efficient Medium for Another Culture of Rice Through Comparative Experiments on the Nitrogen Sources", *Scientia Sinica, 18*, 659-668, (Sep.-Oct. 1975).

Chui, C., et al., "A new methionine-rich seed storage protein from maize", *Plant Physiol.*, vol. 107, p. 291, (1995).

Clark, B., "Biotech Advance in Corn: Gunslinging Reasearchers Fire Marker Genes in to Corn", *AG Consultant, 46*, 12, (Jul. 1990).

Clemente, T.E., et al., "The Components of Variation Associated with *Agrobacterium*-Mediated Transformation of Soybean", *In Vitro Cellular and Developmental Biology, 31*, Abstract No. W-20, 28A, (Mar. 1995).

Cocking, F., et al., "Gene Transfer in Cereals", *Science, 236*, 1259-1262, (1987).

Coe, E., et al., "The Genetics of Corn", *In: Corn and Corn Improvement, Third Edition*, Sprague, G.F., et al., (eds.), American Society of Agronomy, Inc., Madison, WI, 81-258, (1988).

Comai, L., et al., "Expression in Plants of a Mutant aroA Gene from *Salmonella typhimurium* Confers Tolerance to Glyphosate", *Nature, 317*, 741-744, (Oct. 1985).

Cooksey, K.E., "Purification of a Protein from *Bacillus thuringiensis* Toxic to Larvae of Lepidoptera", *Biochem. J., 106*, 445-454, (1968).

Creissen, G., et al., "*Agrobacterium*- and Microprojectile-Mediated Viral DNA Delivery into Barley Microspore-Derived Cultures", *Plant Cell Reports, 8*, 680-683, (Apr. 1990).

Crossway, A., et al., "Integration of Foreign DNA Following Microinjection of Tobacco Mesophyll Protoplasts", *Mol. Gen. Genet., 202*, 179-185, (1986).

D'Halluin, K., et al., "Transgenic Maize Plants by Tissue Electroporation", *The Plant Cell, 4*, 1495-1505, (Dec. 1992).

Darvill, A., et al., "The Primary Cell Walls of Flowering Plants", *In: The Plant Cell*, vol. 1 of "The Biochemistry of Plants" Series, Tolbert, N.E., (ed.), Academic Press, New York, pp. 91-162, (1980).

Datta, S.K., et al., "Genetically Engineered Fertile Indica-Rice Recovered from Protoplasts", *Bio/Technology, 8*, 736-740, (Aug. 1990).

Dauce-Le Reverend, B., et al., "Improvement of *Escherichia coli* Strains Overproducing Lysine Using Recombinant DNA Techniques", *European J. Appl. Microbiol. Biotechnol., 15*, 227-231, (1982).

De Block, M., et al., "Engineering Herbicide Resistance on Plants by Expression of a Detoxifying Enzyme", *EMBO J., 6*, 2513-2518, (1987).

De Block, M., et al., "Expression of Foreign Genes in Regenerated Plants and Their Progeny", *EMBO J., 3*, 1681-1689, (1984).

De Block, M., et al., "The Use of Phosphinothricin Resistance as a Selectable Marker in Tobacco Protoplast Transformation", *In: Progress in Plant Protoplast Research*, Proceedings of the 7th International Protoplast Symposium, Wageningen, The Netherlands, Puite, K.J., et al., (eds.), Kluwer Academic Publishers, Dordrecht, 389-390, (Dec. 6-11, 1987).

De Greef, W., et al., "Evaluation of Herbicide Resistance in Transgenic Crops under Field Conditions", *Bio/Technology, 7*, 61-64, (1989).

Dekeyser, R.A., et al., "Evaluation of Selectable Markers for Rice Transformation", *Plant Physiol., 90*, 217-223, (1989).

Dekeyser, R.A., et al., "Transient Gene Expression in Intact and Organized Rice Tissues", *The Plant Cell, 2*, 591-602, (Jul. 1990).

Denecke, J., et al., "Quantification of Transient Expression Levels of Genes Transferred to Plant Protoplasts by Electroporation", *Progress in Plant Protoplast Research*, Puite, K.J., et al., (eds.), Proceedings of the 7th International Protoplast Symposium, Wageningen, The Netherlands, 337-338, (Dec. 6-11, 1987).

Denholm, I., et al., "Tactics for Managing Pesticide Resistance in Arthropods: Theory and Practice", *Annu. Rev. Entomol., 37*, 91-112, (1992).

Depicker, A.G., et al., "A Negative Selection Scheme for Tobacco Protoplast-Derived Cells Expressing the T-DNA Gene 2", *Plant Cell Reports, 7*, 63-66, (1988).

DeWald, S.G., et al., "Plant Regeneration from Inbred Maize Suspensions", *Abstracts, VII International Congress on Plant Tissue and Cell Culture*, Amsterdam, The Netherlands, Abstract No. A1-36, p. 12, (Jun. 24-29, 1990).

DeWet, J.J., et al., "Exogenous Gene Transfer in Maize (*Zea mays*) using DNA-treated Pollen", *In: The Experimental Manipulation of Ovule Tissues*, Chapman, G.P., et al., (eds.), Longman, New York, pp. 197-209, (1985).

DeWet, J.R., et al., "Cloning of Firefly Luciferase cDNA and the Expression of Active Luciferase in *Escherichia coli*", *Proc. Nat. Acad. Sci. USA, 82*, 7870-7873, (1985).

Di, R., et al., "Transformation of Soybean with Bean Pod Mottle Virus Coat Proteins-Precursor Gene using the Biolistic Method", *Phytopathology, 83*, Abstract No. A394, p. 1374, (Dec. 1993).

Domoney, C., et al., "Cloning and Characterization of Complementary DNA for Convicilin, a Major Seed Storage Protein in *Pisum sativum* L.", *Planta, 159*, 446-453, (1983).

Donn, G., et al., "Stable Transformation of Maize with a Chimaeric, Modified Phosphinothricin-Acetyltransferase Gene from *Streptomyces viridochromogenes*", *Abstracts, VIIth International Congress on Plant Tissue Cell Culture*, Amsterdam, The Netherlands, Abstract No. A2-38, p. 53, (Jun. 24-29, 1990).

Droge-Laser, W., et al., "The Metabolites of the Herbicide L-Phosphinothricin (Glufosinate)", *Plant Physiol., 105*, 159-166, (1994).

Duncan, D.R., et al., "The Production of Callus Capable of Plant Regeneration for Immature Embryos of Numerous *Zea mays* Genotypes", *Plants, 165*, 322-332, (1985).

Dunder, E., et al., "High Frequency Transformation of Maize by Microprojectile Bombardment of Immature Embryos", *Abstracts, 35 Annual Maize Genetics Conference*, St. Charles, IL, Poster No. 16, p. 30, (Mar. 18-21, 1993).

Dunder, E., et al., "Transgenic Anthocyanin Color Phenotypes Produced in Callus, Plants and Progeny of Maize", *Abstracts, 35th Annual Maize Genetics Conference*, St. Charles, IL, Poster No. 15, p. 30, (Mar. 18-21, 1993).

Dunleavy, J.M., "*Curtobacterium plantarum* sp. nov. Is Ubiquitous in Plant Leaves and Is Seed Transmitted in Soybean and Corn", *International Journal of Systematic Bacteriology, 39*, 240-249, (Jul. 1989).

Dunn, G.M., et al., "Inheritance of Cyclic Hydroxamates in *Zea mays* L.", *Can. J. Plant Sci., 61*, 583-593, (Jul. 1981).

Dupuis, I., et al., "Gene Transfer to Maize Male Reproductive Structure by Particle Bombardment of Tassel Primordia", *Plant Cell Rep., 12*, 607, (1993).

Dure III, L., et al., "Common Amino Acid Sequence Domains Among the LEA Proteins of Higher Plants", *Plant Molecular Biology, 12*, 475-486, (1989).

Dybvig, K., et al., "Transposition of Gram-Positive Transposon Tn916 in *Acholeplasma laidlawii* and *Mycoplasma pulmonis*", *Science, 235*, 1392-1394, (Mar. 13, 1987).

Edallo, S., et al., "Chromosomal Variation and Frequency of Spontaneous Mutation Associated with in vitro Culture and Plant Regeneration in Maize", *Maydica, 26*, 39-56, (1981).

Ellis, J.G., et al., "Does the OCS-Element Occur as a Functional Component of the Promotors of Plant Genes", *The Plant Journal, 4*, 433-443, (1993).

Evans, D.A., et al., "Somaclonal Variation—Genetic Basis and Breeding Applications", *Trends Genet., 5*, 46-50, (1989).

Falco, S.C., et al., "Transgenic Canola and Soybean Seeds with Increased Lysine", *Bio/Technology, 13*, 577-582, (Jun. 1995).

Fast, P.G., et al., "*Bacillus thuringiensis* delta-Endotoxin: Evidence that Toxin Acts at the Surface of Susceptible Cells", *Experientia, 34*, 762-763, (1978).

Faust, R.M., et al., "Bacteria and Their Toxins as Insecticides", *In: Microbial and Viral Pesticides*, Kurstak, E., (ed.), Marcel Dekker, Inc., New York, 75-208, (1982).

Fennel, A., et al., "Electroporation and PEG Delivery of DNA into Maize Microspores", *Plant Cell Reports, 11*, 567-570, (1992).

Finkle, B.J., et al., "Growth and Regeneration of Alfalfa Callus Lines After Freezing in Liquid Nitrogen", *Plant Science, 42*, 133-140, (1985).

Finnegan, J., et al., "Transgene Inactivation: Plants Fight Back!", *Bio/Technol., 12*, 883-888, (Sep. 1994).

Finney, D.J., *In: Probit Analysis: A Statistical Treatment of the Sigmoid Response Curve*, Table of Contents, 3 p., (1952).

Fischhoff, D.A., et al., "Insect Tolerant Transgenic Tomato Plants", *Bio/technology, 5*, 807-812, (1987).

Fisher, D.K., et al., "Starch Branching Enzyme II from Maize Endosperm", *Plant Physiol., 102*, 1045-1046, (1993).

Fitzpatrick, T., "Pleiotrophic Gene Found in Barley Plant", *Genetic Engineering News, 13*, 1, (1993).

Flavell, R., et al., "Prospects for Transforming Monocot Crop Plants", *Nature, 307*, 108-109, (Jan. 12, 1984).

Follansbee, E., et al., "Transformation of *Euphorbia lathyris* by *Agrobacterium rhizogenes*", *In Vitro Cellular and Developmental Biology*, Program Issue, Congress on In Vitro Biology, Abstract No. P-1093, 72A, (May 20-24, 1995).

Frame, B.R., et al., "Production of Fertile Transgenic Maize Plants by Silicon Carbide Whisker-Mediated Transformation", *The Plant Journal, 6*, 941-948, (1994).

Fransz, P., et al., "Cytodifferentiation During Callus Initiation and Somatic Embryogenesis in *Zea mays* L.", Ph.D. Thesis, University of Wageningen Press, The Netherlands, (1988).

Freeling, J.C., et al., "Developmental Potentials of Maize Tissue Cultures", *Maydica, XXI*, 97-112 (Jul. 1977).

Freiberg, B., "More Researchers Discover Corn Transformation Technology", *AG Biotechnology News*, p. 26, (1990).

Fromm, M., et al., "Transient Expression and Stable Transformation of Maize Using Microprojectiles", *In: Plant Molecular Biology, vol. 2*, Hermann, R.G., et al., (eds.), Plenum Press, New York, 219, (1991).

Fromm, M.E., et al., "Expression of Genes Transfected into Monocot and Dicot Plant Cells by Electroporation", *Proc. Nat. Acad. Sci. USA, 82*, 5824-5828, (1985).

Fromm, M.E., et al., "Inheritance and Expression of Chimeric Genes in the Progeny of Transgenic Maize Plants", *Bio/Technology, 8*, 833-839, (1990).

Fromm, M.E., et al., "Stable Transformation of Maize after Gene Transfer by Electroporation", *Nature, 319*, 791-793, (1986).

Fry, S.C., "Introduction to the Growing Cell Wall", *In: The Growing Plant Cell Wall: Chemical and Metabolic Analysis*, Longman Scientific and Technical, New York, pp. 1-5, 102-109, (1988).

Fukuto, T.R., "Physicochemical Aspects of Insecticidal Action", *In: Insecticidal Biochemistry and Physiology*, Wilkinson, C.F., (ed.), Plenum Press, New York, 397-428, (1976).

Gallagher, S., "Progress and Promise of the Particle Gun", *Ag Biotechnology News, 6*, 12-13, (Mar.-Apr. 1989).

Gallie, D.R., et al., "The 5'-leader Sequence of Tobacco Mosaic Virus RNA Enhances the Expression of Foreign Gene Transcripts In Vitro and in Vivo", *Nucleic Acids Research, 15*, 3257-3273, (1987).

Gatehouse, A.M., et al., "Assessment of the Antimetabolic Effects of Trypsin Inhibitors from Cowpea (*Vigna unguiculata*) and Other Legumes on Development of the Bruchid Beetle *Callosobruchus maculatus*", *J. Sci. Food Agric., 34*, 345-350, (1983).

Geiser, M., et al., "The Hypervariable Region on the Genes Coding for Entomophatogenic Crystal Proteins of *Bacillus thuringiensis*: Nucleotide Sequence of the kurhd1 gene of subsp. *kurstaki* HD1", *Gene, 48*, 109-118, (1986).

Genovesi, A.D., et al., "Embryogenesis in Callus Derived from Rice Microspores", *Plant Cell Reports, 1*, 257-260, (1982).

Georghiou, G.P., et al., "Factors Influencing the Evolution of Resistance", *In: Pesticide Resistance: Strategies and Tactics for Management*, Committee on Strategies for the Management of Pesticide Resistant Pest Populations, Board on Agriculture, National Research Council, National Academy Press, Washington, D.C., 157-169, (1986).

Gepts, P., et al., "Enhanced Available Methionine Concentration Associated with Higher Phaseolin Levels in Common Bean Seeds", *Theor. Appl. Genet., 69*, 47-53, (1984).

Gerlach, W.L., "Genetic Engineering: Its Place in Plant Breeding", *In: Plant Breeding and Genetic Engineering*, Zakri, A.H., (ed.), Society for the Advancement of Breeding Researches in Asia and Oceania, Bangi, Malaysia, 269-277, (1988).

Goff, S.A., et al., "Transactivation of Anthocyanin Biosynthetic Genes Following Transfer of B Regulatory Genes into Maize Tissues", *EMBO Journal, 9*, 2517-2522, (1990).

Goldburg, R.J., et al., "Are B.T.K. Plants Really Safe to Eat?", *Bio/technology, 8*, 1011-1015, (Nov. 1990).

Goldfarb, B. et al., "Transient Expression of Microprojectile-Introduced DNA in Douglas-Fir", *J. Cell. Biochem.*, Suppl. 0 (13 Part D), Abstract No. M 121, p. 259, (Apr. 1-7, 1989).

Goldman, S.L., et al., "Transformation of *Zea mays* by *Agrobacterium tumefaciens*: Evidence for Stable Genetic Alterations", *Journal of Cellular Biochemistry, 11B*, Abstract No. F 202, p. 26, (1987).

Goodman, R.M., et al., "Gene Transfer in Crop Improvement", *Science, 236*, 48-54, (Apr. 3, 1987).

Gordon, P.N., et al., "Plant Regeneration from Tissue Cultures of Maize", *Maize Genetics Cooperation Newsletter, 51*, 79-80, (Mar. 1, 1977).

Gordon-Kamm, W.J., et al., "Stable Transformation of Embryonic Maize Cultures by Microprojectile Bombardment", *J. Cellular Biochem., 13D*, Abstract No. M122, p. 259, (1989).

Gordon-Kamm, W.J., et al., "Transformation of Maize Cells and Regeneration of Fertile Transgenic Plants", *The Plant Cell, 2*, 603-618, (Jul. 1990).

Gordon-Kamm, W.J., et al., "Transformation of Maize Using Microprojectile Bombardment: An Update and Perspective", *In Vitro Cellular and Developmental Biology, 27*, 21-27, (Jan. 1991).

Gould, J. et al., "Shoot Tip Culture as a Potential Transformation System", Abstracts, Beltwide Cotton Production Research Conferences, New Orleans, LA, p. 91, (1988).

Gould, J., et al., "Transformation of the Graminae by *Agrobacterium tumefaciens*", *Program and Abstracts, International Society for Plant Molecular Biology, Third International Congress*, Tuscon, AZ, Abstract No. 1277, (Oct. 6-11, 1991).

Gould, J., et al., "Transformation of *Zea mays* L. Using *Agrobacterium tumefaciens* and the Shoot Apex", *Plant Physiology, 95*, 426-434, (1991).

Graves, A., et al., "The Transformation of *Zea mays* Seedlings with *Agrobacterium tumefaciens*", *Plant Mol. Biol., 7*, 43-50, (1986).

Green, C., et al., "Plant Regeneration in Tissue Cultures of Maize", *Crop Sci., 15*, 417-421, (1975).

Green, C., et al., "Somatic Cell Genetic Systems in Corn", *In: Advances in Gene Technology: Molecular Genetics of Plants and Animals*, Academic Press, Inc., pp. 147-157, (1983).

Green, C.E., "New Developments in Plant Tissue Culture and Plant Regeneration", *In: Basic Biology of New Developments in Biotechnology*, Hollaender, A., et al., (eds.), Plenum Press, New York, 195-209, (1983).

Green, C.E., "Somatic Embryogenesis and Plant Regeneration from the Friable Callus of *Zea mays*", *Proceedings of the 5th International Congress on Plant Tissue & Cell Culture*, Tokyo, Japan, 107-108, (1982).

Green, C.E., et al., "Plant Regeneration in Tissue Cultures of Maize", *In: Maize for Biological Research*, Sheridan, W.F., (ed.), Plant Molecular Biology Association, Charlottesville, VA, p. 367-372, (1982).

Grimsley, N., et al., "DNA Transfer from Agrobacterium to *Zea mays* or Brassica by Agroinfection is Dependent on Bacterial Virulence Functions", *Mol. Gen. Genet., 217*, 309-316, (1989).

Gritz, L., et al., "Plasmid-Encoded Hygromycin B Resistance: The Sequence of Hygromycin B Phosphotransferase Gene and Its Expression in *Escherichia coli* and *Saccharomyces cerevisiae*", *Gene, 25*, 179-188, (1983).

Guerineau, F., et al., "Sulfonamide Resistance Gene for Plant Transformation", *Plant Molecular Biology, 15*, 127-136, (1990).

Guerrero, F.D., et al., "Turgor-Responsive Gene Transcription and RNA Levels Increase Rapidly When Pea Shoots are Wilted. Sequence and Expression of Three Inducible Genes", *Plant Mol. Biol., 15*, 11-26, (1990).

Guilley, H., et al., "Transcription of Cauliflower Mosaic Virus DNA: Detection of Promoter Sequences, and Characterization of Transcripts", *Cell, 30*, 763-773, (Oct. 1982).

Gunset, G., "Corn Farmers See Economic, Environment Gold in Designer Genes", *Chicago Tribune*, (Jan. 21, 1991).

Gunset, G., "Genetic Advance May Transform Corn", *Chicago Tribune*, (Apr. 19, 1990).

Gupta, A.S., et al., "Increased Resistance to Oxidative Stress in Transgenic Plants that Overexpress Chloroplastic Cu/Zn Superoxide Dismutase", *Proc. Natl. Acad. Sci. USA, 90*, 1629-1633, (Feb. 1993).

Haccius, B., "Question of Unicellular Origin of Non-Zygotic Embryos in Callus Cultures", *Phytomorphology, 28*, 74-81, (1978).

Hager, K., et al., "Evolution of Seed Storage Protein Genes: Legumin Genes of *Ginkgo biloba*", *Journal of Molecular Evolution*, vol. 41, pp. 457-466, (1995).

Hager, K., et al., "Seed storage proteins of Cupressaceae are homologous to legumins from angiosperms: Molecular characterization of cDNAs from incense cedar (calocedrus decurrens{Torr.}Florin}", *Plant Science*, vol. 116, pp. 85-96, (May 1996).

Hallauer, A.R., et al., "Corn Breeding", *In: Corn and Corn Improvement, Third Edition*, Sprague, G.F., et al., (eds.), American Society of Agronomy, Inc., Madison, WI, p. 463-564, (1988).

Hallborn, J., et al., "Xylitol Production By Recombinant *Saccharomyces cerevisiae*", *Bio/Technology, 9*, 1090-1095, (Nov. 1991).

Harms, C.T., et al., "Regeneration of Plantlets from Callus Cultures of *Zea mays* L.", *Z. Ptlanzenzuchtg. 77*, 347-351, (1976).

Hartman, C.L., et al., "Herbicide Resistant Turfgrass (*Agrostis palustris* Huds.) by Biolistic Transformation", *Bio/technology, 12*, 919-923, (Sep. 1994).

Hartree, E.F., "Determination of Protein: A Modification of the Lowry Method that Gives a Linear Photometric Response", *Analytical Biochemistry, 48*, 422-427, (1972).

Harvey, W.R., et al., "Potassium Ion Transport ATPase in Insect Epithelia", *J. Exp. Biol., 106*, 91-117, (1983).

Haughn, G.W., "Transformation with a Mutant Arabidopsis Acetolactate Synthase Gene Renders Tobacco Resistant to Sulfonylurea Herbicides", *Mol. Gen. Genet., 211*, 266-271, (1988).

Hauptmann, R.M., et al., "Evaluation of Selectable Markers for Obtaining Stable Transformants on the Gramineae", *Plant Physiol., 86*, 602-606, (1988).

Hayashi, H., et al., "Transformation of *Arabidopsis thaliana* with the codA Gene for Choline Oxidase; Accumulation of Glycinebetaine and Enhanced Tolerance to Salt and Cold Stress", *The Plant Journal, 12*, 133-142, (1997).

Heath, J.D., et al., "Discrete Regions of the Sensor Protein VirA Determine the Strain-Specific Ability of Agrobacterium to Agroinfect Maize", *MPMI, 10*, 221-227, (1997).

Heimpel, A.M., et al., "Recent Advances in the Knowledge of Some Bacterial Pathogens of Insects", *Proceedings of the Tenth International Congress of Entomology*, vol. 4, 711-722, (1956).

Heimpel, A.M., et al., "The Site of Action Crystalliferous Bacteria in *Lepidoptera larvae*", *Journal of Insect Pathology, 1*, 152-170, (1959).

Hernalsteens, J.P., et al., "An Agrobacterium-Transformed Cell Culture from the Monocot Asparagus Officinalis", *The EMBO Journal, 3*, 3039-3041, (Dec. 1984).

Herrera-Estrella, L., et al., "Use of Reporter Genes to Study Gene Expression in Plant Cells", *In: Plant Molecular Biology Manual B1*, Kluwer Academic Publishers, Dordrecht, Belgium, pp. 1-22, (1988).

Hibberd, K.A., "Induction, Selection, and Characterization of Mutants in Maize Cell Cultures", *In: Cell Culture and Somatic Cell Genetics of Plants, vol. 1*, Vasil, I.K., (ed.), Academic Press, Inc., Orlando, FL, 571-576, (1984).

Hickle, L.A., et al., "Analytical Chemistry of *Bacillus thuringiensis*: An Overview", *In: Analytical Chemistry of Bacillus thuringiensis*, Hickle, L.A., et al., (eds.), Developed from a Symposium Sponsored by the Division of Agrochemicals at the 198th National Meeting of the American Chemical Society, Miami Beach, FL, vii-ix, 1-8, (Sep. 10-15, 1989).

Hiei, Y., et al., "Efficient Transformation of Rice (*Oryza sativa L*) Mediated by Agrobacterium and Sequence Analysis of the Boundaries of the T-DNA", *The Plant J., 6*, 271-282, (1994).

Hilder, V.A., et al., "A Novel Mechanism of Insect Resistance Engineered into Tobacco", *Nature, 330*, 160-163, (Nov. 12, 1987).

Hodges, T.K., et al., "Genotype Specificity of Somatic Embryogenesis and Regeneration in Maize", *Bio/technology, 4*, 219-223, (Mar. 1986).

Hodges, T.K., et al., "Regeneration of Maize", *In: Biotechnology in Plant Science*, Zaitlin, M., et al., (ed.), Academic Press, Inc., Orlando, FL, 15-33, (1985).

Hoekema, A., et al., "Codon Replacement in the PGK1 Gene of *Saccharomyces cerevisiae*: Experimental Approach to Study the Role of Biased Codon Usage in Gene Expression", *Molecular and Cellular Biology, 7*, 2914-2924, (Aug. 1987).

Hoffman, L.M., et al., "A Modified Storage Protein is Synthesized, Processed, and Degraded in the Seeds of Transgenic Plants", *Plant Mol. Biol., 11*, 717-729, (1988).

Hoffman, L.M., et al., "Synthesis and Protein Body Deposition of Maize 15-kd Zein in Transgenic Tobacco Seeds", *EMBO J., 6*, 3213-3221, (1987).

Hofmann, C., et al., "Binding of the Delta Endotxin from *Bacillus thuringiensis* to Brush-Border Membrane Vesicles of the Cabbage Butterfly (Pieris Brassicae)", *Eur. J. Biochem., 173*, 85-91, (1988).

Hofmann, C., et al., "Specificity of *Bacillus thuringiensis* delta-Endotoxins is Correlated with the Presence of High-Affinity Binding Sites in the Brush Border Membrane of Target Insect Midguts", *Proc. Natl. Acad. Sci. USA, 85*, 7844-7848, (Nov. 1988).

Hofte, H., et al., "Insecticidal Crystal Proteins of *Bacillus thuringiensis*", *Microbiol. Rev., 53*, 242-255, (Jun. 1989)

Hofte, H., et al., "Monoclonal Antibody Analysis and Insecticidal Spectrum of Three Types of Lepidopteran-Specific Insecticidal Crystal Proteins of *Bacillus thuringiensis*", *Applied and Environmental Microbilogy, 54*, 2010-2017, (Aug. 1988).

Hofte, H., et al., "Structural and Functional Analysis of a Cloned Delta Endotoxin of *Bacillus thuringiensis* berliner 1715", *Eur. J. Biochem., 161*, 273-280, (1986).

Hollingworth, R.M., "The Biochemical and Physiological Basis of Selective Toxicity", *In: Insecticidal Biochemistry and Physiology*, Wilkinson, C.F., (ed.), Plenum Press, New York, 431-506, (1976).

Holmstrom, K.O., et al., "Production of the *Escherichia coli* Betaine-Aldehyde Dehydrogenase, An Enzyme Required for the Synthesis of the Osmoprotectant Glycine Betaine, in Transgenic Plants", *The Plant Journal, 6*, 749-758, (1994).

Hong, B., et al., "Cloning and Charcterization of cDNA Encoding a mRNA Rapidly-Induced by ABA in Barley Aleurone Layers", *Plant Molecular Biology, 11*, 495-506, (1988).

Hong, B., et al., "Developmental and Organ-Specific Expression of an ABA- and Stress-Induced Protein in Barley", *Plant. Mol. Biol., 18*, 663-673, (1992).

Hooykaas, P.J., "Transformation of Plant Cell via *Agrobacterium*", *Plant Mol. Biol., 13*, 327-336, (1989).

Hooykaas-Van Slogten, G.S., et al., "Expression of Ti Plasmid Genes in Monocotyledonous Plants Infected with

*Agrobacterium tumefaciens*", *Nature, 311*, 763-764, (Oct. 25, 1984).

Horn, M., et al., "Transgenic Plants of Orchardgrass (*Dactylis glomerata* L.) from Protoplasts", *Chem. Abstracts, 110*, Abstract No. 89869a, 208, (1989).

Horn, M., et al., "Transgenic Plants of Orchardgrass (*Dactylis glomerata* L.) from Protoplasts", *Plant Cell Reports, 7*, 469-472, (1988).

Horsch, R.B., et al., "A Simple and General Method for Transferring Genes into Plants", *Science, 227*, 1229-1231, (Mar. 8, 1985).

Howe, A., et al., "Development of Glyphosphate as a Selectable Marker for the Production of Fertile Transgenic Corn Plants", *In Vitro Cell. Develop. Biol., 28A*, Abstract No. P-1136, (Jul.-Aug. 1992).

Hu, C.C., et al., "Factors Contributing to the Anomalous Electrophoretic Mobility of Cucumoviruses Coat Proteins in SDS/Polyacrylamide Gels", *Phytopathology, 83*, Abstract No. A393, 1374, (Dec. 1993).

Hu, N.T., et al., "Primary Structure of a Genomic Zein Sequence of Maize", *The EMBO Journal, 1*, 1337-1342, (1982).

Huang, Y., et al., "Factors Influencing Stable Transformation of Maize Protoplasts by Electroporation", *Plant Cell, Tissue and Organ Culture, 18*, 281, (1989).

Huber, H.E., et al., "*Bacillus thuringiensis* delta-Endotoxin: Composition and Activation", *In: Pathogenesis of Invertebrate Microbial Diseases*, Davidson, E.W., (ed.), Allanheld, Osmun & Co. Publishers, Inc., Totowa, NJ, 209-234, (1981).

Huber-Lukac, M., et al., "Characterization of Monoclonal Antibodies to a Crystal Protein of *Bacillus thuringiensis* subsp. *kurstaki*", *Infection and Immunity, 54*, 228-232, (Oct. 1986).

Imbrie-Milligan, C., et al., "Microcallus Growth from Maize Protoplasts", *Planta, 171*, 58-64, (1987).

Imbrie-Milligan, C.W., et al., "Microcallus Formation from Maize Protoplasts Prepared from Embryogenic Callus", *Planta, 168*, 395-401, (1986).

Ishitani, M., et al., "Expression of the Betaine Aldehyde Dehydrogenase Gene in Barley in Response to Osmotic Stress and Abscisic Acid", *Plant Molecular Biology, 27*, 307-315, (1995).

Jahne, A., et al., "Genetic Engineering of Cereal Crop Plants: A Review", *Euphytica, 85*, 35-44, (1995).

Jahne, A., et al., "Regeneration of Fertile Plants from Protoplasts Derived from Embryogenic Cell Suspensions of Barley (*Hordeum vulgare* L.)", *Plant Cell Rep., 10*, 1-6, (1991).

Jahne, A., et al., "Regeneration of Transgenic, Micropore-Derived, Fetile Barley", *Theor. Appl. Genet., 89*, 525-533, (1994).

Jarrett, P., "Potency Factors in the delta-Endotoxin of *Bacillus thuringiensis* var. *aizawi* and the Significance of Plasmids in their Control", *Journal of Applied Bacteriology, 58*, 437-448, (1985).

Jaworski, J.G., et al., "A Cerulenin Insensitive Short Chain 3-Ketoacyl-Acyl Carrier Protein Synthase in *Spinacia oleracea* Leaves", *Plant Physiol., 90*, 41-44, (1989).

Jayne, S., et al., "Analysis of Elite Transgenic Maize Plants Produced by Microprojectile Bombardment", *Program and Abstracts, International Society for Plant Molecular Biology, Third International Congress*, Tucson, AZ, Abstract No. 338, (Oct. 6-11, 1991).

Jaynes, J.M., et al., "Plant Protein Improvement by Genetic Engineering: Use of Synthetic Genes", *Trends in Biotechnology, 4*, 314-320, (Dec. 1986).

Jefferson, R.A., "Assaying Chimeric Genes in Plants: The GUS Gene Fusion System", *Plant Mol. Biol. Rep., 5*, 387-405, (1987).

Jefferson, R.A., et al., "Beta-Glucuronidase from *Escherichia coli* as a Gene-Fusion Marker", *Proc. Nat. Acad. Sci. USA, 83*, 8447-8451, (1986).

Jefferson, R.A., et al., "GUS Fusions: Beta-Glucuronidase as a Sensitive and Versatile Gene Fusion Marker in Higher Plants", *EMBO J., 6*, 3901-3907, (1987).

Johnson, D.E., "Toxicity of *Bacillus thuringiensis* Entomocidal Protein Toward Cultured Insect Tissue", *Journal of Invertebrate Pathology, 38*, 94-101, (1981).

Johri, M.M., et al., "Genetic Approaches to Meristem Organization", *In: Maize for Biological Research*, Sheridan, W.F., (ed.), Plant Molecular Biology Association, Charlottesville, VA, p. 301-310, (1982).

Jones, H., et al., "Recent Advances in Plant Electroporation", *Oxford Surveys of Plant Molecular and Cell Biology, 4*, 347-357, (1987).

Jones, H., et al., "Transient Gene Expression in Electroporated Solanum Protoplasts", *Plant Mol. Biol., 13*, 503-511, (1989).

Josefsson, L.G., et al., "Structure of a Gene Encoding the 1.7 S Storage Protein, Napin, from *Brassica napus*", *The Journal of Biological Chemistry, 262*, 12196-12201, (Sep. 5, 1987).

Kaasen, I., et al., "Molecular Cloning and Physical Mapping of the otsBA Genes, Which Encode the Osmoregulatory Trehalose Pathway of *Escherichia coli*: Evidence that Transcription is Activated by KatF (AppR)", *Journal of Bacteriology, 174*, 889-898, (Feb. 1992).

Kaeppler, H.F., et al., "Silicon Carbide Fiber-Mediated DNA Delivery into Plant Cells", *Plant Cell Rep., 9*, 415-418, (1990).

Kamo, K., et al., "Establishment and Characterization of Long-Term Embryonic Maize Callus and Cell Suspension Cultures", *Plant Sci., 45*, 111-117, (1986).

Kamo, K., et al., "Regeneration of *Zea mays* L. from Embryogenic Callus", *Bot. Gaz., 146*, 327-334, (1985).

Kao, K.N., et al., "Nutritional Requirements for Growth of *Vicia hajastana* Cells and Protoplasts at a Very Low Population Density in Liquid Media", *Planta, 126*, 105-110, (1978).

Kartha, K., et al., "Transient Expression of Chloramphenicol Acetyl Transferase(CAT) Gene in Barley Cell Cultures and Immature Embryos Through Microprojectile Bombardment", *Plant Cell. Rep., 8*, 429-432, (1989).

Kausch, A.P., et al., "Effects of Microprojectile Bombardment on Embryogenic Suspension Cell Cultures of Maize (*Zea mays* L.) Used for Genetic Transformation", *Planta, 196*, 501-509, (1995).

Kavi Kishor, P.B., et al., "Overexpression of 1-Pyrroline-5-Carboxylate Synthetase Increases Proline Production and Confers Osmotolerance in Transgenic Plants", *Plant Physiol., 108*, 1387-1294, (1995).

Kay, R., et al., "Duplication of CaMV 35S Promoter Sequences Creates a Strong Enhancer for Plant Genes", *Science, 236*, 1299-1302, (Jun. 5, 1987).

Kim, C.S., et al., "Improvement of Nutritional Value and Functional Properties of Soybean Glycinin by Protein Engineering", *Protein Engineering, 3*, 725-731, (1990).

King, P., et al., "Maize", *In: Handbook of Plant Cell Culture, vol. 2*, Sharp, W.R., et al., (eds.), Macmillan Publishing Company, New York, 69-91, (1984).

Kirihara, J., et al., "Differential Expression of a Gene for a Methionine-Rich Storage Protein in Maize", *Mol. Gen. Genet., 211*, 477-484, (1988).

Kirihara, J., et al., "Isolation and Sequence of a Gene Encoding a Methionine-Rich 10-kDa Zein Protein from Maize", *Gene, 71*, 359-370, (1988).

Klein, T.M., "Transformation of Maize Through Particle Bombardment", *In: Biotechnology in Agriculture and Forestry, 25*, Maize, Bajaj, Y.P.S., (ed.), Springer-Verlag, Berlin, 241-251, (1994).

Klein, T.M., et al., "Advances in Direct Gene Transfer into Cereals", *In: Genetic Engineering: Principles and Methods, vol. 11*, Setlow, J.K., (ed.), Plenum Publishing Corp., New York, 13-31, (1989).

Klein, T.M., et al., "Factors Influencing Gene Delivery into *Zea mays* Cells by High Velocity Microprojectiles", *Bio/Technology, 6*, 559-563, (1988).

Klein, T.M., et al., "Genetic Transformation of Maize Cell by Particle Bombardment and the Influence of Methylation on Foreign Gene Expression", *In: Gene Manipulation in Plant Improvement II*, Gustafson, J.P., (ed.), Plenum Press, NY, pp. 265-266, (1990).

Klein, T.M., et al., "Genetic Transformation of Maize Cells by Particle Bombardment", *Plant Physiology, 91*, 440-444, (1989).

Klein, T.M., et al., "High-Velocity Microprojectiles for Delivering Nucleic Acids into Living Cells", *Nature, 327*, 70-73, (1987).

Klein, T.M., et al., "Particle Bombardment: A Universal Approach for Gene Transfer to Cells and Tissues", *Current Opinion in Biotechnology, 4*, 583-590, (1993).

Klein, T.M., et al., "Particle Gun Technology: A Novel Method for the Introduction of DNA into Living Cells", *Program and Abstracts for an International Symposium: "Biotechnology in Plant Science: Relevance to Agriculture in the Eighties"*, Poster, #28, Ithaca, NY, 25, (Jun. 23-27, 1985).

Klein, T.M., et al., "Progress in the Genetic Transformation of Recalcitrant Crop Species", *Aspects of Applied Biology, 39*, 35-44, (1994).

Klein, T.M., et al., "Regulation of Anthocyanin Biosynthetic Genes Introduced into Intact Maize Tissues by Microprojectiles", *Pro. Nat. Acad. Sci. USA, 86*, 6681-6685, (Sep. 1989).

Klein, T.M., et al., "Stable Genetic Transformation on Intact Nicotiana Cells by the Particle Bombardment Process", *Proc. Natl. Acad. Sci. USA, 95*, 5502-5505, (Nov. 1988).

Klein, T.M., et al., "Transfer of Foreign Genes into Intact Maize Cells with High-Velocity Microprojectiles", *Proc. Nat. Acad. Sci. USA,, vol. 85*, 4305-4309, (1988).

Klein, T.M., et al., "Transformation of Microbes, Plants and Animals by Particle Bombardment", *Biotechnology, 10*, 286-291, (Mar. 1992).

Knight, M.R., et al., "Transgenic Plant Aequorin Reports the Effects of Touch and Cold-Shock and Elicitors on Cytoplasmic Calcium", *Nature, 352*, 524-526, (Aug. 8, 1991).

Knowles, B.H., et al., "Characterization and Partial Purification of a Plasma Membrane Receptor for *Bacillus thuringiensis* var. Kurstaki Lepidopteran-Specific delta-Endotoxin", *J. Cell Sci., 83*, 89-101, (1986).

Knowles, B.H., et al., "Lectin-Like Binding of *Bacillus thuringiensis* var. Kurstaki Lepidopteran-Specific Toxin is an Initial Step in Insecticidal Action", *FEBS Letters, 168*, 197-202, (Mar. 1984).

Kogami, H., et al., "Molecular and Physiological Evaluation of Transgenic Tobacco Plants Expressing a Maize Phosphoenolpyruvate Carboxylase Gene Under the Control of the Cauliflower Mosaic Virus 35S Promoter", *Biol. Abstr., 98*, Abstract No. 147991, p. AB-596, (1994).

Kohno-Murase, J., et al., "Improvement in the quality of seed storage protein by transformation of *Brassica napus* with an antisense gene for cruciferin", *Theor. Appl. Genet., vol. 91*, pp. 627-631, (1995).

Kononowicz, H., et al., "Subdomains of the Octopine Synthase Upstream Activating Element Direct Cell-Specific Expression in Transgenic Tobacco Plants", *The Plant Cell, 4*, 17-27, (Jan. 1992).

Kozak, M., "Compilation and Analysis of Sequences Upstream from the Translational Start Site in Eukaryotic mRNAs", *Nucleic Acids Research, 12*, 857-872, (1984).

Kozak, M., "Point Mutations Define a Sequence Flanking the AUG Initiator Codon that Modulates Translation by Eukaryotic Ribosomes", *Cell, 44*, 283-292, (1986).

Koziel, M.G., et al., "Field Performance of Elite Transgenic Maize Plants Expressing as Insecticidal Protein Derived from *Bacillus thuringiensis*", *Bio/Technol., 11*, 194-200, (1993).

Koziel, M.G., et al., "The Insecticidal Crystal Proteins of *Bacillus thuringiensis*: Past, Present and Future Uses", *Biotechnology and Genetic Reviews, 11*, 171-228, (Dec. 1993).

Kreitlow, B., "Genetic Engineering 'Breakthrough' Disputed ", *Cedar Rapids Gazette*, (Apr. 20, 1990).

Kriz, A.L., et al., "Characterization of the Maize Globulin-2 Gene and Analysis of Two Null Alleles", *Biochemical Genetics, 29*, 241-254, (1991).

Kuhlemeier, C., et al., "Regulation of Gene Expression in Higher Plants", *Ann. Rev. Plant Physiol., 38*, 234-239, (1987).

Lamark, T., et al., "DNA Sequence and Analysis of the bet Genes Encoding the Osmoregulatory Choline-Glycine Betaine Pathway of *Escherichia coli*", *Molecular Microbiology, 5*, 1049-1064, (1991).

Lamppa, G., et al., "Analysis of Two Linked Genes Coding for the Acyl Carrier Protein (ACP) from *Arabidopsis thaliana* (Columbia)", *Plant Molecular Biology, 16*, 469-474, (1991).

Landi, P., et al., "Genetic Analysis of Leaf ABA Concentration and of Agronomic Traits in Maize Hybrids Grown Under Different Water Regimes", *Maydica, 40*, 179-186, (1995).

Langridge, P., et al., "Transformation of cereals via Agrobacterium and the Pollen Pathway: A Critical Assessment", *The Plant Journal, 2*, 613-638, (1992).

Langridge, W.H., et al., "Electric Field Mediated DNA Transformation in Plant Protoplasts", *Program and Abstracts for an International Symposium: "Biotechnology in Plant Science: Relevance to Agriculture in the Eighties"*, Ithaca, NY, Poster #30, p. 25, (Jun. 23-27, 1985).

Larkins, B.A., et al., "Modification of Maize-Seed Protein Quality", *Am. J. Clin. Nutr., 58*, 264S-269S, (1993).

Laursen, C.M., et al., "Production of Fertile Transgenic Maize by Electroporation of Suspension Culture Cells", *Plant Mol. Biol., 24*, 51-61, (1994).

Lazzeri, P., et al., "In Vitro Genetic Manipulation of Cereals and Grasses", *Adv. Cell Culture, 6*, 291-293, (1988).

Leason, M., et al., "Inhibition of Pea Leaf Glutamine Synthetase by Methionine Sulphoximine, Phosphinothricin and Other Glutamate Analogues", *Biochemistry, 21*, 855-857, (1982).

Lee, B., "Cereal Transformation", *Plants Today*, 9-11, (Jan.-Feb. 1989).

Lee, J.S., et al., "Gene Transfer into Intact Cells of Tobacco by Electroporation", *Korean J. Genetics, 11*, 65-72, (1989).

Leemans, J., "Genetic Engineering for Fertility Control", *Conference Record, Keytone Symposium on Crop Improvement via Biotechnology: An International Perspective*, Abstract No. Y016, (Apr. 10-26, 1992).

Lemaux, P.G., et al., "Selection of Stable Transformants from Maize Suspension Cultures Using the Herbicide Bialaphos", *J. Cell. Biochem., 14e*, Abstract R230, 304, (Mar. 31, 1990).

Levitt, J., "Growth Regulators", *In: Introduction to Plant Physiology*, The C.V. Mosby Company, St. Louis, MO, p. 241, (1969).

Li, B.J., et al., "Introduction of Foreign Genes into the Seed Embryo Cells of Rice by Electroinjection and the Regeneration of Transgenic Rice Plants", *Science in China, 34*, 925-931, (1991).

Li, J., et al., "The *Arabidopsis thaliana* trp5 Mutant Has a Feedback-Resistant Anthranilate Synthase and Elevated Soluble Tryptophan", *Plant Physiol., 110*, 51-59, (1996).

Li, X.Q., et al., "GUS Expression in Rice Tissue Using Agrobacterium mediated Transformation", *Program and Abstracts, International Society for Plant Molecular Biology, Third International Congress,*, Tucson, AZ, Abstract No. 385, (Oct. 6-11, 1991).

Lin, F.F., et al., "Transformation and Analysis of Inducible PAL Genes in Potato", *In Vitro Cellular and Developmental Biology, 28*, Abstract No. P-1129, p. 123A, (Mar. 1992).

Lindsey, K., et al., "Electroporation of Cells", *Physiol. Plant., 79*, 168-172, (1990).

Lindsey, K., et al., "Stable Transformation of Sugarbeet Protoplasts by Electroporation", *Plant Cell Rep., 8*, 71-74, (1989).

Lindsey, K., et al., "The Permeability of Electroporated Cells and Protoplasts of Sugar Beet", *Planta, 172*, 346-355, (1987).

Lindsey, K., et al., "Transient Gene Expression in Electroporated Protoplasts and Intact Cells of Sugar Beet", *Plant Mol. Biol., 10*, 43-52, (1987).

Looker, D., "Dekalb Claims Success in Effort to Alter Genetic Makeup of Corn", *Des Moines Register*, (Apr. 19, 1990).

Lopes, M.A., et al., "Endosperm Origin, Development and Function", *The Plant Cell, 5*, 1383-1399, (Oct. 1993).

Lorz, H., et al., "Advances in Tissue Cultures and Progress Towards Genetic Transformation of Cereals", *Plant Breeding, 100*, 1-25, (1988).

Lorz, H., et al., "Gene Transfer to Cereal Cells Mediated by Protoplast Transformation", *Mol. Gen. Genet., 199*, 178-182, (1985).

Lowe, K., et al., "Germline Transformation of Maize Following Manipulation of Chimeric Shoot Meristems", *Biotechnology, 13*, 677-682, (Jul. 1995).

Lowe, K., et al., "Germline Transformation of Maize using Shoot Multiplication to Enlarge Chimeric Sectors", *In Vitro Cellular and Developmental Biology*, Program Issue, Congress on In Vitro Biology, Abstract No. P-1095, 72A, (May 20-24, 1995).

Lowe, K., et al., "Plant Regeneration via Organogenesis and Embryogenesis in the Maize Inbred Line B73", *Plant Science, 41*, 125-132, (1985).

Lu, C., et al., "Improved Efficiency of Somatic Embryogenesis and Plant Regeneration on Tissue Cultures of Maize (*Zea mays* L.)", *Theor. Appl. Genet., 66*, 285-289, (1983).

Lu, C., et al., "Somatic Embryogenesis in *Zea mays*L.", *Theor. Appl. Genet, 62*, 109-112, (1982).

Luckow, V.A., et al., "Trends in the Development of Baculovirus Expression Vectors", *Bio/Technology, 6*, 47-55, (1988).

Ludwig, S., et al., "A Regulatory Gene as a Novel Visible Marker for Maize Transformation", *Science, 247*, 449-450, (1990).

Ludwig, S., et al., "High Frequency Callus Formation from Maize Protoplasts", *Theor. Appl. Genet., 71*, 344-350, (1985).

Ludwig, S., et al., "Lc, a Member of the Maize R Gene Family Responsible for Tissue-Specific Anthocyanin Production, Encodes a Protein Similar to Transcriptional Activators and Contains the myc-Homology Region", *Proc. Natl. Acad. Sci. USA, 86*, 7092-7096, (1989).

Ludwig, S., et al., "Maize R Gene Family: Tissue-Specific Helixp-Loop-Helix Proteins", *Cell, 62*, 849-851, (1990).

Lutcke, H., et al., "Selection of AUG Initiation Codons Differs in Plants and Animals", *EMBO J., 6*, 43-48, (1987).

Luthy, P., "Insecticidal Toxins of Bacillus thuringiensis", *FEMS Microbiology Letters, 8*, 1-7, (1980).

Maas, C., et al., "A Highly Optimized Monocot Expression Cassette: Application for Barley Transformation and Barley Virus Research", *Program and Abstracts, International Society for Plant Molecular Biology, Third International Congress*, Tucson, AZ, Abstract No. 386, (Oct. 6-11, 1991).

Mackey, C.J., et al., "Transgenic Maize", *In: Transgenic Plants, vol. 2*, Kung, S.-D., et al., (eds.), Academic Press, Inc., 21-33, (Oct. 1992).

Maddock, S.E., et al., "Expression in Maize Plants of Wheat Germ Agglutinin, a Novel Source of Insect Resistance", *Program and Abstracts, International Society for Plant Molecular Biology, Third International Congress*, Tucson, AZ, Abstract No. 372, (Oct. 6-11, 1991).

Malan, C., et al., "Correlation Between CuZn Superoxide Dismutase and Glutathione Reductase, and Environmental and Xenobiotic Stress Tolerance in Maize Inbreds", *Plant Science, 69*, 157-166, (1990).

Maliga, P., "Plastid Transformation: A New Tool for Basic Science and for Biotechnological Applications", *In Vitro Cellular and Developmental Biology, 31*, Abstract No. W-18, 28A, (Mar. 1995).

Mangano, M.L., et al., "Long-Term Cold Storage of Regenerable Maize Callus", *In Vitro Cellular and Developmental Biology, 25*, Abstract No. 224, p. 66A, (Mar. 1989).

Mariani, C., et al., "Engineered Male Sterility in Plants", *Symposia of the Society for Experimental Biology, No. XLV*, Proceedings of a Meeting Held at the University of Glasgow, Scotland, 271-279, (1991).

Mariani, T., et al., "The Production and Analysis of Genetically-Engineered Male-Sterile Plants of Maize", *Abstracts, 35th Annual Maize Genetics Conference*, St. Charles, IL, Poster No. 46, p. 45, (Mar. 18-21, 1993).

Marks, M.D., et al., "Nucleotide Sequence Analysis of Zein mRNAS from Maize Endosperm", *The Journal of Biological Chemistry, 260*, 16451-16459, (Dec. 25, 1985).

Martens, J.W., et al., "Insecticidal Activity of a Bacterial Crystal Protein Expressed by a Recombinant Baculovirus in Insect Cells", *Applied and Environmental Microbiology*, 56, 2764-2770, (Sep. 1990).

Martens, J.W., et al., "Mapping and Characterization of the Entomocidal Domain of the Bacillus thuringiensis CryIA(b) Protoxin", *Mol. Gen. Genet.*, 247, 482-487, (1995).

Masumura, T., et al., "cDNA Cloning of an mRNA Encoding a Sulfur-Rich 10 kDA Prolamin Polypeptide in Rice Seeds", *Plant Mol. Biol.*, 12, 123-130, (1989).

Matthews, B.F., et al., "Nutritional Improvement of the Aspartate Family of Amino Acids in Edible Crop Plants", *Amino Acids*, 4, 21-34, (1993).

McCabe, D.E., et al., "Stable Transformation of Soybean (Glycine max) by Particle Acceleration", *Bio/Technology*, 6, 923-926, (Aug. 1988).

McCue, K.F., et al., "Drought and Salt Tolerance: Towards Understanding and Application", *TIBTECH*, 8, 358-362, (Dec. 1990).

McDaniel, C., et al., "Cell-Linage Patterns in the Shoot Apical Meristem of the Germinating Maize Embryo", *Planta*, 175, 13-22, (1988).

McElroy, D., et al., "Isolation of an Efficient Actin Promoter for Use in Rice Transformation", *The Plant Cell*, 2, 163-171, (Feb. 1990).

Mcfarlin, D.R., "Gallus gallus PH-27 and Vasoactive Intestinal Peptide (VIP) mRNA, complete sequence", *EMBL/GenBank/DDJB Databases, Accession No. GG09350*, (May 1994).

Meadows, C., et al., "Characterization of Cells and Protoplasts of the B73 Maize Cell Line", *Plant Sci. Lett.*, 28, 337-348, (1982-1983).

Mehta, A., et al., "A Step Towards Developing Transgenic Plants With High Nutritional Quality", *Proc. Indian Natl. Sci. Acad.*, B60, 375-380, (1994).

Mendel, R., et al., "Delivery of Foreign Genes to Intact Barley Cell by High-Velocity Microprojectiles", *Theor. Appl. Genet.*, 78, 31-34, (1989).

Merryweather, A.T., et al., "Construction of Genetically Engineered Baculovirus Insecticides Containing the Bacillus thuringiensis subsp. Kurstaki HD-73 Delta Endotoxin", *Journal of General Virology*, 71, 1535-1544, (1990).

Messing, J., "Corn Storage Protein: A Molecular Genetic Model", Division of Energy BioSciences—Summaries of FY 1990 Activities, Abstract No. 135, p. 70, (1990).

Mikula, B.C., "Programming Heritable Epigenetic Change in Gene Expression with Temperature and Light", *Abstracts, 35th Annual Maize Genetics Conference*, St. Charles, IL, p. 5, (Mar. 18-21, 1993).

Milborrow, B.V., "Abscisic Acid and Other Hormones", In: *The Physiology and Biochemistry of Drought Resistance in Plants*, Paleg, L.G., et al., (eds.), Academic Press, New York, pp 347-388, (1981).

Mink, G.I., "Pollen- and Seed-Transmitted Viruses and Viroids", *Annu. Rev. Phytopathol.*, 31, 375-402, (1993).

Moffat, A.S., "Corn Transformed", *Science*, 249, 630, (Aug. 10, 1990).

Moffat, A.S., "Higher Yielding Perennials Point the Way to New Crops", *Science*, 274, 1469-1470, (Nov. 29, 1996).

Molnar, S.J., et al., "Initiation of Totipotent Tissue Cultures from Undeveloped Axillary and Secondary Ears", *Maize Genetics Cooperation Newsletter*, 54, 52-53, (Mar. 31, 1980).

Montoliu, L., et al., "A Tandem of alpha-Tubulin Genes Preferentially Expressed in Radicular Tissues from Zea mays", *Plant Molecular Biology*, 14, 1-15, (1989).

Morelli, G., et al., "A Short Conserved Sequence is Involved in the Light-Inductibility of a Gene Encoding Ribulose 1, 5-bisphosphate Carboxylase Small Subunit of Pea", *Nature*, 315, (May 16, 1995).

Morikawa, H., et al., "Gene Transfer into Intact Plant Cells by Electroporation Through Cell Walls and Membranes", *Gene*, 41, 121-124, (1986).

Morocz, S., et al., "An Improved System to Obtain Fertile Regenerants via Maize Protoplasts Isolated From a Highly Embryogenic Suspension Culture", *Theor. Appl. Genet.*, 80, 721-726, (1990).

Morocz, S., et al., "Two Approaches to Rendering Zea mays L. Applicable to Tissue Culture Manipulations", *Abstract, VII International Congress on Plant Tissue and Cell Culture*, Amsterdam, The Netherlands, Abstract No. 209, p. 190, (Jun. 24-29, 1990).

Morris, G.D., "Ciba-Geigy Enters the $1.5-Billion/Year Corn Biotech Race", *Chemical Week*, (Sep. 12, 1990).

Mundy, J., et al., "Abscisic Acid and Water-Stress Induce the Expression of a Novel Rice Gene", *The EMBO Journal*, 7, 2279-2286, (1988).

Mundy, J., et al., "Selective Expression of a Probable Amylase/Protease Inhibitor in Barley Aleurone Cells: Comparison to the Barley Amylase/Subtilisin Inhibitor", *Planta*, 169, 51-63, (1986).

Murakami, T., et al., "The Bialaphos Biosynthetic Genes of Streptomyces hygroscopicus: Molecular Cloning and Characterization of the Gene Cluster", *Mol. Gen. Genet.*, 205, 42-50, (1986).

Murashige, T., et al., "A Revised Medium for Rapid Growth and Bio Assays with Tobacco Tissue Cultures", *Physiol. Plant.*, 15, 473-497, (1962).

Murphy, D.W., et al., "Bacillus thuringiensis Enzyme-Digested Delta Endotoxin: Effect on Cultured Insect Cells", *Science*, 194, 954-956, (Nov. 26, 1976).

Murphy, H.L., "New Dekalb-Pfizer Seed Chief to Harvest R & D Breakthroughs", *Crain's Business Weekly*, 38-39, (1990).

Murray, E.E., et al., "Analysis of Unstable RNA Transcripts of Insecticidal Crystal Protein Genes of Bacillus thuringiensis in Transgenic Plants and Electroporated Protoplasts", *Plant Molecular Biology*, 16, 1035-1050, (1991).

Murray, E.E., et al., "Codon Usage in Plant Genes", *Nucleic Acids Research*, 17, 477-498, (1989).

Murry, L.E., et al., "Transgenic Corn Plants Expressing MDMV Strain B Coat Protein are Resistant to Mixed Infections of Maize Dwarf Mosaic Virus and Maize Chlorotic Motle Virus", *Bio/Technology*, 11, 1559-1564, (1993).

Nelson, R.S., "Virus Tolerance, Plant Growth and Field Performance of Transgenic Tomato Plants Expressing Coat from Tobacco Mosaic Virus", *Bio/Technology*, 6, 403-409, (Apr. 1988).

Nelson, T., "New Horses for Monocot Gene Jockeys", *The Plant Cell*, 2, 589, (1990).

Neuffer, M.G., "Growing Maize for Genetic Purposes", In: *Maize for Biological Research*, Sheridan, W.F., (ed.), Plant Molecular Biology Association, Charlottesville, VA., p. 19-30, (1988).

Nishida, I., et al., "The Gene and the RNA for the Precursor to the Plastid-Located Glycerol-3-phosphate Acyltransferase of Arabidopsis thaliana", *Plant Molecular Biology, 21*, 267-277, (1993).

Nishiitsutsuji-Uwo, J., et al., "Mode of Action of Bacillus thuringiensis Delta-Endotoxin: Effect on TN-368 Cells", *Journal of Invertebrate Pathology, 34*, 267-275, (1979).

Niyogi, K.K., et al., "Suppressors of trp I Fluorescence Identify a New Arabidopsis Gene, TRP4, Encoding the Anthranilate Synthase beta Subunit", *The Plant Cell, 5*, 1011-1027, (1993).

Niyogi, K.K., et al., "Two Anthranilate Synthase Genes in Arabidopsis: Defense-Related Regulation of the Tryptophan Pathway", *The Plant Cell, 4*, 721-733, (1992).

O'Reilly, D.R., et al. "A Baculovirus Blocks Insect Molting by Producing Ecdysteroid UDP-Glucosyl Transferase", *Science, 245*, 1110-1112, (Sep. 8, 1989).

Ochatt, S.J., et al., "Selection for Salt/Drought Tolerance Using Isolated Protoplasts and Protoplast-Derived Calli of Colt Cherry (Prunus avium x pseudocerasus)", *In: Progress in Plant Protoplast Research*, Puite, K.J., et al., (eds.), Kluwer Academic Publishers, Dordrecht, The Netherlands, 391-392, (1988).

Odell, J., et al., "Identification of DNA Sequences Required for Activity of the Cauliflower Mosaic Virus 35S Promoter", *Nature, 313*, 810-811, (1985).

Oeda, K., et al., "Formation of Crystals of the Insecticidal Proteins of Bacillus thuringiensis subsp. aizawai IPL7 in Escherichia coli", *Journal of Bacteriology, 171*, 3568-3571, (Jun. 1989).

Ohta, Y., et al., "Gene Manifestation of Exogenous DNA Applied to Self-Propagating Stigma (Gene Action Revealed in the M1 and M2 Generations from Self-Pollination Applying Exogenous DNA)", *Jap. J. Breed., 30*, 184-185, (1980).

Ohta, Y., et al., "High-Efficiency Genetic Transformation of Maize by a Mixture of Pollen and Exogenous DNA", *Proc. Nat. Acad. Sci. USA, 83*, 715-719, (1986).

Omirullen, S., et al., "Activity of a Chimeric Promoter with the Doubled CaMV 35S Enhancer in Protoplast-Derived Cells and Transgenic Plants in Maize", *Plant Mol. Biol., 21*, 415-428, (1993).

Ozias-Akins, P., et al., "In Vitro Regeneration and Genetic Manipulation of Grasses", *Physiol. Plant., 73*, 565-569, (1988).

Ozias-Akins, P., et al., "Progress and Limitations in the Culture of Cereal Protoplasts", *Trends in Biotechnology, 2*, 119-123, (1984).

Pang, Y., et al., "Synthesis and Toxicity of Full-Length and Truncated Bacterial CryIVD Mosquitocidal Proteins Expressed in Lepidopteran Cells Using a Baculovirus Vector", *Journal of General Virology, 73*, 89-101, (1992).

Park, S.H., et al., "Selection of Maize Transformants form Shoot Apex Cultures Cocultivated with Agrobacterium Containing the Bar Gene", *In Vitro Cell Develop. Biol., 29A*, Abstract No. P-1102, 85, (1993).

Park, W.D., et al., "High-Level, Sucrose-Inducible Expression of a Chimeric Patatin-GUS Gene In Leaf Explants of Transgenic Tobacco Plants", *Journal of Cellular Biochemistry, 13D*, Abstract No. M 343, p. 310, (Mar. 27-Apr. 7, 1989).

Parker, W.B., et al., "Selection and Characterization of Sethoxydim-Tolerant Maize Tissue Cultures", *Plant Physiol., 92*, 1220-1225, (1990).

Paszkowski, J., et al., "Direct Gene Transfer to Plants", *The EMBO Journal, 3*, 2717-2722, (1984).

Pederson, K., et al., "Sequence Analysis and Characterization of a Maize Gene Encoding a High-Sulfur Zein Protein of Mr 15, 000", *J. Biol. Chem., 261*, 6279-6284, (1986).

Perl, A., et al., "Bacterial Dihydrodipicolinate Synthase and Desensitized Aspartate Kinase: Two Novel Selectable Markers for Plant Transformation", *Bio/Technol., 11*, 715-718, (1993).

Perlack, F.J., et al., "Modification of the Coding Sequence Enhances Plant Expression of Insect Control Protein Genes", *Proc. Nat. Acad. Sci. USA, 88*, 3324-3328, (1991).

Perlak, F.J., et al., "Expression of Bacillus thuringiensis Proteins in Transgenic Plants", *In: Biotechnology, Biological Pesticides and Novel Plant-Pest Resistance for Insect Pest Management*, Roberts, D.W., et al., (eds.), Insect Pathology Resource Center, Boyce Thompson Institute for Plant Research, Cornel University, Ithaca, NY, 77-81, (1988).

Perlak, F.J., et al., "Genetically Improved Potatoes: Protection from Damage by Colorado Potato Beetles", *Plant Molecular Biology, 22*, 313-321, (1993).

Perlak, F.J., et al., "Insect Resistant Cotton Plants", *Bio/technology, 8*, 939-943, (Oct. 1990).

Pescitelli, S.M., et al., "Stable Transformation via Electroporation into Maize Type II Callus and Regeneration of Fertile Transgenic Plants", *Plant Cell Reports, 14*, 712-716, (1995).

Phillips, R.L., et al., "Cell/Tissue Culture and In Vitro Manipulation", *In: Corn and Corn Improvement, Third Edition*, Sprague, G.F., et al, (eds.), American Society of Agronomy, Madison, WI, p. 345-387, (1988).

Phillips, R.L., et al., "Elevated Protein-Bound Methionine in Seeds of a Maize Line Resistant to Lysine Plus Threonine", *Cereal Chem., 62*, 213-218, (1985).

Piatkowski, D., et al., "Characterization of Five Abscisic Acid-Responsive cDNA Clones Isolated from the Desiccation-Tolerant Plant Craterostigma plantagineum and Their Relationship to Other Water-Stress Genes", *Plant Physiology, 94*, 1682-1688, (Jun. 1990).

Poehlman, J.M., *In: Breeding Field Crops, 3rd Edition*, AVI Publishing Co., Westport, CT, 469-481, (1988).

Poehlman, J.M., *In: Breeding Field Crops, 3rd Edition*, AVI Publishing Company, Inc., Westport, CT, 203-206, (1988).

Poehlman, J.M., *In: Breeding Field Crops, 3rd Edition*, AVI Publishing Company, Inc., Westport, CT, 149-152, (1987).

Poethig, R.S., "Maize—The Plant and Its Parts", *In: Maize for Biological Research*, Sheridan, W.F., (ed.), Plant Molecular Biology Association., Charlottesville, VA, 9-18, (1982).

Porobo-Dessai, A., et al., "Expression of gusA Gene with an Intron in Sweet Potato and Garden Egg Plant", *In Vitro Cellular and Development Biology 13D*, Abstract No. P-1130, 123A, (Mar. 1992).

Potrykus, I., "Gene Transfer to Cereals: An Assessment", *Bio/Technology, 8*, pp. 535-542, (Jun. 1990).

Potrykus, I., "Gene Transfer to Cereals: An Assessment", *Trends in Biotechnology, 7*, 269-273, (Oct. 1989).

Potrykus, I., "Gene Transfer to Plants: Assessment and Perspectives", *Physiol. Plant., 79*, 125-134, (1990).

Potrykus, I., et al., "Callus Formation from Cell Culture Protoplasts of Corn (Zea mays L.)", *Theor. Appl. Genet., 54*, 209-214, (1979).

Potrykus, I., et al., "Callus Formation from Stem Protoplasts of Corn (Zea mays L.)", *Mol. Gen. Genet., 156*, 347-350, (1977).

Potrykus, I., et al., "Direct Gene Transfer to Cells of a Graminaceous Monocot", *Mol. Gen. Genet., 199*, 183-188, (1985).

Potrykus, I., et al., "Direct Gene Transfer: State of the Art and Future Potential", *Plant Molecular Biology Reporter, 3*, 117-128, (Summer 1985).

Potter, H., et al., "Enhancer-Dependent Expression of Human Kappa Immunoglobulin Genes Introduced into Mouse Pre-B Lymphocytes by Electroporation", *Proc. Nat. Acad. Sci. USA, 81*, 7161-7165, (1984).

Prakash, C.S., et al., "High Efficiency Transformation and Regeneration of Transgenic Sweetpotato Plants", *In Vitro Cellular and Development Biology, 31*, Abstract No. W-17, 28A, (Mar. 1995).

Prioli, L.M., et al., "Plant Regeneration and Recovery of Fertile Plants from Protoplasts of Maize (Zea mays L)", *Bio/Technology, 7*, 589-594, (Jun. 1989).

Puite, K.J., et al., "Electrofusion a Simple and Reproducible Technique in Somatic Hybridization of Nicotiana plumbaginifolia mutants", *Plant Cell Rep., 4*, 274-276, (1985).

Ranch, J.P., et al., "Expression of 5-Methyltryptophan Resistance in Plants Regenerated from Resistant Cell Lines of Datura innoxia", *Plant Physiol., 71*, 136-140, (1983).

Randolph, L.F., et al., "Developmental Morphology of the Caryopsis in Maize", *Journal of Agricultural Research, 53*, 881-916, (Dec. 15, 1936).

Rasmussen, J.L., et al., "Biolistic Transformation of Tobacco and Maize Suspension Cells Using Bacterial Cells as Microprojectiles", *Plant Cell Rep., 13*, 212-217, (1994).

Rathinasabapathi, B., et al., "Metabolic engineering of glycine betaine synthesis: plant betaine aldehyde dehydrogenases lacking typical transit peptides are targeted to tobacco chloroplasts where they confer betaine aldehyde resistance", *Planta, 193*, 155-162, (1994).

Register III, J.C., et al., "Structure and Function of Selectable and Non-Selectable Transgenes in Maize after Introduction by Particle Bombardment", *Plant Molecular Biology, 25*, 951-961, (1994).

Rhodes, C.A., "Corn: From Protoplasts to Fertile Plants", *Bio/Technology, 7*, 548, (Jun. 1989).

Rhodes, C.A., et al., "Cytogenetic Stability of Aneuploid Maize Tissue Cultures", *Can. J. Genet. Cytol., 28*, 374-384, (1986).

Rhodes, C.A., et al., "Factors Affecting Tissue Culture Initiation from Maize Tassels", *Plant Science, 46*, 225-232, (1986).

Rhodes, C.A., et al., "Genetically Transformed Maize Plants from Protoplasts", *Science, 240*, 204-207, (Apr. 1988).

Rhodes, C.A., et al., "Plant Regeneration from Protoplasts Isolated from Embryogenic Maize Cell Cultures", *Bio/Technology, 6*, 56-60, (Jan. 1988).

Rice, J.A., et al., "Expression of Synthetic High Lysine Seed Storage Proteins can Significantly Increase the Accumulated Levels of Lysine in Mature Seeds of Transgenic Crop Plants", *Journal of Cellular Biochemistry*, vol. Suppl. O, No (18 part A), 107, (1994).

Rice, T.B., "Tissue Culture Induced Genetic Variation in Regenerated Maize Inbreds", *Proceedings of the 37th Annual Corn & Sorghum Industry Research Conference*, 148-162, (1982).

Richaud, F., et al., "Chromosomal Location and Nucleotide Sequence of the Escherichia coli dapA Gene", *Biol. Abstracts, 82*, Abstract No. 3396, p. 391, (1986).

Richaud, F., et al., "Chromosomal Location and Nucleotide Sequence of the Escherichia coli dapA Gene", *Journal of Bacteriology, 166*, 297-300, (Apr. 1986).

Robbins-Roth, C., et al., "They Make it Happen in Biotech", *Bioworld*, 30-36, (Nov.-Dec. 1990).

Robertson, D.S., "Loss of Mu Mutator Activity when Active Mu Systems are Transferred to Inbred Lines", *Maize Genetics Coop. Newsletter, 60*, 10, (1986).

Rosahl, S., et al., "Expression of a Tuber-Specific Protein In Transgenic Tobacco Plants: Demonstration Of An Esterase Activity", *EMBO. J, 6*, Press Limited, Oxford, England, 1155, (1987).

Ross, M., et al., "Manipulation of the Maize Meristem for Transformation", *In Vitro Cellular and Development Biology*, Program Issue, Congress on In Vitro Biology, Abstract No. P-1094, 72A, (May 20-24, 1995).

Ross, M.C., et al., "Transient and Stable Transgenic Cells and Calli of Tobacco and Maize Following Microprojectile Bombardment", *J. Cell. Biochem., 13D*, Abstract No. M149, p. 268, (1989).

Roth, B.A., et al., "C1- and R-Dependent Expression of the Maize Bz1 Gene Requires Sequences with Homology to Mammalian myb and myc Binding Sites", *The Plant Cell, 3*, 317-325, (Mar. 1991).

Roth, B.A., et al., "Genetic Regulation of Transient Expression of Maize Anthocyanin Pathway Genes Introduced into Intact Maize Tissues by Microprojectile Bombardment", *Journal of Cellular Biochemistry, 13D*, Abstract No. M 344, 310, (Mar. 27-Apr. 7, 1989).

Roush, R.T., et al., "Ecological Genetics of Insecticidal and Acaricide Resistance", *Ann. Rev. Entomol., 32*, 361-380, (1987).

Rout, J.R., et al., "Agrobacterium-Mediated Gene Transfer to Rice (Oryza sativa L.)", *In Vitro Cellular and Development Biology, 31*, Abstract No. W-19, 28A, (Mar. 1995).

Russell, J.A., et al., "Physical Trauma and Tungsten Toxicity Reduce the Efficiency of Biolistic Transformation", *Plant Physiol., 98*, 1050-1056, (1992).

Ryan, A.J., et al., "The Expression of the Napin Gene Under the Control of Its Own Promoter in Transgenic Tobacco Plants", *Journal of Cellular Biochemistry, 13D*, Abstract No. M 345, p. 310, (Mar. 27-Apr. 7, 1989).

Sahi, S.V., et al., "Metabolites in Maize Which Affect Virulence Induction in Agrobacterium tumefaciens", *Plant Physiol., Supplement*, Abstract No. 514, p. 86, (1989).

Saneoka, H., et al, "Salt tolerance of glycinebetaine-deficient and-containing maize lines1", *Plant Physiol.*, 107, pp. 631-638, (1995).

Sanford, J.C., "Biolistic Plant Transformation", *Physiol. Plant.,. 79*, 206-209, (1990).

Sanford, J.C., "The Biolistic Process", *Plant Physiology, 89*, Abstract No. 9, 2, (Apr. 1989).

Sanford, J.C., "The Biolistic Process", *Trends in Biotechnology, 6*, 299-302, (1988).

Sanford, J.C., et al., "Attempted Pollen-Mediated Plant Transformation Employing Genomic Donor DNA", *Theor. Appl. Genet., 69*, 571-574, (1985).

Sanford, J.C., et al., "Delivery of DNA into Regenerable Tissues of Monocots, Using High-Velocity Microprojectiles", Grant Application No. 86-0183, United States Department of Agriculture, Science and Education, 48 p., (Feb. 27, 1986).

Sanford, J.C., et al., "Delivery of Substances into Cells and Tissues Using a Particle Bombardment Process", *Particulates Sci. Technol., 5*, 27-37, (1987).

Sass, J.E., "Comparative Leaf Number in the Embryos of Some Types of Maize", *Iowa State Coll. J. Sci., 25*, 509-512, (1951).

Sass, J.E., "Morphology: Development of the Caryopsis", *In: Corn and Corn Improvement, Second Edition*, Sprague, G.F., (ed.), American Society of Agronomy, Inc., Madison, WI, p. 89, 98, (1977).

Schafer, W., et al., "T-DNA Integration and Expression in a Monocot Crop Plant after Induction of Agrobacterium", *Nature*, 327, 529-532, (Jun. 11, 1987).

Schardl, C.L., et al., "Design and Construction of a Versatile System for the Expression of Foreign Genes in Plants", *Gene*, 61, 1-11, (1987).

Schmidt, A., et al., "Media and Environmental Effects of Phenolics Production from Tobacco Cell Cultures", *Chem. Abstracts.*, 110, Abstract No. 230156z, p. 514, (1989).

Schnepf, H.E., et al., "Delineation of a Toxin-Encoding Segment of a Bacillus thuringiensis Crystal Protein Gene", *The Journal of Biological Chemistry*, 260, 6273-6280, (1985).

Schnepf, H.E., et al., "Specificity-Determining Regions of a Lepidopteran-Specific Insecticidal Protein Produced by Bacillus thuringiensis", *The Journal of Biological Chemistry*, 265, 20923-20930, (Dec. 5, 1990).

Scorza, R., et al., "Transformation of Grape (Vitis vinifera L.) Somatic Embryos and Regeneration of Transgenic Plants", *Journal of Cellular Biochemistry*, Supplement 18A, Abstract No. X1-310, 102, (Jan. 4-27, 1994).

Sewell, G.H., et al., "Irish Potato, Control of Potato-Eating Aphids, 1991", *Insecticidal and Acaricide Tests*: 1992, 17, 138, (1992).

Sewell, G.H., et al., "Transgenic Potato Plants, Control of Colorado Potato Beetle, 1991", *Insecticidal and Acaricide Test*: 1992, 17, 138-139, (1992).

Shaner, D.L., et al., "Mechanism of Action of the Imidazolinones and Cell Culture Selection of Tolerant Maize", *In: Biotechnology in Plant Sciences*, Zaitlin, M., et al., (eds.), Academic Press, Orlando, FL, 287-299, (1985).

Sharman, B.C., "Developmental Anatomy of the Shoot of Zea mays L.", *Annals of Botany*, VI, 246-281, (Apr. 1942).

Shatters, Jr., R.G., et al., "Particle Gun Bombardment of Embryogenic Bahiagrass Callus Culture", *Journal of Cellular Biochemistry*, Supplement 18A, Abstract No. X1-311, 102, (Jan. 4-23, 1994).

Shen, B., et al., "Partial Sequencing and Mapping of Clones from Two Maize cDNA Libraries", EMBL Sequence Data Library, Heidelberg, Germany, (Oct. 1, 1994).

Shen, B., et al., "Partial sequencing and mapping of clones from two maize cDNA libraries", *Plant Molecular Biology*, 26, 1085-1101, (1994).

Shen, W.H., et al., "Amplification and expression of the beta-glucuronidase gene in maize plants by vectors based on maize streak virus", *The Plant Journal*, 5, 227-236, (1994).

Shen, W.H., et al., "Excision of Transposible Element from a Viral Vector Introduced into Maize Plants by Agroinfection", *The Plant Journal*, 2, 35-42, (1992).

Shields, R., "Towards Insect-Resistant Plants", *Nature*, 328, 12-13, (Jul. 2, 1987).

Shigekawa, K., et al., "Electroporation of Eukaryotes and Prokaryotes: A General Approach to the Introduction of Macromolecules into Cells", *BioTechniques*, 6, 742-751, (1988).

Shillito, R.D., et al., "High Efficiency Direct Gene Transfer to Plants", *Bio/Technology*, 3, 1099-1103, (1985).

Shillito, R.D., et al., "Regeneration of Fertile Plants from Protoplasts of Elite Inbred Maize", *Bio/Technology*, 7, 581-587, (Jun. 1989).

Shimamoto, K., et al., "Fertile Transgenic Rice Plants Regenerated from Transformed Protoplasts", *Nature*, 338, 274-278, (1989).

Shivakumar, A.G., et al., "Vegetative Expression of the delta-Endotoxin Genes of Bacillus thuringiensis subsp. kurstaki in Bacillus subtilis", *Journal of Bacteriology*, 166, 194-204, (Apr. 1986).

Shorrosh, B.S., et al., "Molecular Cloning, Characterization, and Elicitation of Acetyl-CoA Carboxylase from Alfalfa", *Proc. Natl. Acad. Sci. USA*, 91, 4323-4327, (May 1994).

Shotwell, M.A., et al., "Analysis of Seed Storage Protein Genes of Oats", *The Journal of Biological Chemistry*, 265, 9652-9658, (Jun. 15, 1990).

Shotwell, M.A., et al., "The Biochemistry and Molecular Biology of Seed Storage Proteins", *In: The Biochemistry of Plants, vol. 15*, Marcus, A., (ed.), Academic Press, Inc., San Diego, CA, pp. 297-345, (1989).

Smith, G.E., et al., "Molecular Engineering of the Autographa californica Nuclear Polyhedrosis Virus Genome: Deletion Mutations Within the Polyhedrin Gene", *Journal of Virology*, 46, 584-593, (May 1983).

Smith, I.K., et al., "Properties and Functions of Glutathione Reductase in Plants", *Physiol. Plant.*, 77, 449-456, (1989).

Smith, R., et al., "Shoot Apex Explant for Transformation", *Plant Physiol. (Suppl.)*, 86, Abstract No. 646, p. 108, (1988).

Soberon, X., et al., "Construction and Characterization of New Cloning Vehicles. IV. Deletion Derivatives of pBR322 and pBR325", *Gene*, 9, 287-305, (1980).

Somers, D.A., et al., "Fertile, Transgenic Oat Plants", *Bio/Technology*, 10, 1589-1594, (Dec. 1992).

Somers, D.A., et al., "In Vitro Selection for Herbicide Tolerance in Maize", *Biotechnology in Agriculture and Forestry*, 25, Maize, Bajaj, Y.P.S., (ed.), 21 p., (1994).

Songstad, D.D., et al., "Transient Expression of GUS and Anthocyanin Constructs in Intact Maize Immature Embryos Following Electroporation", *Plant Cell Tissue and Organ Cuture*, 33, 195-201, (1993).

Sorenson, K.A., et al., "Colorado Potato Beetle Control with Bioinsecticides, 1991", *Insecticide and Acaricide Tests*: 1992, 17, 139, (1992).

Spangenberg, G., et al., "Gene Transfer and Regeneration of Trangenic Plants in Forage Grasses", *Journal of Cellular Biochemistry, Supplement 18A*, Abstract No. X1-312, p. 102, (Jan. 4-23, 1994).

Spencer, T.M., et al., "Bialaphos Selection of Stable Transformations from Maize Cell Culture", *Theor. Appl. Genet.*, 79, 625-631, (May 1990).

Spencer, T.M., et al., "Characterization of Transgene Insertion and Expression in a Glufosinate-Resistant Maize Line", *In Vitro Cellular and Developmental Biology*, 31, Program Issue, Congress on In Vitro Biology, Abstract No. P-1096, 72A, (May 20-24, 1995).

Spencer, T.M., et al., "Fertile Transgenic Maize", Abstracts, 7th Annual Meeting of the Mid-Atlantic Plant Molecular Biology Society, University of Maryland, College Park, MD, p. 30, (Aug. 16-17, 1990).

Spencer, T.M., et al., "Production of Fertile Transgenic Maize by Electroporation", *In Vitro Cellular and Developmental Biology*, Program Issue, Congress on Tissue and Cell Culture, Abstract No. P-11, 34, (Jun. 4-7, 1994).

Spencer, T.M., et al., "Segregation of Transgenes in Maize", *Plant Mol. Biol.*, 18, 201-210, (1992).

Spencer, T.M., et al., "Selection of Stable Transformants from Maize Suspension Cultures using the Herbicide Bialaphos", Poster Presentation, FASEB Plant Gene Expression Conference, Copper Mountain, CO, (Aug. 6-11, 1989).

Sprague, G.M., et al., "Corn Breeding", *In: Corn and Corn Improvement, Second Edition*, Sprague, G.F., (ed.), American Society of Agronomy, Inc., Madison, WI, p. 305, 320-323, (1977).

St. Julian, G., et al., "Bacteria, Spirochetes, and Rickettsia as Insecticies", *Annals of the New York Academy of Sciences*, 217, 65-75, (1973).

Strauch, E., et al, "Cloning of a Phosphinothricin N-Acetyltransferase Gene from Streptomyces Viridochromogenes Tu494 and its Expression in *Streptomyces lividans* and *Escherichia coli*", *Gene*, 63, 65-74, (1988).

Stark, D.M., et al., "Regulation of the Amount of Starch in Plant Tissues by ADP Glucose Pyrophosphorylase", *Science*, 258, 287-291, (Oct. 9, 1992).

Steimel, D., "Corn Breeders Stalk Perfect Hybrid", *Rockford Register Star*, (Aug. 6, 1990).

Sugiyama, M., et al., "Use of the Tyrosinase Gene from Streptomyces to Probe Promoter Sequences for *Escherichia coli*", *Plasmid*, 23, 237-241, (1990).

Stolle, C.A., et al., "Cellular Factor Affecting the Stability of beta-globulin mRNA", *Gene*, 62, 65-74, (1988).

Stougaard, J., "Substrate-Dependent Negative Selection in Plants Using a Bacterial Cytosine Deaminase Gene", *The Plant Journal*, 3, 755-761, (1993).

Strauch, E., et al, "Cloning of a Phosphinothricin N-Acetyltransferase Gene from Streptomyces Viridochromogenes Tu494 and its Expression in Streptomyces lividans and Escherichia coli", *Gene*, 63, 65-74, (1988).

Stroo, H.F., et al., "Heterotrophic Nitrification in an Acid Forest Soil and by an Acid-Tolerant Fungus", *Applied and Environmental Microbiology*, 52, 1107-111, (Nov. 1986).

Sugiyama, M., et al., "Use of the Tyrosinase Gene from Streptomyces to Probe Promoter Sequences for Escherichia coli", *Plasmid*, 23, 237-241, (1990).

Sukhapinda, K., et al., "Maize Haploid Protoplast Transformation and Regeneration of Transgenic Plants", *In Vitro Cellular and Developmental Biology*, 28, Abstract No. P-1132, p. 123A, (Mar. 1992).

Suprasanna, P., et al., "Plantlet Regeneration from Glume Calli of Maize (*Zea mays* L.)", *Theor. Appl. Genet.*, 72, 120-122, (1986).

Suttie, J., et al., "Use of Different Selection Agents to Produce Maize Transformants of an Elite Genotype Using Microprojectile Bombardment", *Program and Abstracts, International Society for Plant Molecular Biology, Third International Congress*, Tucson, AZ, Abstract No. 426, (Oct. 6-11, 1991).

Tarczynski, M.C., et al, "Expression of a Bacterial mtlD Gene in Transgenic Tobacco Leads to Production and Accumulation of Mannitol", *Proc. Natl. Acad. Sci. USA*, 89, 2600-2604, (1992).

Tarczynski, M.C., et al., "Stress Protection of Transgenic Tobacco by Production of the Osmolyte Mannitol", *Science*, 259, 508-510, (1993).

Teeri, T.H., et al., "Mendelian Inheritance of Transgenes in Barley", *Journal of Cellular Biochemistry, Supplemental 18A*, Abstract No. X1-313, p. 102, (Jan. 4-23, 1994).

Thomas, W.E., et al., "Mechanism of Action of Bacillus thuringiensis var israelensis Insecticidal Delta-Endotoxin", *FEBS Letters* 154, 362-368, (Apr. 1983).

Thompson, C.J., et al., "Characterization of the Herbicide-Resistance Gene bar from *Streptomyces hygroscopicus*", *EMBO Journal*, 6, 2519-2523, (1987).

Tojo, A., et al., "Dissolution and Degradation of Bacillus thuringiensis Delta-Endotoxin by Gut Juice Protease of the Silkworm Bombyx mori", *Applied and Environmental Microbiology*, 45, 576-580, (Feb. 1983).

Tomes, D.T., "Cell Culture, Somatic Embryogenesis and Plant Regeneration in Maize, Rice, Sorghum and Millets", *In: Cereal Tissue and Cell Culture*, Bright, S.W.J., et al., (eds.), Martinus Nijnoff/Dr. W. Junk, Amsterdam, The Netherlands, 175-203, (1985).

Tomes, D.T., "Initiation of Embryogenic Callus Cultures from Immature Embryos of Elite Corn (*Zea mays* L.) Germplasm", *In Vitro*, 20, Abstract No. 145, p. 276, (Mar. 1984).

Tomes, D.T., "Status of Corn Transformation", 26th Annual Corn Breeders School, Meeting Proceedings, University of Illinois, Champaign, IL, p. 7-8, (Feb. 26-27, 1990).

Tomes, D.T., et al., "The Effect of Parental Genotype on Initiation of Embryogenic Callus from Elite Maize (*Zea mays* L.) Germplasm", *Theor. Appl. Genet.*, 70, 505-509, (1985).

Tomes, D.T., et al., "Transgenic Tobacco Plants and Their Progeny Derived by Microprojectile Bombardment of Tobacco Leaves", *Plant Mol. Biol.*, 14, 261-268, (Feb. 1990).

Torne, J.M., et al., "Regeneration of Plants from Mesocotyl Tissue Cultures of Immature Embryos of *Zea mays* L.", *Plant Science Letters*, 17. 339-344, (1980).

Twell, D., et al., "Transient Expression of Chimeric Genes Delivered into Pollen by Microprojectile Bombardment", *Plant Physiol.*, 91, 1271-1274, (1989).

Ulian, et al., "Transformation of Plants via the Shoot Apex", *In Vitro Cell. Dev. Biol.*, 9, 951-954, (1988).

Usami, S., et al., "Absence in Monocotyledonous Plants of the Diffusible Plant Factors inducing T-DNA Circularization and vir Gene Expression in Agrobacterium", *Mol. Gen. Genet.*, 209, 221-226, (1987).

Vaeck, M., et al, "Bacillus thuringiensis Endotoxin Gene Expression and Insect Resistance in Higher Plants", *Pesticide Science*, 20, 319-320, (1987).

Vaeck, M., et al., "Engineering Improved Crops for Agriculture: Protection from Insects and Resistance to Herbicides", *In: Plant Gene Systems and Their Biology*, Key, J.L., et al., (eds.), Alan R. Liss, Inc., New York, 171-181, (1987).

Vaeck, M., et al., "Engineering of Insect Resistant Plants Using a B. thruringiensis Gene", *In: Molecular Strategies for Crop Protection*, New York, Alan R. Liss, Inc., 355-366, (1987).

Vaeck, M., et al. "Insect Resistance in Transgenic Plants Expressing *Bacillus thuringeinsis* Toxin Gens", *An. Soc. Entomol. Brasil*, 16, 427-435, (1987).

Vaeck, M., et al., "Protein Engineering in Plants: Expression of *Bacillus thuringiensis* Insecticidal Protein Genes", *Cell Culture and Somatic Cell Genetics of Plants*, 6, 425-439, (1989).

Vaeck, M., et al., "Transgenic Plants Protected from Insect Attack", *Nature*, 328, 33-37, (Jul. 2, 1987).

Vain, P., et al., "Osmotic Pretreatment Enhances Particle Bombardment-Mediated Transient and Stable Transformation of Maize", *Plant Cell Rep.*, 12, 84-88, (1993).

van den Elzen, P.J., et al., "A Chimaeric Hygromycin Resistance Gene as a Selectable Marker in Plant Cells", *Plant Molecular Biology*, 5, 299-302, (1985).

van den Elzen, P.J., et al., "Simple Binary Vectors for DNA Transfer to Plant Cells", *Plant Molecular Biology*, 5, 149-154, (1985).

Van Lammeren, A.A., "Developmental Morphology and Cytology of the Young Maize Embryo (*Zea mays* L.)", *Acta Bot. Neerl.*, 35, 169-188, (Aug. 1986).

Vasil, I.K., "Isolation and Culture of Protoplasts of Grasses", *International Review of Cytology, Supplement*, 16, Bourne, G.H., et al., (eds.), Academic Press, New York, 79-88, (1983).

Vasil, I.K., "Molecular Improvement of Cereals", *Plant Molecular Biology*, 258, 925-937, (1994).

Vasil, I.K., "Transgenic Cereals Becoming a Reality", *Bio/Technology*, 8, 797, (Sep. 1990).

Vasil, I.K., et al., "Culture of Protoplasts Isolated from Embryogenic Cell Suspension Cultures of Sugarcane and Maize", *IAPTC Abstracts*, p. 443, (1986).

Vasil, I.K., et al., "Molecular Genetic Improvement of Wheat", *Journal of Cellular Biochemistry*, Supplement 18A, Abstract No. X1-015, 78, (Jan. 4-23, 1994).

Vasil, V., et al., "Histology of Somatic Embryogenesis in Cultured Immature Embryos of Maize (*Zea mays* L.)", *Protoplasma*, 127, 1-8, (1985).

Vasil, V., et al., "Isolation and Maintenance of Embryogenic Cell Suspension Cultures of Gramineae", *In: Cell Culture and Somatic Cell Genetics of Plants*l, vol. I. Academic Press, pp. 152-158, (1984).

Vasil, V., et al., "Plant Regeneration from Friable Embryonic Callus and Cell Suspension Cultures of *Zea mays* L.", *J. Plant Physiol.*, 124, 399-408, (1986).

Vasil, V., et al. "Regeneration of Plants from Embryogenic Suspension Culture Protoplasts of Wheat (*Triticum aestivum* L.)", *Bio/Technology*, 8, 429-434, (May 1990).

Vernon, D.M., et al., "A Novel Methyl Transferase Induced by Osmotic Stress in the Facultative Halophyte Mesembryanthemum crystallinum", *The EMBO Journal*, 11, 2077-2085, (1992).

Viotti, A., et al., "Each Zein Gene Class Can Produce Polypeptides of Different Sizes", *The EMBO J.*, 4, 1103-1110, (1985).

Visser, B., et al., "Transgenic Tobacco Plants Expressing a Modified *Bacillus thuringiensis* cryIC Gene", *Journal of Cellular Biochemistry*, Supplement 16F, Abstract No. Y 136, p. (Apr. 3-16, 1992).

Walbot, V., et al., "Molecular Genetics of Corn", *In: Corn and Corn Improvement, Third Edition*, Sprague, G.F., et al., (eds.), American Society of Agronomy, Inc., Madison, WI, p. 389-430, (1988).

Waldron, C., et al., "Resistance to Hygromycin B", *Plant Mol. Biol.*, 5, 103-108, (1985).

Walter, D.A., et al., "Transformation and Inheritance of Hygromycin Phosphotransferase Gene in Maize Plants", *Plant Mol. Biol.*, 18, 189-200, (1992).

Wan, Y., et al., "Development and Use of and Efficient Transformation Sytem for Barley", *Journal of Cellular Biochemistry*, Supplement 18A, Abstract No. X1-013, 78, (Jan. 4-23, 1994).

Wan, Y., et al., "Efficient Production of Transgenic Barley Plants and Analysis of Transgene Expression in Progeny", *In Vitro Cellular and Development Biology*, 30A, Program Issue Congress on Cell and Tissue Culture, Abstract P-10, 34, (Jun. 4-7, 1994).

Wan, Y., et al., "Generation of Large Numbers of Independently Transformed Fertile Barley Plants", *Plant Physiol.*, 104, 37-48, (1994).

Weissinger, A., et al., "Microprojectile Bombardment for Maize Transformation", *In Vitro Cellular and Developmental Biology*, 23, Program Issue, 38th Annual Meeting of the Tissue Culture Association, Washington, D.C., Abstract No. 254, (Mar. 1987).

Wernicke, W., et al., "Adventitious Embryoid and Root Formation from Rice Leaves", *Z. Pflanzenphysiol. Bd.*, 103, 361-365, (1981).

Werr, W., et al., "Structure of the Sucrose Synthase Gene on Chromosome 9 of *Zea mays* L.", *The EMBO Journal*, 4, 1373-1380, (1985).

White, D.W., et al., "Auxin-Inductible Response Promoter Elements", *Journal of Cellular Biochemistry*, Supplement 16F, Abstract No. Y 138, 213, (Apr. 3-16, 1992).

White, J., et al., "A Cassette Containing the bar Gene of Streptomyces hygroscopicus: a Selectable Marker for Plant Transformation", *Nuc. Acids Res.*, 18, 1062, (1989).

Whitely, H.R., et al., "The Molecular Biology of Parasporal Crystal Body Formation in Bacillus thuringiensis", *Ann. Rev. Microbiol.*, 40, 549-576, (1986).

Williams, R., et al., "Expression of the Maize Homeobox Gene Knotted-1 in Transgenic Maize", *Abstracts, 35th Annual Maize Genetics Conference*, St. Charles, IL, Poster No. 47, p. 46, (Mar. 18-21, 1993).

Williams, S., et al., "Chemical Regulation of *Bacillus thuringiensis* delta-Endotoxin Expression in Transgenic Plants", *Bio/technology*, 10, 540-543, (May 1992).

Wilson, F.D., et al., "Resistance of Cotton Lines Containing a *Bacillus thuringiensis* Toxin to Pink Bollworm (Lepidoptera: Gelechiidae) and Other Insects", *J. Econ. Entomol.*, 85, 1516-1521, (1992).

Wilson, H.M., et al., "Maize", *In: Transformation of Plants and Soil Microorganisms*, Wang, K., et al., (eds.), Cambridge University Press, New York, 65-80, (1995).

Withers, L., et al., "Proline: A Novel Cryoprotectant for the Freeze Preservation of Cultured Cells of *Zea mays* L.", *Plant Physiology*, 64, 675-678, (1979).

Wan, Y., et al., "Maize Transformation and Regeneration of Transgenic Plants by Microprojectile Bombardment of Type I Callus", *Abstracts, 35th Annual Maize Genetics Conference*, St. Charles, IL, p. 5, (Mar. 18-21, 1993).

Wan, Y., et al., "Type 1 Callus as a Bombardment Target for Generating Fertile Transgenic Maize (*Zea mays* L.)", *Planta*, 196, 7-14, (1995).

Wang, Y., et al., "Characteriazation of cis-Acting Elements Regulating Transcription from the Promoter of a Constitutively Active Rice Actin Gene", *Mol. Cell. Biol.*, 12, 3399-3406, (1992).

Wang, Y.C., et al., "Transient Expression of Foreign Genes in Rice, Wheat and Soybean Cells Following Particle Bombardment", *Plant Molecular Biology*, 11, 433-439, (1988).

Warren, G.W., et al., "Field Evaluation of Transgenic Tobacco Containing a *Bacillus thuringiensis* Insecticidal Protein Gene", *Journal of Economic Entomology*, 85, 1651-1659, (1992).

Watson, S.A., "Corn Marketing, Processing and Utilization", *In: Corn and Corn Improvement, 3rd Edition*, Sprague, G.F., et al., (eds.), American Society of Agronomy, Inc., et al., Madison, WI, 881-939, (1988).

Webb, R.P., et al., "Superoxide Dismutase Gene Expression in Transgenic Plants", *Journal of Cellular Biochemistry*, Supplement 16f, Abstract No. Y 137-213, (Apr. 3-16, 1992).

Weck, E., "Are Colorized DNA Sequences and Application of Fuzzy Logic?", *Abstracts, 35th Annual Maize Genetics Conference*, St. Charles, IL, Poster No. 45, p. 45, (Mar. 18-21, 1993).

Weeks, J.T., et al., "Rapid Production of Multiple Independent Lines of Fertile Transgenic Wheat (Triticum aestivum)", *Plant Physiol.*, 102, 1077-1084, (1993).

Weigel, Jr., et al., "Somatic Embryogenesis in Barley", *In Vitro*, 20, Abstract No. 147, p. 277, (Mar. 1984).

Weising, K., et al., "Foreign Genes in Plants: Transfer, Structure, Expression and Applications", *Ann. Rev. Genet.*, 22, 421-478, (1988).

Weissinger, A., et al., "Maize Transformation via Microprojectile Bombardment", *In: Genetic Improvements of Agriculturally Important Crops*, Fraley, R.T., et al., (eds.), Cold Spring Harbor Laboratory, Cold Spring Harbor, NY, 21-25, (1988).

Witt, D.P., et al., "Cytotoxicity of Bacillus thuringiensis Delta-Endotoxins to Cultured Cf-1 Cells Does Not Correlate with In Vivo Activity Toward Spruce Budworm Larvae", *In: Fundamental and Applied Aspects of Invertebrate Pathology*, Samson, R.A., et al., (eds.), Fourth International Colloquium of Invertebrate Pathology, Wangingen, The Netherlands, 3-6, (Aug. 18-22, 1986).

Wohlleben, W., et al., "Nucleotide Sequence of the Phosphinothricin N-Acetyltransferase Gene from Streptomyces viridochromogenes Tu494 and Its Expression in Nicotania tabacum", *Gene*, 70, 25-37, (1988).

Wolter, F.P., et al., "Chilling Sensitivity of *Arabidopsis thaliana* with Genetically Engineered Membrane Lipids", *The EMBO Journal*, 11, 4685-4692, (1992).

Wong, E.Y., et al., "*Arabidopsis thaliana* Small Subunit Leader and Transit Peptide Enhance the Expression of Bacillus thuringiensis Proteins in Transgenic Plants", *Plant Mol. Biol.*, 20, 81-93, (1992).

Wong, J.R., et al., "Anthocyanin Regulatory Genes from Maize (B-Peru and C1) Activate the Anthocyanin Pathway in Wheat, Barley and Oat Cells", *Journal of Cellular Biochemistry, Supplement 15A*, 159, (1991).

Wood, M., "Blast Those Genes!", *Agricultural Research*, 2 p., (Jun. 1989).

Wu, S., et al., "Characterization of Chitinase cDNA Clones for Acidic and Basic Isoforms of Maize", *Abstracts, 35th Annual Maize Genetics Conference*, St. Charles, IL, Poster No. 48, p. 46, (Mar. 18-21, 1993).

Wyatt, S.D., et al., "Coat Protein Gene-Mediated Resistance to Barley Yellow Dwarf Virus in Maize and Barley", *Phytopathology*, 83, Abstract No. A392, 1374, (Dec. 1993).

Xiang, C., et al., "The Anti-nptII Gene—A Potential Negative Selectable Marker for Plants", *Plant Physiol.*, 102, 287-293, (1993).

Xiayi, K., et al., "Electroporation of Immature Maize Zygotic Embryos and Regeneration of Transgenic Plants", *Transgenic Research*, 5, 219-221, (1996).

Xue, Q., et al., "Genotypic Variation in Osmotic Adjustment Among Closely Related Wheat Lines", *Agronomy Abstracts*, 1995 Annual Meetings, St. Louis, MO, p. 78, (Oct. 29-Nov. 3, 1995).

Yamaguchi-Shinozaki, K., et al., "Molecular Cloning and Characterization of 9 cDNAs for Genes that are Responsive to Desiccation in Arabidopsis thaliana: Sequence Analysis of One cDNA Clone that Encodes a Putative Transmembrane Channel Protein", *Plant Cell Physiol.*, 33, 217-224, (1992).

Yang, H., et al., "Production of Kanamycin Resistant Rice Tissues Following DNA Uptake into Protoplasts", *Plant Cell Rep.*, 7, 421-425, (1988).

Yang, N.S., et al., "Maize Sucrose Synthase-1 Promoter Directs Phloem Cell-Specific Expression of Gus Gene in Transgenic Tobacco Plants", *Proc. Natl. Acad. Sci. USA*, 87, 4144-4148, (Jun. 1990).

Yanisch-Perron, C., et al., "Improved M13 Phage Cloning Vectors and Host Strains: Nucleotide Sequences of the M13mp18 and pUC19 Vectors", *Gene*, 33, 103-119, (1985).

Yenofsky, R.L., et al., "Isolation and Characterization of a Soybean (Glycine max) Lipoxygenase-3 Gene", *Mol. Gen. Genet.*, 211, 215-222, (1988).

Yoshiba, Y., et al., "Correlation Between the Induction of a Gene For Deltal-Pyrroline-5-Carboxylate Synthetase and the Accumulation of Proline in Arabidopsis thaliana Under Osmotic Stress", *The Plant Journal*, 7, 751-760, (1995).

Yugari, Y., et al., "Coordinated End-Product Inhibition in Lysine Synthesis in *Escherichia coli*", *Biochem. Biophys. Acta*, 62, 612-614, (1962).

Zhang, W., et al., "Analysis of Rice ActI 5' Region Activity in Transgenic Rice Plants and the Study of Regulatory Elements in This Region", *Journal of Cellular Biochemistry*, Supplement 16F, Abstract No. Y 139, p. 213, (Apr. 3-16, 1992).

* cited by examiner

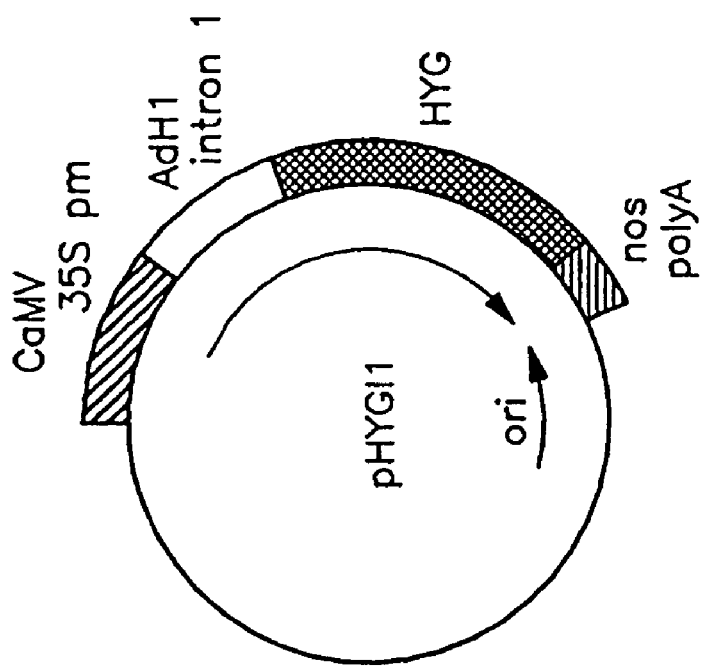
FIG. 1A
FIG. 1B

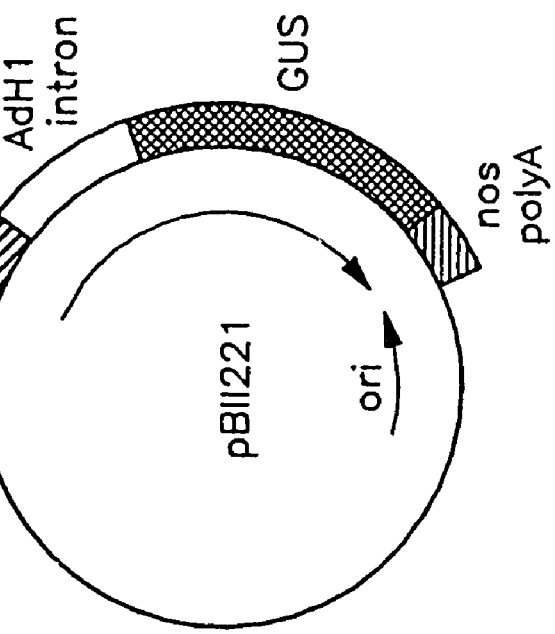
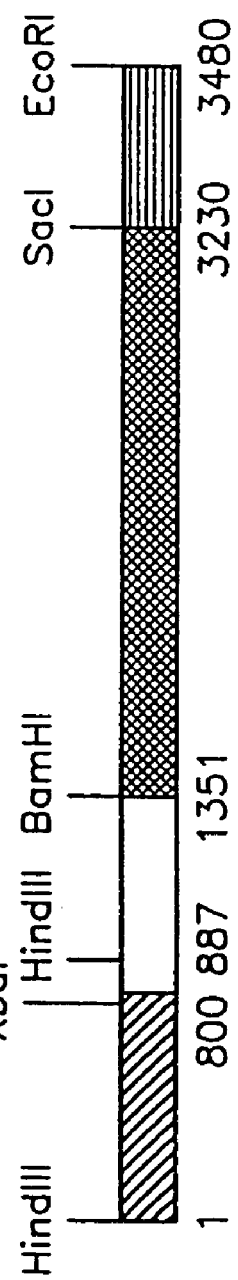
FIG. 2A
FIG. 2B

PHI CALLUS

PHI R₀ PLANTS

PH2 CALLUS

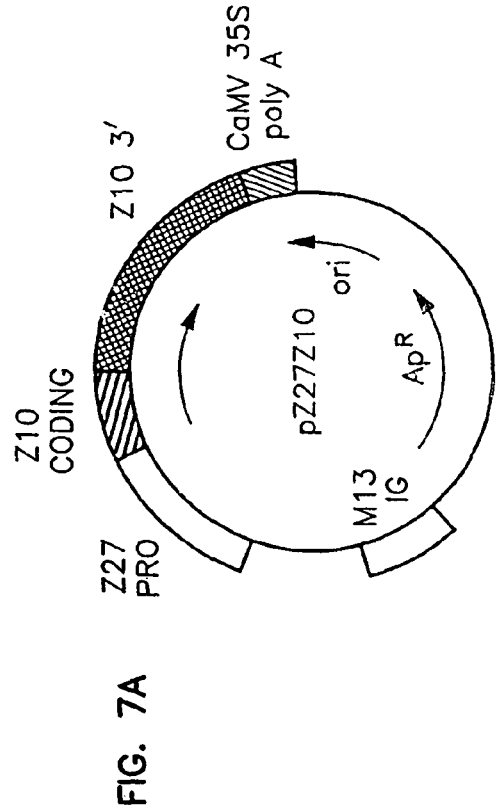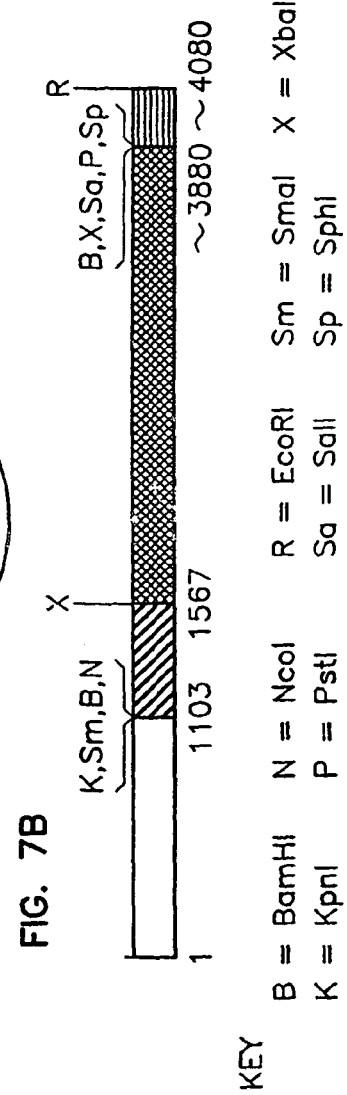
FIG. 7A
FIG. 7B
KEY
B = BamHI   N = NcoI   R = EcoRI   Sm = SmaI   X = XbaI
K = KpnI    P = PstI   Sa = SalI   Sp = SphI

METHOD OF PREPARING FERTILE TRANSGENIC CORN PLANTS BY MICROPROJECTILE BOMBARDMENT

CROSS REFERENCE TO RELATED APPLICATION

This Application is a divisional of U.S. patent application Ser. No. 08/619,077, filed Mar. 20, 1996, now U.S. Pat. No. 6,331,665; which is in turn a divisional of Ser. No. 08/285,488, filed Aug. 3, 1994, now U.S. Pat. No. 5,508,468; which is in turn a continuation of Ser. No. 07/636,089, filed Dec. 28, 1990, abandoned; which in turn is a continuation-in-part of Ser. No. 07/508,045, filed Apr. 11, 1990, U.S. Pat. No. 5,484,956; which is in turn a continuation in part of Ser. No. 07/467,983, filed Jan. 22, 1990, abandoned; and this application is also a continuation-in-part of U.S. patent application Ser. No. 08/677,695, filed Jul. 10, 1996.

FIELD OF THE INVENTION

This invention relates to fertile transgenic plants of the species *Zea mays* (oftentimes referred to herein as maize or corn). The invention further relates to producing fertile transgenic plants via particle bombardment and subsequent selection techniques.

BACKGROUND OF THE INVENTION

Genetic engineering of plants, which entails the isolation and manipulation of genetic material (usually in the form of DNA or RNA) and the subsequent introduction of that genetic material into a plant or plant cells, offers considerable promise to modern agriculture and plant breeding. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Once a gene has been identified, cloned, and engineered, it is still necessary to introduce it into a plant of interest in such a manner that the resulting plant is both fertile and capable of passing the gene on to its progeny.

A variety of methods have been developed and are currently available for the transformation of various plants and plant cells with DNA. Generally, these plants have been dicotyledonous, and some success has been reported with certain of the monocotyledonous cereals. However, some species have heretofore proven untransformable by any method. Thus, previous to this discovery, no technology had been developed which would permit the production of stably transformed *Zea mays* plants in which the introduced recombinant DNA is transmitted through at least one complete sexual cycle. This failure in the art is well documented in the literature and has been discussed in a number of recent reviews (I. Potrykus, *Trends in Biotechnology*, 7, 269 (1989); K. Weising et al., *Ann. Rev. of Genetics*, 22, 421 (1988); F. Cocking et al., *Science*, 236, 1259 (1987)).

Some of the techniques attempted, or proposed, for introducing DNA into corn cells include electroporation, microinjection, microprojectile bombardment, liposome fusion, *Agrobacterium*-mediated transfer, macroinjection, and exposure to naked DNA in solution.

For example, J. DeWet et al., *Experimental Manipulation of Ovule Tissue*, G. Chapman et al., eds., Longman, Inc., New York (1985) at pages 197–269 and Y. Ohta, *PNAS USA*, 83, 715 (1986) reported the introduction of DNA into maize by mixing pollen grains with DNA solutions, and applying the pollen to maize silks. In these papers, there is no molecular data confirming the introduction of the exogenous DNA into the corn cells. Arntzen et al. in published European Patent Application No. 275,069 describe the incubation of DNA with maize pollen followed by pollination of maize ears and formation of seeds. The plants derived from these seeds were reported to contain the introduced DNA, but there is no suggestion that the introduced DNA was transmitted through a complete sexual cycle.

A. Graves et al., *Plant Mol. Biol.*, 3, 43 (1986) reported *Agrobacterium*-mediated transformation of *Zea mays* seedlings. The evidence was based upon assays which can sometimes be unreliable. To date, there have been no further reported successes with pollen and *Agrobacterium*-mediated transfer techniques.

Microprojectile bombardment has been reported to yield transformed corn cells. The technique is disclosed in Sanford et al., *Part. Sci. & Techn.*, 5, 27 (1987) as well as in published European patent application number 331,855 of J. C. Sanford et al. which is based upon U.S. Ser. No. 07/161,807, filed Feb. 29, 1988. Klein et al., *Plant Physiol.*, 91, 440 (1989) describe production of transformed corn cells, using microprojectile bombardment. However, the cells used were not capable of regeneration into plants. Thus, no protocols have been published describing the introduction of DNA by a bombardment technique into cultures of regenerable maize cells of any type. No stable introduction of a gene has been reported that results from bombardment of maize callus followed by regeneration fertile plants and transmission of the introduced gene through at least one sexual cycle. D. McCabe et al., in published European patent application No. 270,356, disclose the bombardment of maize pollen with DNA, the application of the pollen to silks, and the formation of seeds which reportedly contain the exogenous DNA. However, there is no evidence that the DNA was transmitted through a complete sexual cycle, and no further results have been reported by this group.

Electroporation of corn protoplasts has been reported to result in transformed cells by M. E. Fromm et al., *Nature*, 319, 791 (1986) although these cells did not provide regenerated plants. Electroporation of corn protoplasts was also reported by C. Rhodes et al., *Science*, 240, 204 (1988). Although the recipient cells were transformed and, in the latter case, were able to regenerate into plants, the plants themselves were sterile. In addition, methods for the production of the cell line used by Rhodes et al. were not reproducible.

A further stumbling block to the successful production of fertile transgenic maize plants has been in selecting those few transformants in such a manner that neither the regeneration capacity (in the case of protoplasts or cell cultures) nor the fertility of the transformants are destroyed. Due to the generally low level of transformants produced by a transformation technique, some sort of selection procedure is often necessary. However, selection generally entails the use of some toxic agent, e.g., a herbicide or antibiotic, which may be detrimental to either the regenerability or the resultant plant fertility.

On the other hand, it has been known that untransformed corn protoplasts, cultured cells and callus at least can be regenerated to form mature plants and that the resulting plants are often fertile. For example, R. D. Shillito et al., *Bio/Technology*, 7, 581 (1989), and L. M. Prioli et al., *Bio/Technology*, 7, 589 (1989) discuss methods for producing protoplasts from cell cultures and recovering fertile plants therefrom. C. A. Rhodes et al., *Bio/Technology*, 6, 56 (1988) disclose attempts to regenerate maize plants from protoplasts isolated from embryogenic maize cell cultures.

However, it has not been possible for the art worker to determine which maize tissues or cultures are appropriate recipients for exogenous DNA, e.g., contain a useful number of cells which are receptive to and which will stably integrate the exogenous DNA, and at the same time be a part of the germline, i.e., part of the cell lineage that leads to the next plant generation.

The art is thus faced with a dilemma. While certain transformation techniques have been proposed or reported to produce transformed maize cells and certain cells and tissues have been proposed to be potential recipients due to their ability to regenerate plants, the art has failed to find a combination of techniques which would successfully produce transformed maize plants able to transmit the introduced DNA through one complete sexual cycle.

It is thus an object of the present invention to produce fertile, stably-transgenic, *Zea mays* plants and seeds which transmit the introduced gene to progeny. It is a further object to produce such stably-transgenic plants and seeds by a particle bombardment and a selection process which results in a high level of viability for at least a portion of the transformed cells. It is a further object to produce fertile, stably-transgenic plants of other graminaceous cereals besides maize.

REFERENCES CITED

The references listed below are incorporated by reference herein.

Armstrong, C L, et al. (1985) Planta 164:207–214
Callis, J, et al. (1987) Genes & Develop 1:1183–1200
M. Bevan et al. (1983) Nuc Acids Res 11:36a
Chu, C C, et al. (1975) Sci Sin (Peking) 18:659–668
Cocking, F, et al. (1987) Science 236:1259–1262
DeWet et al. (1985) Proc Natl Sci USA 82:7870–7873
Freeling, J C, et al. (1976) Maydica XXI:97–112
Graves, A, et al. (1986) Plant Mol Biol 7:43–50
Green, C, et al. (1975) Crop Sci 15:417–421
Green, C, et al. (1982) Maize for Biological Research, Plant Mol. Biol. Assoc., pp 367–372
Gritz, L, et al. (1983) Gene 25:179–188
Guilley, H, et al. (1982) Cell 30:763–773
Hallauer, A R, et al. (1988) Corn and Corn Improvement, 3rd ed., Agronomy Society of America, pp 469–564
Jefferson, R, et al. (1987) EMBO J 6:3901–3907
Kamo, K, et al. (1985) Bot Gaz 146:327–334
Klein, T, et al. (1989) Plant Physiol 91:440–444
Klein, T, et al. (1988a) Proc Natl Acad Sci USA 85:4305–9
Klein, T, et al. (1988b) Bio/Technology 6:559–563
Lu, C, et al. (1982) Theor Appl Genet 62:109–112
McCabe, D, et al. (1988) Bio/Technology 6:923–926
Murashige, T, et al. (1962) Physiol Plant 15:473–497
Neuffer, M, (1982) Maize for Biological Research, Plant Mol Biol Assoc, pp 19–30
Phillips, R, et al. (1988) Corn and Corn Improvement, 3rd ed., Agronomy Society of America, pp 345–387
Potrykus, I (1989) Trends in Biotechnology 7:269–273
Rhodes, C A, et al. (1988) Science 240:204–7
Sambrook, J, et al. (1989) Molecular Cloning: A Laboratory Manual, 2nd ed., Cold Spring Harbor Laboratory Press
Sanford, J, et al. (1987) Part Sci & Techn 5:27–37
Weising, K, et al., (1988) Ann Rev of Genetics 22:421–478
Yanisch-Perron, L, et al. (1985) Gene 33:109–119

SUMMARY OF THE INVENTION

The present invention relates to fertile transgenic *Zea mays* plants containing recombinant DNA, preferably chromosomally integrated recombinant DNA, which is heritable by progeny thereof.

The invention further relates to all products derived from transgenic *Zea mays* plants, plant cells, plant parts, and seeds.

The invention further relates to transgenic *Zea mays* seeds stably containing recombinant DNA and progeny which have inherited the recombinant DNA. The invention further relates to the breeding of transgenic plants and the subsequent incorporation of recombinant DNA into any *Zea mays* plant or line.

The invention further relates to a process for producing fertile transgenic *Zea mays* plants containing recombinant DNA. The process is based upon microprojectile bombardment, selection, plant regeneration, and conventional backcrossing techniques.

The invention further relates to a process for producing fertile transformed plants of graminaceous species other than *Zea mays* which have not been reliably transformed by traditional methods such as electroporation, *Agrobacterium*, injection, and previous ballistic techniques.

The invention further relates to regenerated fertile mature maize plants obtained from transformed embryogenic tissue, transgenic seeds produced therefrom, and R1 and subsequent generations.

A preferred embodiment of the present invention is a fertile, transgenic corn plant that has been stably transformed with a recombinant, chimeric gene which is expressed as a seed storage protein, e.g., as the 10 kD zein protein, so that the level of at least one amino acid is elevated above that present in the parent, nontransformed lines. Expression of multiple copies of said gene or overexpression thereof, can substantially increase the whole kernel levels of certain amino acids, such as lysine, methionine, threonine and the like. As used herein, the term "substantially increased" means that the level of a given amino acid is at least 10–20% above that present in the corresponding plant or plant part which has not been transformed with said seed storage protein gene.

In preferred embodiments, this invention produces the fertile, transgenic plants by means of a recombinant DNA-coated microprojectile bombardment of clumps of friable embryogenic callus, followed by a controlled regimen for selection of transformed callus lines.

BRIEF DESCRIPTION OF THE DRAWINGS

FIG. 1A shows a map of plasmid vector pHYGI1 utilized in Example I. FIG. 1B shows the relevant part of linearized pHYGI1 encompassing the HPT coding sequence and associated regulatory elements. The base pair numbers start from the 5' nucleotide in the recognition sequence for the indicated restriction enzymes, beginning with the EcoRI site at the 5' end of the CaMV 35S promoter.

FIG. 2A shows a map of plasmid vector pBII221 utilized in Example I. FIG. 2B depicts linearized pBII221, e.g., from the HindIII cleavage site to the EcoRI cleavage site.

FIG. 7A shows a map of plasmid vector pZ27Z10 utilized in Example II. FIG. 7B depicts linearized plasmid pZ27Z10 encompassing the z10 coding sequence and associated regulatory elements.

DESCRIPTION OF THE PREFERRED EMBODIMENTS

Figure 3:
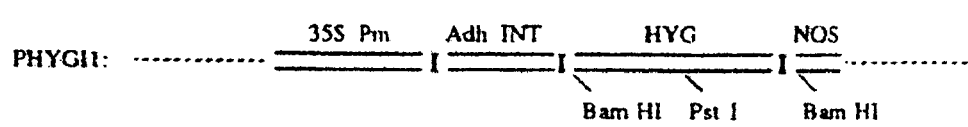
FIG. 3 is a Southern blot of DNA isolated from the PH1 callus line and an untransformed control callus line, and a schematic depiction of the pHYGI1 probes used in the assay.
Figure 3:
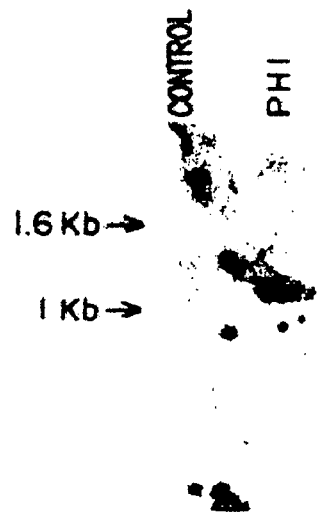

The present invention is directed to the production of fertile transgenic plants and seeds of the species *Zea mays* and to the plants, plant tissues, and seeds derived from such transgenic plants, as well as the subsequent progeny and products derived therefrom, preferably those transgenic *Zea mays* plants having improved food or feed value. The transgenic plants produced herein include all plants of this species, including field corn, popcorn, sweet corn, flint corn and dent corn.

"Transgenic" is used herein to include any cell, cell line, callus, tissue, plant part or plant, the genotype of which has been altered by the presence of recombinant DNA, which DNA has also been referred to in the art of genetic engineering as "heterologous DNA," "exogenous DNA" or "foreign DNA," wherein said DNA was introduced into the genotype by a process of genetic engineering, or which was initially introduced into the genotype of a parent plant by such a process and is subsequently transferred to later generations by sexual crosses or asexual propagation. As used herein, "genotype" refers to the sum total of genetic material within a cell, either chromosomally, or extrachromosomally borne. Therefore, the term "transgenic" as used herein does not encompass the alteration of the genotype of *Zea mays* by conventional plant breeding methods or by naturally occurring events such as random cross-fertilization, viral infection or spontaneous mutation.

By "heritable" is meant that the DNA is capable of transmission through at least one complete sexual cycle of a plant, i.e., it is passed from one plant through its gametes to its progeny plants.

The transgenic plants of this invention may be produced by (i) establishing a regenerable cell culture, preferably a friable embryogenic callus, (ii) transforming said cell culture by a microprojectile bombardment technique, (iii) identifying or selecting transformed cells, and (iv) regenerating fertile transgenic plants from the transformed cells. Some of the plants of this invention may be produced from the transgenic seed produced from the fertile transgenic plants using conventional crossbreeding techniques to develop transgenic elite lines and varieties, or commercial hybrid seed containing recombinant DNA.

I. Plant Lines and Tissue Cultures

The cells which have been found particularly useful to produce the fertile transgenic maize plants herein are those callus cells which are regenerable, both before and after undergoing a selection regimen as detailed further below. Generally, these cells will be derived from meristematic tissue which contains cells which have not yet terminally differentiated. Such tissue in graminaceous cereals in general and in maize, in particular, comprise tissues found in juvenile leaf basal regions, immature tassels, immature embryos, and coleoptilar nodes. Preferably, immature embryos are used. Methods of preparing and maintaining callus from such tissue and plant types are well known in the art and details on so doing are available in the literature, c.f. Phillips et al. (1988), the disclosure of which is hereby incorporated by reference.

The specific callus used must be able to regenerate into a fertile plant. The specific regeneration capacity of particular callus is important to the success of the bombardment/selection process used herein because during and following selection, regeneration capacity may decrease significantly. It is therefore important to start with cultures that have as high a degree of regeneration capacity as possible. Callus which is more than about 3 months and up to about 36 months of age has been found to have a sufficiently high level of regenerability and thus is preferred. The regenerative capacity of a particular culture may be readily determined by transferring samples thereof to regeneration medium and monitoring the formation of shoots, roots, and plantlets. The relative number of plantlets arising per petri dish or per gram fresh weight of tissue may be used as a rough quantitative estimate of regeneration capacity. Generally, a culture which will produce at least one plant per gram of callus tissue is preferred.

While maize callus cultures can be initiated from a number of different plant tissues, the cultures useful herein are preferably derived from immature maize embryos which are removed from the kernels of an ear when the embryos are about 1–3 mm in length. This length generally occurs about 9–14 days after pollination. Under aseptic conditions, the embryos are placed on conventional solid media with the embryo axis down (scutellum up). Callus tissue appears from the scutellum after several days to a few weeks. After the callus has grown sufficiently, the cell proliferations from the scutellum may be evaluated for friable consistency and the presence of well-defined embryos. By "friable consistency" it is meant that the tissue is easily dispersed without causing injury to the cells. Tissue with this morphology is then transferred to fresh media and subcultured on a routine basis about every two weeks. Sieving to reduce clumping and/or to increase cell surface area may be employed during the subculturing period.

The callus initiation media is preferably solid. In preferred embodiments, the initiation/maintenance media is typically based on the N6 salts of Chu et al. (1975) as described in Armstrong et al. (1985) or the MS salts of Murashige et al. (1962). The basal medium is supplemented with sucrose and 2,4-dichlorophenoxyacetic acid (2,4-D). Supplements such as L-proline and casein hydrolysate have been found to improve the frequency of initiation of callus cultures, morphology, and growth. The cultures are generally maintained in the dark, though low light levels may also be used. The level of synthetic hormone 2,4-D, necessary for maintenance and propagation, should be generally about 0.3 to 3.0 mg/l.

Although successful transformation and regeneration has been accomplished herein with friable embryogenic callus, this is not meant to imply that other transformable regenerable cells, tissue, or organs cannot be employed to produce the fertile transgenic plants of this invention. The only actual requirement for the cells which are transformed is that after transformation they must be capable of regeneration of a plant containing the recombinant DNA following the particular selection or screening procedure actually used.

For example, cells grown in liquid suspension culture may be used. To establish these cultures, the type II callus, after 4–6 months, is transferred to liquid growth media. Methods and references for the production of regenerable suspension cell cultures are given by C. E. Green et al. in *Maize for Biological Research*, Plant Molec. Biol. Assoc. (1982) at pages 367–372, R. Phillips et al., *Corn and Corn Improvement*, Agronomy Soc. Amer., (3d ed., 1988) at pages 345–387, and I. Vasil, *Cell Culture and Somatic Cell Genetics of Plants*, Vol. I, *Laboratory Procedures and Their Applications*, Academic Press (1984) at pages 152–158. Typically, the liquid growth media for suspension cultures is of similar formulation to the solid callus induction media. ABA (abscisic acid) ($10^{-7}$M) may be added to the liquid growth media to augment regenerative capacity and enhance culture vitality. It is preferred that the callus not be sieved prior to introduction into the liquid media.

The cultures in liquid media are subcultured as appropriate for maintaining active growth and their regenerative properties. In preferred embodiments, the cultures are subcultured once a week at a 1:8–9 dilution with fresh growth medium.

II. DNA Used for Transformation

As used herein, the term "recombinant DNA" refers to DNA that has been derived or isolated from any source, that may be subsequently chemically altered, and later introduced into *Zea mays*. An example of recombinant DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Therefore "recombinant DNA" includes completely synthetic DNA, semi-synthetic DNA, DNA isolated from biological sources, and DNA derived from introduced RNA. Generally, the recombinant DNA is not originally resident in the *Zea mays* genotype which is the recipient of the DNA, but it is within the scope of the invention to isolate a gene from a given *Zea mays* genotype, and to subsequently introduce multiple copies of the gene into the same genotype, e.g., to enhance production of a given gene product such as a storage protein.

The recombinant DNA includes but is not limited to, DNA from plant genes, and non-plant genes such as those from bacteria, yeasts, animals or viruses; modified genes, portions of genes, chimeric genes, including genes from the same or different *Zea mays* genotype.

The recombinant DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant corn plant. For example, the recombinant DNA may itself comprise or consist of a promoter that is active in *Zea mays*, or may utilize a promoter already present in the *Zea mays* genotype that is the transformation target.

The compositions of, and methods for, constructing recombinant DNA which can transform certain plants are well known to those skilled in the art, and the same compositions and methods of construction may be utilized to produce the DNA useful herein. The specific composition of the DNA is not central to the present invention and the invention is not dependent upon the composition of the specific recombinant DNA used. K. Weising et al., *Ann. Rev. Genetics*, 22, 421 (1988) describes suitable DNA components, selectable marker genes, reporter genes, enhancers, introns, and the like, as well as provides suitable references for compositions therefrom. J. Sambrook et al., *Molecular Cloning: A Laboratory Manual*, Cold Spring Harbor Laboratory Press (2d ed., 1989), provides suitable methods of construction. Generally, the recombinant DNA will be relatively small, i.e., less than about 30 kb to minimize any susceptibility to physical, chemical, or enzymatic degradation which is known to increase as the size of the DNA increases.

Suitable recombinant DNA for use herein includes all DNA which provides for, or enhances, a beneficial feature of the resultant transgenic corn plant. The DNA may encode proteins or antisense RNA transcripts in order to promote increased food values, higher yields, pest resistance, disease resistance, herbicide resistance, and the like. For example, the DNA can encode a DHDP synthase, as does the dap A gene, for increased lysine production; *Bacillus thuringiensis* (Bt), δ-endotoxin or a protease inhibitor for insect resistance; bacterial EPSP synthase for resistance to glyphosate herbicide; and chitinase or glucan endo-1,3-β-glucosidase for fungicidal properties.

Of importance in improving food or feed value are genes encoding proteins that contain high levels of essential amino acids. For example, to be nutritionally adequate and support optimal growth of chickens, corn-soybean meal poultry feed is generally supplemented with synthetic methionine or a methionine analog. The development of lines of corn which supply higher levels of methionine can reduce the need for methionine supplements. The development of such high methionine corn lines can be accomplished by introducing into the corn genome a highly expressed gene or genes encoding a high-methionine protein.

Examples of genes encoding high-methionine proteins include: 1.) the gene encoding a maize 15 kd-zein protein (11% methionine), (Pedersen et al., *J. Biol. Chem.,* 261, 6279 (1986)); 2.) the gene encoding a Brazil nut storage protein (18% methionine), (Altenbach et al., *Plant Mol. Biol.,* 8; 239 (1987)) and 3.) the gene encoding a maize 10 kD-zein protein (22.5% methionine), (Kirihara et al., *Gene,* 7, 359 (1988)). The preferred gene is the 10 kD-zein gene, since it is an endogenous maize gene whose protein product normally accumulates in the kernel and is twice as high in methionine than the 15 kD-zein protein. To obtain high levels of expression in the seed, its coding sequence optionally may be fused to the regulatory sequence from a highly-expressed, seed-specific gene. Alternatively, introduction of additional copies of the intact endogenous 10 kD-zein gene into the corn genome can also increase the methionine content of corn seed.

Lysine, an amino acid essential in the diets of humans and monogastric animals, is among the three most limiting amino acids in most of the staple crops, the cereals in particular. Consequently, grain-based diets must be supplemented with synthetic lysine or with lysine-containing oilseed protein meals. Further, since most oilseed meals are themselves inadequate lysine sources, balancing the feed mixture for lysine frequently results in meals which are too high in other, less desirable nutrients. Therefore, a method to increase the lysine content of either the cereal grains or the oilseed crops or both would result in significant added nutritional value, as well as a significant cost savings to end-users such as the swine and poultry producers.

One approach to improving the lysine content of cereals is to deregulate the biosynthetic pathway, allowing free lysine to accumulate. The dap A gene of *Escherichia coli* encodes dihydrodipicolinic acid synthase (DHDPS), a key regulatory enzyme whose activity in plants is strongly feedback-inhibited by lysine. The bacterial enzyme is about 200-fold less sensitive to inhibition by lysine. The introduction and expression of the dap A gene in plant cells would allow the synthesis of free lysine to continue after the native plant DHDPS has been completely inhibited.

Of particular importance in maintaining yield from corn plants and contributing significantly to controlling the cost of growing a corn crop is the protection of the corn against attack by insect pests. In the USA the major insect pests of corn include a variety of *Lepidoptera* pests such as the European corn borer, cutworms and earworms as well as *Coleoptera* species such as *Diabrotica* spp. The protection of corn against insect attack is expensive to the grower and requires the use of toxic chemical insecticides applied in a timely manner. Since traditional methods of breeding and selection have not allowed for the development of new lines of corn that are substantially resistant to major insect pests, the introduction and inheritance of insect resistance genes or sequences in corn plants in accord with the present invention would reduce costs to the grower, reduce the use of toxic chemical insecticides and provide for more effective control of insect pests.

Essential components of the present invention are the introduction of the insect resistance gene into the corn cell, mitotic application of the gene so that the gene is incorporated into whole corn plants and is ultimately inherited by subsequent offspring of the plant via the processes of mitotic and meiotic division.

*Bacillus thuringiensis* (or "Bt") bacteria include nearly 20 known subspecies of bacteria which produce endotoxin polypeptides that are toxic when ingested by a wide variety of insect species. The biology and molecular biology of the endotoxin proteins (Bt proteins) and corresponding genes (Bt genes) has been reviewed recently by H. R. Whitely et al., *Ann. Rev. Microbiol.*, 40, 549 (1986) and by H. Hofte et al., *Microbiol. Rev.*, 53, 242 (1989). Genes coding for a variety of Bt proteins have been cloned and sequenced. Research has demonstrated that a segment of the Bt polypeptide is essential for toxicity to a variety of *Lepidoptera* pests and is contained within approximately the first 50% of the Bt polypeptide molecule. Consequently, a truncated Bt polypeptide coded by a truncated Bt gene will in many cases retain its toxicity towards a number of *Lepidoptera* insect pests. The HD73 and HD1 Bt polypeptides have been shown to be toxic to the larvae of the important *Lepidoptera* insect pests of corn plants in the USA such as the European corn borer, cutworms and earworms. The genes coding for the HD1 and HD73 Bt polypeptides have been cloned and sequenced by M. Geiser et al., *Gene*, 48, 109 (1986) and M. J. Adang et al., *Gene*, 36, 289 (1985), respectively, and can be cloned from HD1 and HD73 strains obtained from culture collections (e.g. *Bacillus* Genetic Stock Center, Columbus, Ohio or USDA Bt stock collection Peoria, Ill.) using standard protocols.

DNA coding for new, previously uncharacterized Bt toxins, may be cloned from the host *Bacillus* organism using protocols that have previously been used to clone Bt genes. These include the construction of a bank of DNA isolated from the *Bacillus* organism in a suitable plasmid or phage vector replicated in a suitable host and the use of antibodies, raised against the Bt protein or DNA isolated from a homologous Bt gene sequence, to identify transformants that contain the cloned Bt sequence. The approximate location of the Bt coding sequence may be initially determined using deletion analysis of the cloned DNA. The precise location of the Bt coding sequence could be determined using a variety of standard methods, including the determination of the sequence of the cloned segment of DNA, determining the presence of large open reading frames in this sequence that could code for the Bt protein and confirmation of the Bt coding nature of the DNA sequence by comparing the amino acid sequence derived from the DNA sequence with that derived from partial amino acid sequencing of the Bt protein.

A chimeric Bt gene useful in the present invention would comprise a 5' DNA sequence, comprising a sequence of DNA which will allow for the initiation of transcription ("promoter") and translation of a downstream located Bt sequence in a corn plant. The chimeric Bt gene would also comprise a 3' DNA sequence that includes a sequence derived from the 3' non-coding region of a gene that can be expressed in corn. Most importantly, the chimeric Bt gene will include a DNA sequence coding for a toxic Bt polypeptide produced by *Bacillus thuringiensis* or toxic portions thereof or having substantial amino sequence homology thereto. The Bt coding sequence would include: (i) DNA sequences which code for insecticidally active proteins that have substantial homology to Bt endotoxins that are active against insect pests of corn, e.g., the HD73 or HD1 Bt sequences; (ii) sequences coding for insecticidally active segments of the Bt endotoxin polypeptide, e.g., insecticidally active HD73 or HD1 polypeptides truncated from the carboxy and/or amino termini; (iii) a truncated Bt sequence fused in frame with a sequence(s) that codes for a polypeptide that provides some additional advantage such as: (a) genes that are selectable, e.g., genes that confer resistance to antibiotics or herbicides, (b) reporter genes whose products are easy to detect or assay, e.g., luciferase or beta-glucuronidase; (c) DNA sequences that code for polypeptide sequences that have some additional use in stabilizing the Bt protein against degradation or enhance the efficacy of the Bt protein against insects, e.g., protease inhibitors and (d) sequences that help direct the Bt protein to a specific compartment inside or outside the corn cell, e.g., a signal sequence.

To obtain optimum synthesis of the Bt protein in corn, it may also be appropriate to adjust the DNA sequence of the Bt gene to more resemble the genes that are efficiently expressed in corn. Since the codon usage of many Bt genes, including the HD73 and HD1 genes, is more similar to that used by *Bacillus* species and dissimilar to that used by genes that are expressed in maize, the expression of the Bt gene in maize cells can be improved by the replacement of these rarely used *Bacillus* codons with those that are used more frequently in maize plants (See E. Murray et al., *Nucl. Acids Res.*, 17, 477 (1989)). Such replacement of codons would require the substitution of bases without changing the amino acid sequence of the resulting Bt polypeptide. The Bt polypeptide would be identical in sequence to the bacterial gene or segments thereof. The complete Bt coding sequence, or sections thereof, containing a higher proportion of maize preferred codons than the original bacterial gene could be synthesized using standard chemical synthesis protocols, and introduced or assembled into the Bt gene using standard protocols, such as site-directed mutagenesis or DNA polymerization and ligation and the like.

Aside from recombinant DNA sequences that serve as transcription units or portions thereof, useful recombinant DNA may be untranscribed, serving a regulatory or a structural function. Also, the DNA may be introduced to act as a genetic tool to generate mutants and/or assist in the identification, genetic tagging, or isolation of segments of corn DNA. Additional examples may be found in Weising, cited supra.

The recombinant DNA to be introduced into the plant cells further will generally contain either a selectable marker or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in plants. Useful selectable markers are well known in the art and include, for example, antibiotic and herbicide resistance genes.

Specific examples of selectable marker genes are disclosed in Weising et al., cited supra. A preferred selectable marker gene is the hygromycin phosphotransferase (HPT) coding sequence, which may be derived from E. coli and which confers resistance to the antibiotic hygromycin B. Other selectable markers include the aminoglycoside phosphotransferase gene of transposon Tn5 (AphII) which encodes resistance to the antibiotics kanamycin, neomycin and G418, as well as those genes which code for resistance or tolerance to glyphosate, 2,2-dichloropropionic acid, methotrexate, imidazolinone herbicides, sulfonylurea herbicides, bromoxynil, phosphinothricin and other herbicidal compounds. Those selectable marker genes which confer resistance or tolerance to these phytotoxic compounds are also of commercial utility in the resulting transformed plants. Selectable marker genes encoding enzymes which impart resistance to phytotoxic compounds are listed in Table 1, below.

TABLE 1

Selectable Marker Genes

| Resistance Gene or Enzyme | Confers Resistance to: | Reference |
| --- | --- | --- |
| Neomycin phosphotransferase (neo) | G-418, neomycin, kanamycin | P. J. Southern et al., J. Mol. Appl. Gen., 1, 327 (1982) |
| Hygromycin phosphotranferase (hpt or hyg) | Hygromycin B | Y. Shimizu et al., Mol. Cell Biol., 6, 1074 (1986) |
| Dihydrofolate reductase (dhfr) | Methotrexate | W. W. Kwok et al., PNAS USA, 4552 (1986) |
| Phosphinothricin acetyltransferase (bar) | Phosphinothricin | M. DeBlock et al., ENBO J., 6, 2513 (1987) |
| 2,2-Dichloropropionic acid dehalogenase | 2,2-Dichloropropionic acid (Dalapon) | V. Buchanan-Wollaston et al., J. Cell. Biochem., Supp. 13D, 330 (1989) |
| Acetohydroxyacid synthase | Sulfonylurea, imidazolinone and triazolopyrimidine herbicides | P. C. Anderson et al. (U.S. Pat. No. 4,761,373); G. W. Haughn et al., Mol. Gen. Genet., 211, 266 (1988) |
| 5-Enolpyruvyl-shikimate-phosphate synthase (aroA) | Glyphosate | L. Comai et al., Nature, 317, 741 (1985) |

TABLE 1-continued

Selectable Marker Genes

| Resistance Gene or Enzyme | Confers Resistance to: | Reference |
| --- | --- | --- |
| Haloarylnitrilase | Bromoxynil | D. H. Stalker et al., published PCT appln. WO87/04181 |
| Acetyl-coenzyme A carboxylase | Sethoxydim, haloxyfop | W. B. Parker et al., Plant Physiol., 92, 1220 (1990) |
| Dihydropteroate synthase (sul I) | Sulfonamide herbicides | F. Guerineau et al., Plant Molec. Biol., 15, 127 (1990) |
| 32 kD photosystem II polypeptide (psbA) | Triazine herbicides | J. Hirschberg et al., Science, 222, 1346 (1983) |
| Anthranilate synthase | 5-Methyltryptophan | K. Hibberd et al., (U.S. Pat. No. 4,581,847) |
| Dihydrodipicolinic acid synthase (dap A) | Aminoethyl cysteine | K. Glassman et al., published PCT application No. WO89/11789 |

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., phenotypic change or enzymatic activity. Examples of such genes are provided in weising et al., supra. Preferred genes include the chloramphenicol acetyl transferase gene (cat) from Tn9 of E. coli, the beta-glucuronidase gene (gus) of the uidA locus of E. coli, and the luciferase gene from firefly Photinus pyralis. Expression of the reporter gene is assayed at a suitable time after the DNA has been introduced into the recipient cells. A preferred such assay entails the use of the E. coli beta-glucuronidase (GUS) gene (R. Jefferson et al., EMBO J., 16, 3901 (1987)). Maize cells transformed and expressing this gene will stain blue upon exposure to the substrate, 5-bromo-4-chloro-3-indolyl-beta-D-glucuronide (X-GLUC), in the extracellular medium.

The regulatory sequences useful herein include any constitutive, inducible, tissue or organ specific, or developmental stage specific promoter which can be expressed in the particular plant cell. Suitable such promoters are disclosed in Weising et al., supra. The following is a partial representative list of promoters suitable for use herein: regulatory sequences from the T-DNA of Agrobacterium tumefaciens, including mannopine synthase, nopaline synthase, and octopine synthase; alcohol dehydrogenase promoter from corn; light-inducible promoters such as the ribulose-bisphosphate-carboxylase/oxygenase small subunit genes from a variety of species; and the major chlorophyll a/b binding protein gene promoters; 35S and 19S promoters of cauliflower mosaic virus (CaMV); developmentally regulated promoters such as the waxy, zein, or bronze promoters from maize; as well as synthetic or other natural promoters which are either inducible or constitutive, including those promoters exhibiting organ-specific expression or expression at specific development stage(s) of the plant.

Other elements such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the plant. For example, the maize AdhIS first intron may be placed between the promoter and the coding sequence in a particular recombinant DNA construction. This intron, when included in a DNA construction, is known to increase production of a protein in maize cells. (J. Callis et al., *Genes and Develop.*, 1, 1183 (1987)). However, sufficient expression for a selectable marker to perform satisfactorily can often be obtained without an intron. (T. Klein et al., *Plant Physiol.*, 91, 440 (1989)). An example of an alternative suitable intron is the shrunken-1 first intron of *Zea mays*. These other elements must be compatible with the remainder of the DNA constructions.

III. DNA Delivery Process

The recombinant DNA can be introduced into the regenerable maize cell cultures, preferably into callus cultures via a particle bombardment process. A general description of a suitable particle bombardment instrument is provided in Sanford et al. (1987), the disclosure of which is incorporated herein by reference. While protocols for the use of the instrument in the bombardment of maize non-regenerable suspension culture cells are described in Klein et al. (1988a, 1988b, and 1989), no protocols have been published for the bombardment of callus cultures or regenerable maize cells.

In a microprojectile bombardment process, also referred to as a biolistic process, the transport of the recombinant DNA into the callus is mediated by very small particles of a biologically inert material. When the inert particles are coated with DNA and accelerated to a suitable velocity, one or more of the particles is able to enter into one or more of the cells where the DNA is released from the particle and expressed within the cell. Some of the recipient cells stably retain the introduced DNA and express it.

The particles, called microprojectiles, are generally of a high density material such as tungsten or gold. They are coated with the DNA of interest. The microprojectiles are then placed onto the surface of a macroprojectile which serves to transfer the motive force from a suitable energy source to the microprojectiles. After the macroprojectile and the microprojectiles are accelerated to the proper velocity, they contact a blocking device which prevents the macroprojectile from continuing its forward path but allows the DNA-coated microprojectiles to continue on and impact the recipient callus cells. Suitable such instruments may use a variety of motive forces such as gunpowder or shock waves from an electric arc discharge (P. Christou et al., *Plant Physiol.*, 87, 671 (1988)). An instrument in which gunpowder is the motive force is currently preferred and such is described and further explained in Sanford et al. (1987), the disclosure of which is incorporated herein by reference.

A protocol for the use of the gunpowder instrument is provided in Klein et al. (1988a,b) and involves two major steps. First, tungsten microprojectiles are mixed with the DNA, calcium chloride, and spermidine in a specified order in an aqueous solution. The concentrations of the various components may be varied as taught. The preferred procedure entails exactly the procedure of Klein et al. (1988b) except for doubling the stated optimum DNA concentration. Secondly, the DNA-coated microprojectiles, macroprojectiles, and recipient cells are placed in position in the instrument and the motive force is applied to the macroprojectiles. Parts of this step which may be varied include the distance of the recipient cells from the end of the barrel as well as the vacuum level in the sample chamber. The recipient tissue is positioned 2–15, preferably 5 cm below the stopping plate tray.

The callus cultures useful herein for generation of transgenic plants should generally be about midway between transfer periods, and thus, past any "lag" phase that might be associated with a transfer to a new media, but also before reaching any "stationary" phase associated with an extended period of time without subculture to fresh media. The tissue may be used in the form of pieces of about 30 to 80, preferably about 40 to 60, mg. The clumps can be placed on a petri dish or other surface and arranged in essentially any manner, recognizing that (i) the space in the center of the dish will receive the heaviest concentration of metal-DNA particles and the tissue located there is likely to suffer damage during bombardment and, (ii) the number of particles reaching the tissue will decrease with increasing distance of the tissue from the center of the blast so that the tissue far from the center of the dish is less likely to be bombarded. A mesh screen, preferably of metal, may be laid on the dish to prevent splashing or ejection of the tissue. An alternative method for presentation of the tissue for bombardment is to spread the tissue onto a filter paper in a thin layer. The tissue may be bombarded one or more times with the DNA-coated metal particles.

IV. Selection Process

Once the calli have been bombarded with the recombinant DNA and the DNA has penetrated some of the cells, it is necessary to identify and select those cells which both contain the recombinant DNA and still retain sufficient regenerative capacity. There are two general approaches which have been found useful for accomplishing this. First, the transformed calli or plants regenerated therefrom can be screened for the presence of the recombinant DNA by various standard methods which could include assays for the expression of reporter genes or assessment of phenotypic effects of the recombinant DNA, if any. Alternatively, and preferably, when a selectable marker gene has been transmitted along with or as part of the recombinant DNA, those cells of the callus which have been transformed can be identified by the use of a selective agent to detect expression of the selectable marker gene.

Selection of the putative transformants is a critical part of the successful transformation process since selection conditions must be chosen so as to allow growth and accumulation of the transformed cells while simultaneously inhibiting the growth of the non-transformed cells. The situation is complicated by the fact that the vitality of individual cells in a population is often highly dependent on the vitality of neighboring cells. Also, the selection conditions must not be so severe that the plant regeneration capacity of the callus cells and the fertility of the resulting plant are precluded. Thus, the effects of the selection agent on cell viability and morphology should be evaluated. This may be accomplished by experimentally producing a growth inhibition curve for the given selective agent and tissue being transformed beforehand. This will establish the concentration range which will inhibit growth.

When a selectable marker gene has been used, the callus clumps may be either allowed to recover from the bombardment on non-selective media, or preferably, directly transferred to media containing the selection agent.

Selection procedures involve exposure to a toxic agent and may employ sequential changes in the concentration of the agent and multiple rounds of selection. The particular concentrations and cycle lengths are likely to need to be varied for each particular agent. A currently preferred selection procedure entails using an initial selection round at a relatively low toxic agent concentration and then later round(s) at higher concentration(s). This allows the selective agent to exert its toxic effect slowly over a longer period of time. Preferably, the concentration of the agent is initially such that about a 5–40% level of growth inhibition will occur, as determined from a growth inhibition curve. The effect may be to allow the transformed cells to preferentially grow and divide while inhibiting untransformed cells, but not to the extent that growth of the untransformed cells is prevented. Once the few individual transformed cells have divided a sufficient number of times, the tissue may be shifted to media containing a higher concentration of the toxic agent to kill essentially all untransformed cells. The shift to the higher concentration also reduces the possibility of non-transformed cells adapting to the agent. The higher level is preferably in the range of about 30 to 100% growth inhibition. The length of the first selection cycle may be from about 1 to 4 weeks, preferably about 2 weeks. Later selection cycles may be from about 1 to 12 weeks, preferably about 2 to 10 weeks. Putative maize transformants can generally be identified as proliferating sectors of tissue among a background of non-proliferating cells. The callus may also be cultured on non-selective media at various times during the overall selection procedure.

Once a callus sector is identified as a putative transformant, transformation can be confirmed by phenotypic and/or genotypic analysis. If a selection agent is used, an example of phenotypic analysis is to measure the increase in fresh weight of the putative transformant as compared to a control on various levels of the selective agent. Other analyses that may be employed will depend on the function of the recombinant DNA. For example, if an enzyme or protein is encoded by the DNA, enzymatic or immunological assays specific for the particular enzyme or protein may be used. Other gene products may be assayed by using a suitable bioassay or chemical assay. Other such techniques are well known in the art and are not repeated here. The presence of the gene can also be confirmed by conventional procedures, i.e., Southern blot or polymerase chain reaction (PCR) or the like.

V. Regeneration of Plants and Production of Seed

Cell lines which have been shown to be transformed must then be regenerated into plants and the fertility of the resultant plants determined. Transformed lines which test positive by genotypic and/or phenotypic analysis are then placed on a medium which promotes tissue differentiation and plant regeneration. Regeneration may be carried out in accordance with standard procedures well known in the art. The procedures commonly entail reducing the level of auxin which discontinues proliferation of a callus and promotes somatic embryo development or other tissue differentiation. One example of such a regeneration procedure is described in Green et al. (1982). The plants are grown to maturity in a growth room or greenhouse and appropriate sexual crosses are made as described by Neuffer (1982).

Regeneration, while important to the present invention, may be performed in any conventional manner. If a selectable marker has been transformed into the cells, the selection agent may be incorporated into the regeneration media to further confirm that the regenerated plantlets are transformed. Since regeneration techniques are well known and not critical to the present invention, any technique which accomplishes the regeneration and produces fertile plants may be used.

VI. Analysis of R1 Progeny

The plants regenerated from the transformed callus are referred to as the R0 generation or R0 plants. The seeds produced by various sexual crosses of the R0 generation plants are referred to as R1 progeny or the R1 generation. When R1 seeds are germinated, the resulting plants are also referred to as the R1 generation.

To confirm the successful transmission and inheritance of the recombinant DNA through one complete sexual cycle, the R1 generation should be analyzed to confirm the presence of the transforming DNA. The analysis may be performed in any of the manners such as were disclosed above for analyzing the bombarded callus for evidence of transformation, taking into account the fact that plants and plant parts are being used in place of the callus.

The recombinant DNA can show different types of inheritance patterns for different transformed lines. For example, the recombinant DNA may be inherited in the progeny according to the rules of Mendelian inheritance. This type of heritability involves transmission of the DNA through both the male and female gametes and is associated with stable integration or incorporation into maize nuclear DNA. An alternative type of inheritance pattern is maternal inheritance, in which the recombinant DNA is transmitted primarily or exclusively through the female gametes. The inheritance pattern for a particular transformant may be ascertained by analysis of the progeny of various sexual crosses.

VII. Establishment of the Recombinant DNA in Other Maize Varieties

Fertile, transgenic plants may then be used in a conventional maize breeding program in order to incorporate the introduced recombinant DNA into the desired lines or varieties. Methods and references for convergent improvement of corn are given by Hallauer et al., (1988) incorporated herein by reference. Among the approaches that conventional breeding programs employ is a conversion process (backcrossing). Briefly, conversion is performed by crossing the initial transgenic fertile plant to elite inbred lines. The progeny from this cross will segregate such that some of the plants will carry the recombinant DNA whereas some will not. The plants that do carry the DNA are then crossed again to the elite inbred lines resulting in progeny which segregate once more. This backcrossing process is repeated until the original elite inbred has been converted to a line containing the recombinant DNA, yet possessing all important attributes originally found in the parent. Generally, this will require about 6–8 generations. A separate backcrossing program will be generally used for every elite line that is to be converted to a genetically engineered elite line.

Generally, the commercial value of the transformed corn produced herein will be greatest if the recombinant DNA can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, and insect resistance. As such, it is necessary to incorporate the recombinant DNA into a large number of parental lines so that many hybrid combinations can be produced containing the desirable heterologous DNA.

Corn breeding and the techniques and skills required to transfer genes from one line or variety to another are well known to those skilled in the art. Thus, introducing recombinant DNA into any other line or variety can be accomplished by these breeding procedures.

VIII. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents (e.g., oils or starches) of corn and other crops are extracted for foods or industrial use and transgenic plants may be created which have enhanced or modified levels of such components.

Transgenic plants may also find use in the commercial manufacture of proteins or other molecules, where the molecule of interest is extracted or, purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from corn cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The following non-limiting examples are illustrative of the present invention. They are presented to better explain the general procedures which were used to prepare the fertile Zea mays plants of this invention which stably express the recombinant DNA and which transmit that DNA to progeny. All parts and percentages are by weight unless otherwise specified. It must be recognized that the probability of a specific transformation event occurring is a function of the amount of material subjected to the transformation procedure. Thus, when individual situations arise in which the procedures described herein do not produce a transformed product, repetition of the procedures will be required.

EXAMPLE I

Fertile Transgenic Zea mays Plants from Callus Line AB11

I. Initiation and Maintenance of Maize Cell Cultures which Retain Plant Regeneration Capacity Friable, embryogenic maize callus cultures were initiated from hybrid immature embryos produced by pollination of inbred line A188 plants (University of Minnesota, Crop Improvement Association) with pollen of inbred line B73 plants (Iowa State University). Ears were harvested when the embryos had reached a length of 1.5 to 2.0 mm. Each ear was surface sterilized in 50% v/v commercial bleach (2.63% w/v sodium hypochlorite) for 20 min. at room temperature. The ears were then washed with sterile, distilled, deionized water. Immature embryos were aseptically isolated and placed on nutrient initiation/maintenance medium with the root/shoot axis exposed to the medium. Initiation/maintenance medium (hereinafter referred to as "F medium") consisted of N6 basal media (Chu 1975) with 2% (w/v) sucrose, 1.5 mg per liter 2,4-dichlorophenoxyacetic acid (2,4-D), 6 mM proline, and 0.25% Gelrite (Kelco, Inc., San Diego). The pH was adjusted to 5.8 prior to autoclaving. Unless otherwise stated, all tissue culture manipulations were carried out under sterile conditions.

The immature embryos were incubated at 26° C. in the dark. Cell proliferations from the scutellum of the immature embryos were evaluated for friable consistency and the presence of well-defined somatic embryos. Tissue with this morphology was transferred to fresh media 10 to 14 days after the initial plating of the immature embryos. The tissue was then subcultured on a routine basis every 14 to 21 days. Sixty to eighty milligram quantities of tissue were removed from pieces of tissue that had reached a size of approximately one gram and were transferred to fresh media. Subculturing always involved careful visual monitoring to be sure that only tissue of the correct morphology was maintained. The presence of somatic embryos ensured that the cultures would give rise to plants under the proper conditions. The cell culture named AB11 used in this example was such a culture and had been initiated about 1 year before bombardment.

II. Plasmids

The plasmid pHYGI1, was constructed in the vector pBS+ (Stratagene, Inc., San Diego, Calif.), a 3.2 Kb circular plasmid, using standard recombinant DNA techniques. The 553 bp Bcl-BamHI fragment containing the maize AdhIS first intron (Callis et al. 1987) was inserted between the CaMV 35S promoter and the hygromycin coding sequence of pCHN1-1, a plasmid constructed in accord with Example V. A map of pHYGI1 is provided as FIG. 1. A sample of pHYGI1 was deposited at the American Type Culture Collection, Rockville, Md., USA, on Mar. 16, 1990, under the provisions of the Budapest Treaty, and assigned accession number 40774.

pBII221 contains the *E. coli* β-glucuronidase coding sequence flanked at the 5' end by the CaMV 35S promoter and at the 3' end by the nos polyadenylation sequence. The plasmid was constructed by inserting the maize AdhIS first intron between the 35S promoter and the coding sequence of pBI221 (Jefferson et al. 1987). A map of pBII221 is provided as FIG. 2.

Plasmids were introduced into the embryogenic callus culture AB11 by microprojectile bombardment.

III. DNA delivery process

The embryogenic maize callus line AB11 was subcultured 7 to 12 days prior to microprojectile bombardment. AB11 callus was prepared for bombardment as follows. Five clumps of callus, each approximately 50 mg in wet weight were arranged in a cross pattern in the center of a sterile 60×15 mm petri plate (Falcon 1007). Plates were stored in a closed container with moist paper towels, throughout the bombardment process. Twelve plates were prepared.

Plasmids were coated onto M-10 tungsten particles (Biolistics) exactly as described by Klein et al. (1988b) except that, (i) twice the recommended quantity of DNA was used, (ii) the DNA precipitation onto the particles was performed at 0° C., and (iii) the tubes containing the DNA-coated tungsten particles were stored on ice throughout the bombardment process.

All of the tubes contained 25 μl of 50 mg/ml M-10 tungsten in water, 25 μl of 2.5 M CaCl$_2$, and 10 μl of 100 mM spermidine along with a total of 5 μl of 1 mg/ml plasmid DNA. When both plasmids were used, each was present in an amount of 2.5 μl. One tube contained only plasmid pBII221; and one tube contained T.E. buffer (see Table 2, below).

All tubes were incubated on ice for 10 min., the particles were pelleted by centrifugation in an Eppendorf centrifuge at room temperature for 5 seconds, 25 μl of the supernatant was discarded. The tubes were stored on ice throughout the bombardment process. Each preparation was used for no more than 5 bombardments.

Macroprojectiles and stopping plates were obtained from Biolistics, Inc. (Ithaca, N.Y.). They were sterilized as described by the supplier. The microprojectile bombardment instrument was obtained from Biolistics, Inc.

The sample plate tray was placed 5 cm below the bottom of the stopping plate tray of the microprojectile instrument, with the stopping plate in the slot nearest to the barrel. Plates of callus tissue prepared as described above were centered on the sample plate tray and the petri dish lid removed. A 7×7 cm square rigid wire mesh with 3×3 mm mesh and made of galvanized steel was placed over the open dish in order to retain the tissue during the bombardment. Tungsten/DNA preparations were sonicated as described by Biolistics, Inc. and 2.5 μl of the suspensions were pipetted onto the top of the macroprojectiles for each bombardment. The instrument was operated as described by the manufacturer. The bombardments which were performed are summarized on Table 2.

TABLE 2

| | |
|---|---|
| 2 × pBII221 prep | To determine transient expression frequency |
| 7 × pHYGI1/pBII221 (1:1) | As a potential positive treatment for transformation |
| 3 × T.E.[a] | Negative control treatment |

[a]10 mM Tris-HCL, pH 8.0, 1 mM EDTA

The two plates of callus bombarded with pBII221 were transferred plate for plate to F medium (with no hygromycin) and the callus cultured at 26° C. in the dark. After 2 days, this callus was then transferred plate for plate into 35×10 mm petri plates (Falcon 1008) containing 2 ml of GUS assay buffer (1 mg/ml of 5-bromo-4-chloro-3-indolyl-beta-D-glucuronide) (Research Organics), 100 mM sodium phosphate pH 7.0, 5 mM each of potassium ferricyanide and potassium ferrocyanide, 10 mM EDTA, and 0.06% Triton X-100. The plates were incubated at 37° C. for 3 days after which the number of blue cells was counted giving a total of 313 and 355 transient GUS-expressing cells visible in the two plates, suggesting that the DNA delivery process had also occurred with the other bombarded plates. The plates of tissue used in the GUS assay were discarded after counting since the GUS assay is destructive.

IV. Selection process

Hygromycin B (Calbiochem) was incorporated into the medium prior to pouring plates by addition of the appropriate volume of filter-sterilized 100 mg/ml hygromycin B dissolved in water, when the medium had cooled to 45° C.

Immediately after all samples had been bombarded, callus from all of the plates treated with pHYGI1/pBII221, and two of the T.E. plates was transferred plate for plate onto F medium containing 15 mg/l hygromycin B, (ten pieces of callus per plate). These are referred to as round 1 selection plates. Callus from the T.E. treated plate was transferred to F medium without hygromycin. This tissue was subcultured every 2–3 weeks onto nonselective medium and is referred to as unselected control callus.

After 14 days of selection, tissue appeared essentially identical on both selective and nonselective media. All callus from seven plates of the pHYGI1/pBII221 and one T.E. treated plate were transferred from round 1 selection plates to round 2 selection plates that contained 60 mg/l hygromycin. The round 2 selection plates each contained ten 30 mg pieces of callus per plate, resulting in an expansion of the total number of plates.

After 21 days on the round 2 selection plates, all of the material was transferred to round 3 selection plates containing 60 mg/l hygromycin. After 79 days post-bombardment, the round 3 sets of selection plates were checked for viable sectors of callus. One of the sectors was proliferating from a background of necrotic tissue on plates treated with pHYGI1/pBII221. The sector was designated PH3 and was transferred to F medium without hygromycin.

After 19 days on F medium without hygromycin, PH3 was transferred to F-medium containing 60 mg/l hygromycin. PH3 was found to be capable of sustained growth through multiple subcultures in the presence of 60 mg/l hygromycin.

V. Confirmation of Transformed Callus

To show that the PH3 callus had acquired the hygromycin resistance gene, genomic DNA was isolated from PH3 callus and unselected control callus in accord with Example V, and analyzed by Southern blotting. The isolated DNA (10 μg) was digested with BamHI (NEB) and electrophoresed in a 0.8% w/v agarose gel at 15 V for 16 hrs in TAE buffer (40 mM Tris-acetate, pH 7.6, 1 mM EDTA). The DNA was transferred to a Nytran membrane (Schleicher and Schuell). Transfer, hybridization and washing conditions were carried out as per the manufacturer's recommendations.

A $^{32}$P labelled probe was prepared by random primer labelling with an Oligo Labelling Kit (Pharmacia) as per the supplier's instructions with α-$^{32}$P-dCTP (ICN Radiochemicals). The template DNA used was the 1055 bp BamHI fragment of pHYGI1, which contains the entire HPT coding sequence.

Membranes were exposed to Kodak X-OMAT AR film in an X-OMATIC cassette with intensifying screens. A band was observed for PH3 callus at the expected position of 1.05 Kb, indicating that the HPT coding sequence was present. No band was observed for control callus.

To demonstrate that the hygromycin gene is incorporated into high molecular weight DNA, undigested DNA from PH3 callus and control callus was electrophoresed, blotted and hybridized as described above. Undigested PH3 DNA only showed hybridization to the probe at a mobility equal to uncut DNA. No hybridization was observed for DNA from control callus. These results demonstrate that the HPT coding sequence is not present in PH3 callus as intact pHYGI1 or as a small non-chromosomal plasmid. The results are consistent with incorporation of the hygromycin gene into high molecular weight DNA.

VI. Plant Regeneration and Production of Seed

Portions of PH3 callus were transferred directly from plates containing 60 mg/l hygromycin to RM5 medium which consists of MS basal salts (Murashige et al. 1962) supplemented with thiamine.HCl 0.5 mg/l, 2,4-D 0.75 mg/l, sucrose 50 g/l, asparagine 150 mg/l, and Gelrite 2.5 g/l (Kelco Inc., San Diego).

After 14 days on RM5 medium, the majority of PH3 and unselected control callus was transferred to R5 medium (RM5 medium, except that 2,4-D is omitted). The plates were cultured in the dark for 7 days at 26° C. and transferred to a light regime of 14 hrs light and 10 hrs dark for 14 days at 26° C. At this point, plantlets that had formed were transferred to one quart canning jars (Ball) containing 100 ml of R5 medium. Plants were transferred from jars to vermiculite for 7 or 8 days before transplanting them into soil and growing them to maturity. A total of 45 plants were produced from PH3 and a total of 10 plants were produced from control callus.

Controlled pollinations of mature PH3 plants were conducted by standard techniques with inbred *Zea mays* lines MBS501 (Mike Brayton Seeds), FR4326 (Illinois Foundation Research) and the proprietary inbred line LM1112. Seed was harvested 45 days post-pollination and allowed to dry further for 1–2 weeks.

VII. Analysis of the R1 Progeny

R1 plants were tested for the presence of the HPT and GUS gene sequences by PCR analysis. Expression of the HPT gene was determined with an enzymatic assay for HPT activity. Table 3 summarizes the data. These data demonstrate transmission and expression of the recombinant DNA through both male and female parents, and are consistent with Mendelian inheritance. The Southern blot evidence for integration of the HPT coding sequence into high molecular weight DNA for the source callus, combined with the inheritance data, suggest that the foregoing DNA sequences are chromosomally integrated. The presence of GUS gene sequences in the R1 progeny demonstrates cotransformation and inheritance of an unselected gene.

TABLE 3

Analysis of R1 Progeny of PH3 Transformants

| PH3.4 Plant | Enzyme HPT Assay | PCR Assay HPT | PCR Assay GUS |
|---|---|---|---|
| Parents: MBS501 × PH3.4 | | | |
| 4.1 | − | − | − |
| 4.2 | + | + | + |
| 4.3 | + | + | + |
| 4.4 | − | − | − |
| 4.5 | + | + | + |
| 4.6 | + | + | + |
| 4.7 | + | + | + |
| 4.8 | − | − | − |
| 4.9 | − | − | − |
| Parents: LM1112 × PH3.18 | | | |
| 18.1 | − | − | − |
| 18.2 | + | + | + |
| 18.3 | − | − | − |
| 18.4 | − | − | − |
| 18.5 | + | + | + |
| 18.6 | + | + | + |
| 18.7 | + | + | + |
| 18.8 | + | + | + |
| 18.9 | + | + | + |
| 18.10 | + | + | + |

TABLE 3-continued

| Plant | Enzyme HPT Assay | PCR Assay HPT | PCR Assay GUS |
|---|---|---|---|
| Parents: PH3.2 × FR4326 | | | |
| 2.1 | − | − | − |
| 2.2 | − | − | − |
| 2.3 | + | + | + |
| 2.4 | − | − | − |
| 2.5 | + | + | + |
| 2.6 | − | − | − |
| 2.7 | + | + | + |
| 2.8 | + | + | ND |
| 2.9 | + | + | ND |
| Controls Parents: TE3.1 × Oh43 | | | |
| 3.1 | − | − | ND |
| 3.2 | − | − | ND |
| 3.3 | − | − | ND |
| 3.4 | − | − | ND |
| 3.5 | − | − | ND |
| 3.6 | − | − | ND |
| 3.7 | − | − | − |
| 3.8 | − | − | − |
| 3.9 | − | − | − |
| 3.10 | − | − | − |
| 3.11 | − | ND | ND |
| 3.12 | − | ND | ND |
| 3.13 | − | ND | ND |
| 3.14 | − | ND | ND |
| 3.15 | − | ND | ND |
| 3.16 | − | ND | ND |
| 3.17 | − | ND | ND |
| 3.18 | − | ND | ND |
| 3.19 | − | ND | ND |
| 3.20 | − | ND | ND |
| 3.21 | − | ND | ND |
| 3.22 | − | ND | ND |
| 3.23 | − | ND | ND |
| 3.24 | − | ND | ND |

The HPT enzyme assay was based on the following methods: S. K. Datta et al., *Bio/Technology*, 8, 736 (1990), M. Staebell et al., *Anal. Biochem.*, 185, 319 (1990), and E. Cabanes-Bastos, *Gene*, 77, 169 (1989).

Root samples (0.2 g) were excised from 7–10 day old seedlings and were quick frozen in liquid nitrogen ($N_2$). Samples were ground with alumina and 400 µl of EB (50 mM Tris-HCl, 10% v/v glycerol, 0.1 mM PMSF, pH 7.0) for 30–60 seconds using a disposable pestle and tube (Kontes), then centrifuged in an Eppendorf microfuge for 10 min. The supernatant was transferred to a Centricon 30 filter unit and desalted by centrifuging in a fixed angle rotor at 5000 rpm in a Beckman GPR centrifuge for 30 min at 4° C. One ml of EB was used to wash each filter unit, spinning an additional 5000 RPM for 60 min. The retentate was then recovered and stored at −70° C. Samples of transgenic and unselected control callus tissue (0.2 g) were ground as described above, and the supernatents were used as positive and negative controls.

Protein was quantified using the method of Bradford, *Anal. Biochem.*, 72, 248 (1976) with a BioRad kit. Protein concentrations in root extracts ranged from 0.2–2 µg/µl.

The root extract (4 µg total protein) was added to a reaction mixture containing 20 mM Tris-maleate, 13 mM $MgCl_2$, 120 mM $NH_4Cl$, 0.5 mM DTT, 50 µM ATP, 0.61 µg/µl hygromycin B, 25 µg/µl bovine serum albumin, and 12 µCi gamma 32P-ATP. Reaction volume was 33 µl. The reaction mixture was incubated for 30 min at 37° C.

One µl of the reaction mixture was spotted on a polyethyleneimine cellulose thin layer chromatography plate (Sigma Chem. Co.). Plates were developed in 50 mM formic acid pH 5.4, air dried, and exposed to Kodak XAR-5 film. The reaction product, hygromycin phosphate, migrates near the solvent front under these conditions.

To conduct the PCR assay, 0.1 g samples were taken from plant tissues and frozen in liquid nitrogen. Samples were then ground with 120 grit carborundum in 200 µl 0.1M Tris-HCl, 0.1M NaCl, 20 mM EDTA, 1% Sarkosyl pH 8.5) at 4° C. Following phenol/chloroform extraction and ethanol and isopropanol precipitations, samples were suspended in T.E. and analyzed by polymerase chain reaction (K. B. Mullis, U.S. Pat. No. 4,683,202).

PCR was carried out in 100 µl volumes in 50 mM KCl, 10 mM Tris-HCl pH 8.4, 3 mM $MgCl_2$, 100 µg/ml gelatin, 0.25 µM each of the appropriate primers, 0.2 mM of each deoxynucleoside triphosphate (DATP, dCTP, dGTP, dTTP), 2.5 Units of Taq DNA polymerase (Cetus), and 10 µl of the DNA preparation. The mixture was overlaid with mineral oil, heated to 94° C. for 3 min, and amplified for 35 cycles of 55° C. for 1 min, 72° C. for 1 min, 94° C. for 1 min. The mixture was then incubated at 50° C. for 2 min and 72° C. for 5 min. 10 µl of the PCR product was electrophoresed in agarose gels and visualized by staining with ethidium bromide.

For analysis of the presence of the HPT gene, a PCR primer complementary to the 35S promoter, and one complementary to the HPT coding sequence were employed. Thus, in order to generate the appropriately sized PCR product, the HPT template DNA must contain contiguous 35S promoter region, Adh1 intron, and 5' protein coding sequence region.

For analysis of the presence of the GUS gene, PCR primers complementary to sequences within the GUS protein coding region were employed. A 797 bp PCR product is predicted if the template DNA contains an intact coding region between the two primers.

EXAMPLE II

Fertile Transgenic Plants from Callus Line AB63S Containing Recombinant DNA Encoding a Seed Storage Protein The 10 kD-zein storage protein is produced in the endosperm of the maize kernel and is a representative member of a class of proteins referred to as "seed storage proteins." The protein contains extremely high levels of methionine (22.5%) and is encoded by the Zps10/(22) gene (M. S. Benner et al., *Theor. Appl. Genet.*, 78, 761 (1989)); a gene referred to as z10 herein. Thus, increased expression of the z10 gene can be used to increase the methionine content of corn. Production of fertile transgenic corn containing a chimeric z10 gene was accomplished by the procedures of Example I with some minor modifications. Example II also demonstrates the introduction of recombinant DNA using a callus line different from that used in Example I.

I. Tissue Culture Lines

The embryogenic maize callus line named AB63S used in this example was produced from immature embryos resulting from a cross between elite inbred lines A188 and B73, by the initiation and maintenance procedures described in Example I. The callus line had been initiated approximately 7 months prior to bombardment. Eleven weeks prior to bombardment the tissue was sieved by forcing it through a 1.9 mm screen and plated onto N6 maintenance medium. Friable, embryogenic callus was selected from the resulting tissue after 1–2 weeks of growth, transferred to fresh edium and allowed to grow for 1.5–3 weeks before sieving again. This cycle of sieving and recovery of friable callus was carried out a total of three times prior to subjecting the tissue to bombardment.

II. Plasmids

The plasmids pHYGI1 and pBII221 described in Example I were used in this Example. In addition, the plasmid pZ27Z10 was included in the DNA/tungsten preparations. The plasmid pZ27Z10 was constructed using the vector pUC118 (J. Vieira et al., *Methods Enzymol.*, 153, 3 (1987), a 3.2 kb circular plasmid, by standard recombinant DNA techniques. pZ27Z10 contains the 5' transcriptional regulatory region from a maize 27 kD-zein gene (D. E. Geraghty, Ph.D. Thesis, University of Minnesota (1987)), referred to as z27 in this document), positioned immediately adjacent to the coding sequence and 3' noncoding sequence from a maize 10 kD-zein gene (Kirihara et al., *Gene*, 7, 359 (1988)), referred to as z10 in this document). The combination of the z27 regulatory sequence and z10 coding and 3' sequences is referred to as the chimeric z27-z10 gene in this document. The poly A signal from the region of the CaMV genome adjacent to the 35S promoter is positioned 3' to the z10 gene sequences in pZ27Z10. FIG. 7 depicts a map of this plasmid.

A sample of plasmid pZ27Z10 has been deposited in the American Type Culture Collection, Rockville, Md., under the provisions of the Budapest Treaty under accession number ATCC 40938.

III. DNA Delivery Process

Tissue from the maize embryogenic callus line AB63S was subcultured 3 weeks prior to microprojectile bombardment. The tissue was prepared for bombardment by sieving it through a 1.9 mm screen. The sieved tissue was plated onto sterile 5.5 cm Whatman No. 1 filter disks as a thin lawn of approximately 500 mg of tissue per filter disk. A total of 6 disks of tissue were prepared. Prior to microprojectile bombardment the filter disks containing the tissue were transferred to empty petri plates. The tissue was dehydrated slightly by allowing the plates to stand uncovered in a laminar flow hood for 20 minutes. To prevent further dehydration of the tissue, the plates were stored in a high humidity box until used for bombardment.

The DNA used in the bombardment consisted of a 1:1:1 mixture (by weight) of the plasmids pHYGI1, pZ27Z10 and pBII221. Precipitation of the DNA onto tungsten particles was carried out as described in Example I.

The bombardments were carried out as described in Example I except that the Biolistic™ PDS 1000 (DuPont) instrument was used, and no screen was placed over the tissue. The six filter disks with callus tissue were treated as follows: two filters were bombarded two times each with the DNA/tungsten preparation (potential positive treatment 2X); three filters were bombarded one time each with the DNA/tungsten preparation (potential positive treatment 1X); one filter was bombarded once with a tungsten/water suspension using the same weight of tungsten used in the DNA/tungsten bombardments (negative control treatment).

IV. Selection of Transformed Callus

After bombardment, the filter disks with callus tissue from the 2X DNA treatment were transferred to round 1 selection plates: F medium containing 15 mg/l hygromycin. Two of the filters from the 1X DNA treatment and the filter from the negative control treatment were also transferred to round 1 selection medium. The third filter from the 1X DNA treatment was transferred to F medium containing no hygromycin, for use as unselected control callus. Since this unselected control callus was potentially positive, it was only maintained for the first two rounds of selection for comparative purposes; subsequently, non-bombarded AB63S callus maintained on F medium without hygromycin was used as unselected control callus.

After five days the callus was transferred in small clumps (about 25 mg) from the filter disks onto fresh round 1 selection medium. The plating density was 10 callus clumps per plate. By this time the callus had increased approximately two-fold in weight. The unselected control callus was transferred in the same manner to F medium without hygromycin. At nineteen days post-bombardment, all of the tissue was transferred from round 1 selection medium to round 2 selection medium (F medium containing 60 mg/l hygromycin). The plating density was 14 callus clumps per plate at this transfer. The callus had increased approximately three-fold in volume during the 14 days since the previous transfer. After 23 days, all of the callus was transferred from round 2 selection medium to round 3 selection medium containing 60 mg/l hygromycin.

At 59 days post-bombardment, five live sectors were observed proliferating among the surrounding necrotic callus clumps. These five sectors were thought to have been derived from a single callus clump from the round 2 selection, since they appeared adjacent to one another on consecutive plates from the previous transfer. These sectors arose from a 2X DNA treatment and were designated as callus line Met1.

The callus line Met1 was transferred to F medium containing 60 mg/l hygromycin and to F medium without hygromycin. After 22 days of incubation, there was no visible difference in growth or appearance of the tissue on the two types of media. The callus line Met1 grew rapidly and appeared to be uninhibited by the presence of the hygromycin in the medium. The Met1 callus appeared highly friable and embryogenic on either medium, and was visually indistinguishable from control AB63S callus grown on F medium without hygromycin.

V. Confirmation of Transformed Callus

An inhibition study was performed using Met1 callus and control AB63S callus. Prior to initiating the inhibition study, Met1 callus was grown for 21 days on F medium without hygromycin. Callus of Met1 and control AB63S callus was transferred onto plates of F medium containing 0, 15, 60, 100 and 200 mg/l hygromycin. Three plates of each callus line were prepared for each concentration of hygromycin; each plate contained 5 or 6 pieces of callus at approximately 50 mg per piece (total callus per plate was approximately 300 mg).

After 28 days of incubation, the weight of callus on each plate was measured. A measure of percent growth inhibition was determined by dividing the average weight of callus obtained at each hygromycin concentration by the average weight of callus obtained at 0 mg/l hygromycin. The results showed that the growth of Met1 callus was completely uninhibited at hygromycin concentrations of 15, 60 and 100 mg/l. The growth of Met1 callus was approximately 20% inhibited on medium containing 200 mg/l hygromycin. In contrast, the growth of AB63S callus was inhibited at all concentrations of hygromycin; at 200 mg/l hygromycin, AB63S callus was 90% inhibited in growth. These results confirmed that the callus line Met1 exhibited resistance to the presence of hygromycin in the growth medium.

Southern blot analysis was carried out to verify the presence of the hygromycin resistance gene in Met1 callus DNA and to determine whether the callus had also acquired the chimeric z27-z10 gene. For detection of the HPT coding sequence, DNA samples isolated from Met1 callus and from control callus were digested with the restriction enzymes BamHI, HindIII and BstEII. The digested DNA samples were subjected to electrophoresis on a 0.8% agarose gel and blotted to a Nytran membrane as described in Example I. Visual inspection of the ethidium bromide-stained gel prior to blotting indicated that the BamHI digestions appeared to be complete, whereas neither HindIII nor BstEII cleaved the DNA samples to a significant degree. The blot was probed with a biotin-labeled 1.05 kb BamHI fragment from the HPT coding sequence. The conditions used for hybridization, washing and detection were as suggested in a BRL Photogene™ kit used in this experiment.

After hybridization, labeled bands were observed in the lanes containing BamHI digested Met1 DNA at the expected size of 1.05 kb as well as at sizes of approximately 2.7, 4.5 and 6.5 kb. This result showed that the HPT coding sequence was present in DNA from the callus line Met1. The additional bands at 2.7, 4.5 and 6.5 kb indicated that either the restriction enzyme digestion was incomplete, or that multiple rearranged copies of the HPT sequence were present. For the HindIII and BstEII digests, hybridization signals were visible in both lanes at the position of undigested DNA. This result indicated that the HPT coding sequence was integrated into high molecular-weight DNA in the Met1 genome. No hybridization signals were observed in any of the lanes containing digestions of DNA from control callus.

For detection of the chimeric z27-z10 gene, Southern blot analysis was carried out using DNA samples isolated from Met1 callus and control callus. The DNA samples were digested with the restriction enzymes BamHI and EcoRI. A BamHI digestion liberates a 2.76 kb fragment containing the z10 coding sequence and 3' noncoding sequence from the pZ27Z10 construction used in this transformation. There is a single EcoRI site in the 7.26 kb pZ27Z10 plasmid. The blot prepared was hybridized with a biotin-labeled probe containing the entire z10 coding sequence, using the conditions described in a Photogene kit (BRL).

For the BamHI digestions, endogenous z10 sequences gave hybridization signals at 9 kb and at approximately 15 kb in the lanes containing both Met1 and control callus DNAs. An additional band was observed at approximately 3.5 kb in the Met1 sample but not in the control DNA samples. No strong hybridization signal was observed at the expected 2.76 kb size in Met1 DNA. The lack of a labeled band of 2.76 kb in the BamHI digestion of Met1 DNA indicated either incomplete digestion of the DNA, or rearrangement of the introduced DNA.

For the EcoRI digestions, endogenous z10 sequences gave hybridization signals at approximately 12 kb and 16 kb in both Met1 and control callus DNAs. An additional band was observed at approximately 14 kb in the Met1 sample but not in the control callus DNA samples. These results indicated that novel z10 sequences were present in DNA from Met1 callus that were absent from control callus DNA samples.

These results were confirmed by a second Southern blot analysis in which Met1 and control callus DNAs were digested with BamHI, NcoI and NsiI. Also included were samples of undigested DNA from Met1 and control callus. The filter was probed with a $^{32}$P-labeled z10 coding sequence probe. In all of the digestions, novel z10 hybridization signals were observed in Met1 callus DNA that were absent in the negative control callus DNA samples. These results confirmed that novel z10 coding sequences were present in the Met1 callus. In the lanes containing undigested DNA, hybridization signals were observed at the position of undigested DNA from both Met1 and control callus. These results indicated that the introduced z10 sequences were integrated into chromosomal DNA in Met1 callus.

VI. Plant Regeneration and Production of Transgenic Seed

Callus from the line Met1 and from the control line AB63S was placed on RM5 medium as described in Example I. After 14 days of incubation at 26° C. in the dark, the callus was transferred to R5 medium as in Example I. The callus was incubated at 26° C. in the dark for 7 days, and then transferred to the light under the conditions described in Example I. After 14 days in the light, plantlets were transferred to Magenta boxes (Sigma Chemical Co.) containing 100 ml of R5 medium. After 7–14 days on this medium, plantlets were transferred to vermiculite for 7 days and then to soil where they were grown to maturity. A total of 49 plants (designated Met1-1 through Met1-49) were regenerated from Met1 callus, and a total of 25 plants were regenerated from control AB63S callus.

Figure 8:
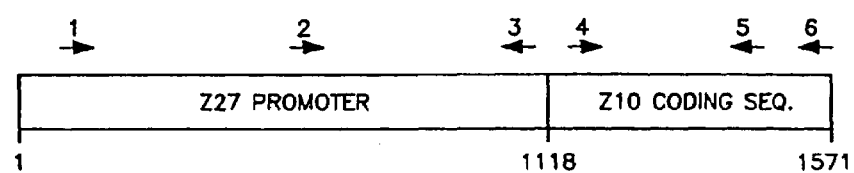
FIG. 8 is a schematic depiction of the location of the PCR primers within the chimeric z27-z10 gene.

PCR analysis was carried out on samples of DNA prepared from leaf tissue to verify that the plants regenerated from Met1 callus had retained the introduced DNA. For this purpose, a set of six oligodeoxyribonucleotides were used. The sequences of these oligonucleotides, their orientations and relative positions within the chimeric z27-z10 gene construction shown in FIG. 8 are summarized in Table 4 below.

TABLE 4

I. OLIGONUCLEOTIDE NAMES/POSITIONS IN CHIMERIC Z27–Z10 GENE:

| 1. | Z27-5' | nt | 132–156 |
| 2. | Z27-MID | nt | 628–651 |
| 3. | Z27-3' | nt | 1081–1104 |
| 4. | Z10-5' | nt | 1182–1206 |
| 5. | Z10-MID | nt | 1420–1444 |
| 6. | Z10-3' | nt | 1548–1571 |

II. AMPLIFIED FRAGMENT SIZES FROM OLIGONUCLEOTIDE PAIRS:

A. ENDOGENOUS OR CHIMERIC GENE PAIRS:

| (1) + (3) | 972 BP |
| (2) + (3) | 476 BP |
| (4) + (6) | 389 BP |
| (4) + (5) | 262 BP |

B. CHIMERIC GENE-SPECIFIC PAIRS:

| (1) + (6) | 1439 BP |
| (1) + (5) | 1312 BP |
| (2) + (6) | 943 BP |
| (2) + (5) | 816 BP |

The set of oligonucleotides (or primers) was designed such that the use of a pair of oligonucleotides consisting of one z27 oligonucleotide (z275' or z27mid) and one z10 oligonucleotide (z10mid or z103') would result in amplification of fragments from the chimeric z27-z10 gene only, and not from endogenous maize z27 or z10 genes. The appearance of amplified fragments of the expected sizes in PCR reactions using these z27-z10-specific oligonucleotide pairs were diagnostic for the presence of the chimeric z27-z10 gene in a particular callus or plant DNA sample.

The use of a pair of z27 oligonucleotides (z275' or z27mid with z273') or a pair of z10 oligonucleotides (z105' with z10mid or z103') resulted in amplification of fragments representing z27 regulatory sequences or z10 coding sequences, respectively, when used in PCR reactions carried out with control AB63S callus DNA, Met1 callus DNA or pZ27Z10 plasmid DNA. These reactions served as positive controls for amplification of endogenous maize gene sequences from a particular callus or plant DNA sample.

Leaf DNA was prepared from two Met1 R0 plants (designated Met1-1 and Met1-2) and from one control AB63S R0 plant as described hereinbelow. PCR reactions were carried out with these DNA samples using the oligonucleotide pairs specific for the HPT coding sequence, the chimeric z27-z10 gene, the z27 regulatory sequence and the z10 coding sequence. Gel analysis of the PCR reaction products showed that the expected size amplification products were obtained in all reactions using Met1-1 DNA and Met1-2 DNA. Control AB63S DNA was negative for the HPT coding sequence and for the chimeric z27-z10 gene, but positive for the endogenous z27 regulatory sequence and z10 coding sequence. These results demonstrated that the Met1 R0 plants examined had retained the introduced HPT DNA and the chimeric z27-z10 DNA.

As corroborative proof that the diagnostic z27-z10 PCR reaction products contained both z27 regulatory sequences and z10 coding sequences, Southern blot analysis was carried out on the PCR reaction products. Southern blot filters were prepared from two agarose gels loaded with identical samples. The samples contained the PCR reaction products resulting from amplification of z27 regulatory sequences, z10 coding sequences, and chimeric z27-z10 gene sequences described above. One blot was hybridized with a z10 coding sequence probe and the other blot was hybridized with a z27 regulatory sequence probe. The results showed that the z10 coding sequence probe hybridized to the amplified fragments from the z10 coding sequence PCR reactions and the chimeric z27-z10 gene nCR reactions, but not to the amplified fragments from the z27 regulatory sequence PCR reactions. Analogously, the z27 probe hybridized to the amplified fragments from the z27 regulatory sequence PCR reactions and the chimeric z27-z10 gene PCR reactions but not to the amplified fragments from the z10 coding sequence PCR reactions. These results demonstrated that the fragments amplified in the PCR reactions contained the expected gene sequences and that the diagnostic PCR amplification product for the chimeric z27-z10 gene contained both z27 regulatory sequences and z10 coding sequences.

Controlled pollinations of mature Met1 R0 plants were carried out with inbred maize lines A188, B73, A654 and H99. In addition, several self- and sib-pollinations were carried out. A total of 130 pollinations were carried out, using Met1 R0 plants as both male pollen donors and as female pollen recipients. Mature seed was harvested at 45 days post-pollination and allowed to dry further for 1–2 weeks.

VII. Analysis of the R1 Progeny

The presence of the HPT sequence and the chimeric z27-z10 gene were evaluated by PCR analysis of DNA from R1 plant tissues, in three sets of R1 progeny.

The first set of R1 progeny analyzed consisted of four immature tassel-seeds from R0 plant Met1-7. These tassel-seeds were obtained through open pollination of silks developing from the tassel of Met1-7. Approximately 18 days after pollination, the tassel-seeds were removed from the plant and surface-sterilized. The endosperm from each seed was excised and frozen on dry ice and stored at −70° C. until used for DNA isolation.

The embryo from each seed was transferred to R5 medium and allowed to germinate. After 10 days, the seedlings were transferred to vermiculite for 7 days and then to soil, where they were allowed to grow to maturity. PCR analysis was carried out on DNA isolated from each endosperm using oligonucleotide sets specific for the HPT coding sequence, the chimeric z27-z10 gene and the maize Adh-1 gene. Three of the four endosperm DNA samples were found to be positive for all of the above gene sequences. The fourth endosperm DNA sample was negative for the HPT coding sequence and the chimeric z27-z10 gene sequence but positive for the endogenous Adh-1 sequence. These results showed that both the HPT sequence and the chimeric z27-z10 gene had been transmitted to R1 progeny of Met1-7.

A similar analysis was carried out with 24 seeds from the cross A654 X Met1-1. At 24 days after pollination, the seeds were removed from the ear and surface-sterilized. Endosperms and embryos were isolated and treated as described above. PCR analysis of the endosperm DNA samples showed that 9 of the 24 progeny had received both the HPT sequences and the chimeric z27-z10 gene. The remaining 15 progeny carried neither of the introduced gene sequences. The third set of R1 progeny analyzed consisted of 28 R1 plants derived from self-pollination of R0 plant Met1-6. DNA samples were prepared from leaf tissue of 28 two-week old seedlings.

PCR analysis of the leaf DNA samples showed that 24 of the R1 progeny carried both the HPT sequences and the chimeric z27-z10 gene. The remaining 4 R1 progeny carried neither of the introduced gene sequences. The results of the analyses described above are summarized in Table 5 and demonstrate that a significant proportion of the R1 progeny of Met1 plants inherited the introduced DNA.

TABLE 5

Inheritance of the Introduced HPT Sequences and the Chimeric Z10 Gene in Progeny from Crosses of Met1 Plants

| Genotype | Outcross (A654 × Met1-1) No. Progeny | Self-Pollination (Met1-6) No. Progeny |
| --- | --- | --- |
| HPT+/z27z10+ | 9/24 | 24/28 |
| HPT+/z27z10− | 0/24 | 0/28 |
| HPT−/z27z10+ | 0/24 | 0/28 |
| HPT−/z27z10− | 15/24 | 4/28 |

The ratio of z27z10+/HPT+ plants to z27z10−/HPT− plants from the outcross population is consistent with a 1:1 segregation ratio of a single locus. In addition, the ratio of z27z10+/HPT+ plants to z27z10−/HPT− plants from the self-pollinated population is consistent with a 3:1 segregation ratio of a single locus. The data also indicate linkage of the introduced HPT and z27-z10 sequences.

EXAMPLE III

Fertile Transgenic Plants from Callus Line AB12 Containing Recombinant DNA Encoding an Insecticidal Protein The proteins encoded by the various *Bacillus thuringiensis* genes have been shown to be useful in a number of pesticidal applications. Production of transgenic maize plants with specific heterologous Bt genes may improve the resistance of the plants to specific pests. Fertile transgenic plants containing a recombinant Bt gene were prepared according to the procedure of Example I, with several minor modifications, as indicated below.

At the same time AB11, the callus line of Example I, was initiated, another callus line was also prepared. AB12 was prepared from a separate cross of plants with the same parental genotype (A188 ×B73). This example demonstrates the regeneration of fertile transgenic plants from a third callus line in addition to AB11 and AB63S, and demonstrates that the production of fertile transgenic plants was not the result of properties unique to a single callus line.

The plasmid pHYGI1 described in Example I was used, as well as pMS533, which is a plasmid that contains the insecticidal *Bacillus thuringiensis* endotoxin (BT) gene fused in frame with the neomycin phosphotransferase (NP-TII) gene. At a position 5′ from the fusion gene are located segments of DNA from the CaMV and nopaline synthase promoters. At a position 3′ from the fusion gene are segments of DNA derived from the tomato protease inhibitor I gene and the poly A region of the nopaline synthase gene.

Callus was bombarded as described in Example I except that the DNA used in the tungsten/DNA preparations contained plasmids pHYGI1 and pMS533. One tube contained only 5 μl TE (10 mM Tris-HCl pH 8.0, 1 mM EDTA).

The following bombardments were done: 11×pHYGI1/pMS533 (potential positive treatment) and 3×TE prep (control treatment).

After bombardment, the callus from the pHYGI1/pMS533 treatments was placed onto round 1 selection plates, F medium containing 15 mg/l hygromycin as ten pieces per plate. The same was done for two of the plates bombarded with the TE preparation (selected control callus). One plate of callus bombarded with the TE preparation was placed onto F medium with no hygromycin; this callus was maintained throughout the experiment as a source of control tissue (unselected control callus).

After 18 days, the callus was transferred from round 1 selection plates to round 2 selection plates containing 60 mg/l hygromycin as ten 30 mg pieces per plate. After 21 days of selection on round 2 selection plates, the callus appeared completely inhibited. All of the callus was transferred from round 2 selection plates to round 3 selection plates containing 60 mg/l hygromycin.

After 42 days on round three selection plates, six sectors were observed proliferating from the surrounding necrotic tissue, all were from pHYGI1/pMS533-treated material. The callus lines were transferred to F medium.

After 24 days, one callus line, designated CB2, had grown substantially. Portions of each callus line were then transferred to (i) F medium containing 15 mg/l hygromycin, or (ii) F medium containing 60 mg/l hygromycin. Control callus was plated on F medium with 15 mg/l hygromycin.

Only one of the six callus lines, CB2, was capable of sustained growth through multiple subcultures in the presence of 60 mg/l hygromycin. DNA was isolated from portions of this callus and the presence of the Bt gene was confirmed by Southern blot analysis.

DNA was digested with the restriction enzymes BamHI and XhoI in combination. BamHI cuts at the 5′ end of the Bt coding sequence and XhoI cuts at the 3′ end of the coding region. A $^{32}$P labeled probe was prepared from the 1.8kb BamHI/XhoI restriction fragment of pMS533. The predicted 1.8 kb band was observed after hybridization and autoradiography. No bands were observed in the DNA from the untransformed callus.

Plants were regenerated from CB2 and controlled pollinations were performed to yield the R1 generation, as described hereinabove. R1 plants were tested for the presence of the HPT and Bt gene sequences by PCR analysis, and for HPT gene expression by enzyme assay as described in Example I.

PCR analysis was performed on DNA isolated from root tissue of R1 seedlings by the methods described in Example I. To test that each DNA sample was competent for PCR, PCR analysis was carried out using primers specific for the native maize 10 kD zein gene. The primers used for PCR analysis of the Bt gene were one complementary to the 35S promoter and one complementary to the Bt coding sequence. Primers used for HPT PCR analysis were the same as those described in Example I. The results of this analysis are presented in Table 6. The results show transmission of the introduced HPT and Bt genes through both the male and female parents and the observed frequencies are consistent with Mendelian inheritance. The results are consistent with the insertion of the HPT and Bt genes into chromosomal DNA. It was also found that the HPT and Bt genes show a linked inheritance, indicating that the two genes are inserted close together on the same chromosome.

TABLE 6

Analysis of R1 Progeny of CB2

| | A. Transgenic CB2.8 × FR4326 Analysis | | | | | Control AB12.7 × FR4326 Analysis | | | |
|---|---|---|---|---|---|---|---|---|---|
| Plant | 10Kd PCR | HPT PCR | BT PCR | HPT ENZ. | PLANT | 10Kd PCR | HPT PCR | BT PCR | HPT ENZ. |
| 1 | + | + | + | + | 1 | + | − | − | − |
| 2 | + | + | + | + | 2 | + | − | − | − |
| 3 | + | − | − | − | | | | | |
| 4 | + | + | + | + | | | | | |
| 5 | + | + | + | + | | | | | |
| 6 | + | − | − | − | | | | | |
| 7 | + | + | + | + | | | | | |
| 8 | + | − | − | − | | | | | |
| 9 | + | + | + | + | | | | | |
| 10 | + | − | − | − | | | | | |

| | B. Transgenic B2.11 × LB101 Assays | | | | | Control AB12.4 × LB101 Assays | | | |
|---|---|---|---|---|---|---|---|---|---|
| Plant | 10Kd PCR | HPT PCR | BT PCR | HPT ENZ. | PLANT | 10Kd PCR | HPT PCR | BT PCR | HPT ENZ. |
| 1 | + | − | − | − | 1 | + | − | − | − |
| 2 | + | + | + | + | 2 | + | − | − | − |
| 3 | + | − | − | − | | | | | |
| 4 | + | + | + | + | | | | | |
| 5 | + | − | − | − | | | | | |
| 6 | + | + | + | + | | | | | |
| 7 | + | − | − | − | | | | | |
| 8 | + | − | − | − | | | | | |
| 9 | + | − | − | − | | | | | |
| 10 | + | − | − | + | | | | | |

| | C. Transgenic CB2.7 × LM1112 Assays | | | | Control AB12.5 × LM1112 Assays | | |
|---|---|---|---|---|---|---|---|---|
| Plant | 10Kd PCR | HPT PCR | BT PCR | PLANT | 10Kd PCR | HPT PCR | BT PCR |
| 1 | + | − | − | 1 | + | − | − |
| 2 | + | + | + | 2 | + | − | − |
| 3 | + | − | − | | | | |
| 4 | + | − | − | | | | |
| 5 | + | + | + | | | | |
| 6 | + | + | + | | | | |
| 7 | + | + | + | | | | |
| 8 | + | + | + | | | | |
| 9 | + | − | − | | | | |
| 10 | + | − | − | | | | |

| | D. Transgenic FR4326 × CB2.9 Assays | | | | Control FR4326 × AB12.1 Assays | | |
|---|---|---|---|---|---|---|---|---|
| Plant | 10Kd PCR | HPT PCR | BT PCR | PLANT | 10Kd PCR | HPT PCR | BT PCR |
| 1 | + | − | − | 1 | + | − | − |
| 2 | + | + | + | 2 | + | − | − |

TABLE 6-continued

| | | | |
|---|---|---|---|
| 3 | + | + | + |
| 4 | + | + | + |
| 5 | + | + | + |
| 6 | + | − | − |
| 7 | + | + | + |
| 8 | + | + | + |
| 9 | + | − | − |
| 10 | + | − | − |

| E. Transgenic A188 × CB2.1 Assays | | | | Control A188 × AB12.2 Assays | | | |
|---|---|---|---|---|---|---|---|
| Plant | 10Kd PCR | HPT PCR | BT PCR | PLANT | 10Kd PCR | HPT PCR | BT PCR |
| 1 | + | + | + | 1 | + | − | − |
| 2 | + | + | + | 2 | + | − | − |
| 3 | + | + | + | | | | |
| 4 | + | − | − | | | | |
| 5 | + | + | + | | | | |
| 6 | + | − | − | | | | |
| 7 | + | + | + | | | | |
| 8 | + | + | + | | | | |
| 9 | + | − | − | | | | |
| 10 | + | − | − | | | | |

| F. Transgenic LM1112 × CB2.2 Assays | | | | Control LM112 × AB12.6 Assays | | | |
|---|---|---|---|---|---|---|---|
| Plant | 10Kd PCR | HPT PCR | BT PCR | PLANT | 10Kd PCR | HPT PCR | BT PCR |
| 1 | + | − | − | 1 | + | − | − |
| 2 | + | − | − | 2 | + | − | − |
| 3 | + | − | − | | | | |
| 4 | + | − | − | | | | |
| 5 | + | − | − | | | | |
| 6 | + | − | − | | | | |
| 7 | + | − | − | | | | |
| 8 | + | + | + | | | | |

EXAMPLE IV

Fertile Transgenic Plants from Callus Line AB12 Transmitting Recombinant DNA through Two Complete Sexual Cycles I. Plant Lines and Tissue Culture The callus line AB12 was used, and is described in Example III.

II. Plasmids

The plasmids pBII221 and pHYGI1 described in Example I were used.

III. DNA Delivery Process

Callus was bombarded as in Example I, except that the DNA used in the tungsten/DNA preparations differed. All of the tubes contained 25 µl 50 mg/ml M-10 tungsten in water, 25 µl 2.5 M CaCl$_2$, and 10 µl 100 mM spermidine along with a total of 5 µl 1 mg/ml total plasmid content. One tube contained only plasmid pBII221; two tubes contained only plasmid pHYGI1; and one tube contained no plasmid but 5 µl TE buffer.

The following bombardments were done: 2×pBII221 prep (for transient expression); 7×pHYGI1 prep (potential positive treatment); and 3×TE prep (negative control treatment).

After all the bombardments were performed, the callus from the pBII221 treatment was transferred plate for plate to F medium as five 50 mg pieces. After 2 days, the callus was placed into GUS assay buffer as per Example I. Numbers of transiently expressing cells were counted and found to be 686 and 845 GUS positive cells, suggesting that the particle delivery process had occurred in the other bombarded plates.

IV. Selection of Transformed Callus

After bombardment, the callus from the pHYGI1 treatments was placed onto round 1 selection plates, F medium containing 15 mg/l hygromycin, as ten 25 mg pieces per plate. The same was done for two of the plates bombarded with the TE preparation (selected control callus). One plate of callus bombarded with the TE preparation was placed onto F medium with no hygromycin; this callus was maintained throughout the experiment as a source of control tissue (unselected control callus).

After 13 days, the callus on round 1 selection plates was indistinguishable from unselected control callus. All of the callus was transferred from round 1 selection plates to round 2 selection plates containing 60 mg/l hygromycin. An approximate five-fold expansion of the numbers of plates occurred.

The callus on round 2 selection plates had increased substantially in weight after 23 days, but at this time appeared close to necrotic. All of the callus was transferred from round 2 selection plates to round 3 selection plates containing 60 mg/l hygromycin.

At 58 days post-bombardment, three live sectors were observed proliferating from the surrounding dead tissue. All three lines were from pHYGI1 treatments and were designated 24C, 56A, and 55A.

After 15 days on maintenance medium, growth of the lines was observed. The line 24C grew well whereas lines 55A and 56A grew more slowly. All three lines were transferred to F medium containing 60 mg/l hygromycin. Unselected control callus from maintenance medium was also plated to F medium containing 60 mg/l hygromycin.

After 19 days on 60 mg/l hygromycin, the growth of line 24C appeared to be entirely uninhibited, while the control showed approximately 80% of the weight gain of 24C. The line 56A was completely necrotic, and the line 55A was very close to necrotic. The lines 24C and 55A were transferred again to F medium containing 60 mg/l hygromycin, as was the control tissue.

After 23 days on 60 mg/l hygromycin, the line 24C again appeared entirely uninhibited. The line 55A was completely dead, as was the negative control callus on its second exposure to F medium having 60 mg/l hygromycin.

V. Confirmation of Transformed Callus

Figure 6:
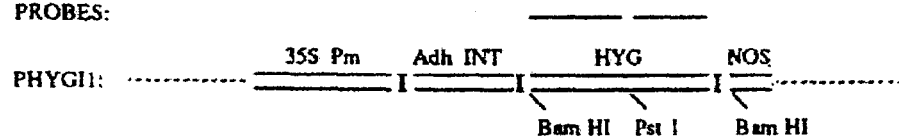
FIG. 6 is a Southern blot of DNA isolated from the PH2 callus line and an untransformed control callus line, and a schematic depiction of the pHYGI1 probes used in the assay.
Figure 6:
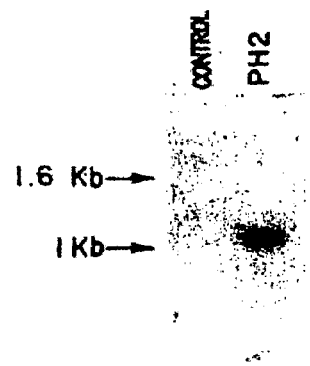

A Southern blot was prepared from BamHI-digested DNA from the line 24C and probed with the HPT probe described in Example I. As shown in FIG. 6, a band was observed for the line 24C at the expected size of 1.05 kb showing that the line 24C contained the HPT coding sequence. No band was observed for DNA from control tissue. The name of the callus line 24C was changed to PH2.

To demonstrate that the hygromycin gene is incorporated into high molecular weight DNA, DNA isolated from PH2 callus and control callus was treated with (i) no restriction enzyme, (ii) BamHI, as described previously, or, (iii) PstI, which cuts the plasmid pHYGI1 only once within the HPT coding sequence. Samples were blotted and probed with the HPT coding sequence as described previously.

Undigested PH2 DNA only showed hybridization the probe at the position of uncut DNA, demonstrating that the hygromycin gene is incorporated into high molecular weight DNA. The expected 1.05 kb band for PH2 DNA digested with BamHI was observed, as had been shown previously. For PH2 DNA digested with PstI, a 5.9 kb band would be expected if the hygromycin gene was present on an intact pHYGI1 plasmid. Two or more bands of variable size (size dependent on the position of flanking PstI sites within the host DNA) would be expected if the gene was integrated into genomic DNA. Two bands were observed with approximate molecular sizes of 6.0 and 3.0 kb. These data are consistent with incorporation of the hygromycin gene into high molecular weight DNA. No hybridization was observed for DNA from control callus in any of the above treatments.

These results demonstrate that the HPT coding sequence is not present in PH2 callus as intact pHYGI1 or as a small non-chromosomal plasmid. They are consistent with incorporation of the hygromycin gene into high molecular weight DNA. Further Southern blot analyses demonstrated that the HPT coding sequence is contiguous with the 35S promoter sequence.

VI. Plant Regeneration and Production of Seed

The line PH2, along with unselected control callus, was placed onto RM5 medium to regenerate plants as in Example I. After 16 days, the callus was transferred to R5 medium as in Example I. After 25 d on R5 medium, plantlets were transferred to R5 medium and grown up for 20 days. At this point, plantlets were transferred to vermiculite for one week and then transplanted into soil where they were grown to sexual maturity. Controlled pollinations were then performed with the inbred line B73.

VII. Analysis of R1 Progeny

A. PH2 as Pollen Donor

Ten R1 progeny plants from a B73 ×PH 2.6 cross were assayed for HPT expression with both root elongation and etiolated leaf assays. One positive plant was identified. The presence of the HPT gene in the positive plant was confirmed by Southern blot analysis employing the HPT probe as described in Example I.

To conduct the root elongation bioassay, seed was sterilized in a 1:1 dilution of commercial bleach in water plus 0.1% Alconox for 20 min. in 125 ml Erlenmeyer flasks and rinsed 3 times in sterile water. The seeds were imbibed overnight in sterile water containing 50 mg/ml Captan by shaking at 150 rpm.

After imbibition, the solution was decanted from the flasks and the seed transferred to flow boxes (Flow Laboratories) containing 3 sheets of $H_2O$ saturated germination paper. A fourth sheet of water saturated germination paper was placed on top of the seed. Seed was allowed to germinate 4 days.

After the seed had germinated, approximately 1 cm of the primary root tip was excised from each seedling and plated on medium containing MS salts, 20 g/l sucrose, 50 mg/l hygromycin, 0.25% Gelrite, and incubated in the dark at 26° C. for 4 days.

Roots were evaluated for the presence or absence of abundant root hairs and root branches. Roots were classified as transgenic (hygromycin resistant) if they had root hairs and root branches, and untransformed (hygromycin sensitive) if they had limited numbers of branches.

After the root tips were excised, the seedlings of one PH2 ear and one control ear were transferred to moist vermiculite and grown in the dark for 5 days. At this point, to conduct an etiolated leaf bioassay, 1 mm sections were cut from the tip of the coleoptile, surface sterilized 10 seconds, and plated on MS basal salts, 20 g/l sucrose, 2.5 g/l Gelrite with either 0 (control) or 100 mg/l hygromycin and incubated in the dark at 26° C. for 18 hrs. Each plate contained duplicate sections of each shoot. The plates were then incubated in a light regimen of 14 hrs light 10 hrs dark at 26° C. for 48 hrs, and rated on a scale of from 0 (all brown) to 6 (all green) for the percent of green color in the leaf tissue. Shoots were classified as untransformed (hygromycin sensitive) if they had a rating of zero and classified as transformed (hygromycin resistant) if they had a rating of 3 or greater.

B. PH2 as Pollen Recipient

80 R1 progeny plants from a PH2 plant designated PH 2.23 ×B73 cross were assayed for HPT expression by root elongation assay and 26 tested positive. The expression of the HPT gene was further confirmed for all 26 by direct exposure of seedlings to hygromycin-containing medium in Flow boxes. Two of the resistant plants were analyzed by PCR, and the presence of the HPT sequence was confirmed.

VIII. Analysis of R2 Progeny

The transgenic R1 plant which had PH2 as the pollen parent was grown to maturity and used to pollinate an FR4326 plant.

R2 seeds from this cross were germinated and tested for the presence of HPT sequences by PCR. Expression of the HPT gene was determined with the HPT enzymatic assay described in Example I.

Three of the 19 progeny tested contained HPT gene sequences and also expressed the HPT enzyme activity. The remainder neither contained HPT sequences nor showed enzyme activity. This result demonstrates pollen transmission and expression of the genetically engineered DNA through 2 successive generations, indicating that the gene is stable.

EXAMPLE V

The friable, embryogenic maize callus culture AB12 described in Example III was used.

The plasmids pCHN1-1 and pLUC-1 were constructed in the vector pBS+ (Stratagene, Inc., San Diego, Calif.), a 3.2 Kb circular plasmid, using standard recombinant DNA techniques. pCHN1-1 contains the hygromycin B phosphotransferase (HPT) coding sequence from *E. coli* (Gritz et al. 1983) flanked at the 3' end by the nopaline synthase (nos) polyadenylation sequence of *Agrobacterium tumefaciens* (Chilton and Barnes 1983). Expression is driven by the cauliflower mosaic virus (CaMV) 35S promoter (Guilley et al. 1982), located upstream from the HPT coding sequence. The plasmids pBI1221 and pHYGI1 were also used in this example.

pLUC-1 contains the firefly luciferase coding sequence (DeWet et al. 1987) flanked at the 5' end by the CaMV 35S promoter and at the 3' end by the nos polyadenylation sequence. This plasmid was used solely as negative control DNA. Plasmids were introduced into AB12 by microprojectile bombardment. Twenty-six plates were prepared as described in Example I. One tube contained only plasmid pBII221; two tubes contained both plasmids pHYGI1 and pBII221; two tubes contained both plasmids pCHN1-1 and pBII221; and one tube contained only plasmid pLUC-1. The bombardments which were performed are summarized on Table 7.

TABLE 7

| | |
|---|---|
| 2 × pBII221 prep | To determine transient expression frequency |
| 10 × pHYGI1/pBII221 | As a potential positive treatment for transformation |
| 10 × pCHN1-1/pBII221 | As a potential positive treatment for transformation |
| 4 × pLUC-1 | Negative control treatment |

The two plates of callus bombarded with pBII221 were assayed for transient GUS expression. The number of blue cells was counted, giving 291 and 477 transient GUS expressing cells in the two plates, suggesting that the DNA delivery process had also occurred with the other bombarded plates.

Immediately after all samples had been bombarded, callus from all of the plates treated with pHYGI1/pBII221, pCHN1-1/pBII221 and three of the plates treated with pLUC-1 were transferred plate for plate onto round 1 selection plates, F medium containing 15 mg/l hygromycin B, (five pieces of callus per plate). Callus from the fourth plate treated with pLUC-1 was transferred to F medium without hygromycin. This tissue was subcultured every 2–3 weeks onto nonselective medium and is referred to as unselected control callus.

After two weeks of selection, tissue appeared essentially identical on both selective and nonselective media. All callus from eight plates from each of the pHYGI1/pBII221 and pCHN1-1/pBII221 treatments and two plates of the control callus on selective media were transferred from round 1 selection plates to round 2 selection plates that contained 60 mg/l hygromycin. The round 2 selection plates each contained ten 30 mg pieces of callus per plate, resulting in an expansion of the total number of plates.

The remaining tissue on selective media, two plates each of pHYGI1/pBII221 and pCHN1-1/pBII221 treated tissue and one of control callus, were placed in GUS assay buffer at 37° C. to determine whether blue clusters of cells were observable at two weeks post-bombardment. After 6 days in assay buffer, this tissue was scored for GUS expression. The results are summarized on Table 8.

TABLE 8

| Treatment | Replicate | Observations |
|---|---|---|
| pLUC-1 | | No blue cells |
| pHYGI1/pBII221 | Plate 1 | 11 single cells |
| | | 1 four-cell cluster |
| | Plate 2 | 5 single cells |
| pCHN1-1/pBII221 | Plate 1 | 1 single cell |
| | | 2 two-cell clusters |
| | Plate 2 | 5 single cells |
| | | 1 two-cell cluster |
| | | 2 clusters of 8–10 cells |

After 21 days on the round 2 selection plates, all viable portions of the material were transferred to round 3 selection plates containing 60 mg/l hygromycin. The round 2 selection plates, containing only tissue that was apparently dead, were reserved. Both round 2 and 3 selection plates were observed periodically for viable proliferating sectors.

After 35 days on round 3 selection plates, both the round 2 and round 3 sets of selection plates were checked for viable sectors of callus. Two such sectors were observed proliferating from a background of dead tissue on plates treated with pHYGI1/pBII221. The first sector named 3AA was from the round 3 group of plates and the second sector named PH1 was from the round 2 group of plates. Both lines were then transferred to F medium without hygromycin.

After 19 days on F medium without hygromycin, the line 3AA grew very little whereas the line PH1 grew rapidly. Both were transferred again to F medium for 9 days. The lines 3AA and PH1 were then transferred to F medium containing 15 mg/l hygromycin for 14 days. At this point, line 3AA was observed to be of very poor quality and slow growing. The line PH1, however, grew rapidly on F medium with 15 mg/l hygromycin; the line was then subcultured to F medium without hygromycin.

After 10 days on F medium, an inhibition study of the line PH1 was initiated. Callus of PH1 was transferred onto F medium containing 1, 10, 30, 100, and 250 mg/l hygromycin B. Five plates of callus were prepared for each concentration and each plate contained ten approximately 50 mg pieces of callus. One plate of unselected control tissue was prepared for each concentration of hygromycin.

It was found that the line PH1 was capable of sustained growth over 9 subcultures on 0, 10, 30, 100, and 250 mg/l hygromycin.

Additional sectors were recovered at various time points from the round 2 and 3 selection plates. None of these were able to grow in the presence of hygromycin for multiple rounds, i.e., two or three subcultures.

To show that the PH1 callus had acquired the hygromycin resistance gene, a Southern blot of PH1 callus was prepared by isolating DNA from PH1 and unselected control calli by freezing 2 g of callus in liquid nitrogen and grinding it to a fine powder which was transferred to a 30 ml Oak Ridge tube containing 6 ml extraction buffer (7M urea, 250 mM NaCl, 50 mM Tris-HCl pH 8.0, 20 mM EDTA pH 8.0, 1% sarcosine). To this was added 7 ml of phenol:chloroform 1:1, the tubes shaken and incubated at 37° C. for 15 min. Samples were centrifuged at 8K for 10 min. at 4° C. The supernatant was pipetted through miracloth (Calbiochem 475855) into a disposable 15 ml tube (American Scientific Products, C3920-15A) containing 1 ml 4.4 M ammonium acetate, pH 5.2. Isopropanol, 6 ml was added, the tubes shaken, and the samples incubated at −20° C. for 15 min. The DNA was pelleted in a Beckman TJ-6 centrifuge at the maximum speed for 5 min. at 4° C. The supernatant was discarded and the pellet was dissolved in 500 μl TE-10 (10 mM Tris-HCl pH 8.0, 10 mM EDTA pH 8.0) 15 min. at room temperature. The samples were transferred to a 1.5 ml Eppendorf tube and 100 μl 4.4 M ammonium acetate, pH 5.2 and 700 μl isopropanol were added. This was incubated at −20° C. for 15 min. and the DNA pelleted 5 min. in an Eppendorf microcentrifuge (12,000 rpm). The pellet was washed with 70% ethanol, dried, and resuspended in TE-1 (10 mM Tris-HCl pH 8.0, 1 mM EDTA).

Ten μg of isolated DNA were digested with BamHI (NEB) and analyzed as described in Example I using the HPT probe. As shown in FIG. 3, a band was observed for PH1 callus at the expected position of 1.05 Kb, indicating that the HPT coding sequence was present. No band was observed for control callus.

To demonstrate that the hygromycin gene is incorporated into high molecular weight DNA, DNA isolated from PH1 callus and control callus was treated with (i) no restriction enzyme, (ii) BamHI, as described previously, or (iii) PstI, which cuts the plasmid pHYGI1 only once within the HPT coding sequence. Samples were blotted and probed with the HPT coding sequence as described previously.

Undigested PH1 DNA only showed hybridization to the probe at the position of uncut DNA, demonstrating that the hygromycin gene is incorporated into high molecular weight DNA. The expected 1.05 Kb band for PH1 DNA digested with BamHI was observed, as had been shown previously. For PH1 DNA digested with PstI, a 5.9 Kb band would be expected if the hygromycin gene was present on an intact pHYGI1 plasmid. Two or more bands of variable size (size dependent on the position flanking PstI sites within the host DNA) would be expected if the gene was incorporated into high molecular weight DNA. Three bands were observed with approximate molecular sizes of 12, 5.1, and 4.9 Kb. This result demonstrates incorporation of the hygromycin gene into high molecular weight DNA. The intensity of the 4.9 Kb band is approximately twice as great as the other two bands, suggesting either partial digestion or possibly a tandem repeat of the HPT gene. No hybridization was observed for DNA from control callus in any of the above treatments.

These results demonstrate that the HPT coding sequence is not present in PH1 callus as intact pHYGI1 or as a small non-chromosomal plasmid. They are consistent with incorporation of the hygromycin gene into high molecular weight DNA. Further, Southern blot analyses demonstrated that the HPT coding sequence is contiguous with the 35S promoter sequence.

PH1 callus was transferred from all of the concentrations of hygromycin used in the inhibition study to RM5 medium and plants were regenerated as described in Example I. A total of 65 plants were produced from PH1 and a total of 30 plants were produced from control callus.

Figure 4:
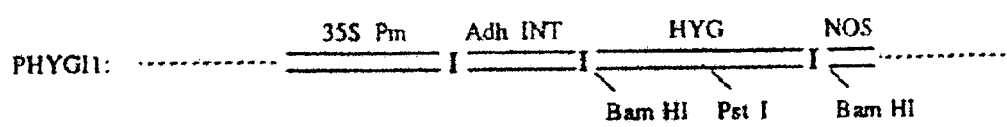
FIG. 4 is a Southern blot of leaf DNA isolated from R0 plants regenerated from PH1 and untransformed callus, and a schematic depiction of the pHYGI1 probes used in the assay.
Figure 4:
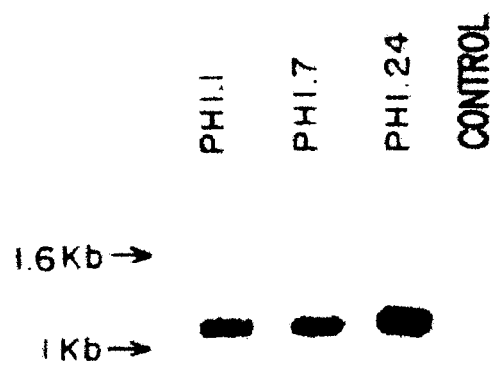

To demonstrate that the introduced DNA had been retained in the R0 tissue, a Southern blot was performed as previously described on BamHI digested leaf DNA from three randomly chosen R0 plants of PH1. The blot was probed with the HPT probe as in Example I. As shown in FIG. 4, a 1.05 Kb band was observed with all three plants indicating that the HPT coding sequence was present. No band was observed for DNA from a control plant.

Controlled pollinations of mature PH1 plants were conducted by standard techniques with inbred *Zea mays* lines A188, B73, and Oh43. Seed was harvested 45 days post-pollination and allowed to dry further 1–2 weeks.

Figure 5:
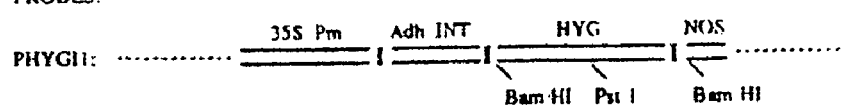
FIG. 5 is a Southern blot of leaf DNA isolated from R1 progeny of PH1 R0 plants and untransformed R0 plants, and a schematic depiction of the pHYGI1 probes used in the assay.

The presence of the hygromycin resistance trait in the R1 progeny was evaluated by the root elongation bioassay, an etiolated leaf bioassay, and by Southern blotting. Two ears each from regenerated PH1 and control plants were selected for analysis. The pollen donor was inbred line A188 for all ears. The results are shown in FIG. 5 and in Table 9, below.

TABLE 9

ANALYSIS OF PH1 R1 PLANTS

| PH1 PLANT | ROOT ASSAY | LEAF ASSAY | BLOT | CONT PLANT | ROOT ASSAY | LEAF ASSAY | BLOT |
|---|---|---|---|---|---|---|---|
| 3.1 | + | ND | + | 4.1 | − | ND | ND |
| 3.2 | − | ND | − | 4.2 | − | ND | ND |
| 3.3 | − | ND | − | 4.3 | − | ND | ND |
| 3.4 | − | ND | − | 4.4 | − | ND | ND |
| 3.5 | − | ND | − | 4.5 | − | ND | ND |
| 3.6 | + | ND | + | 4.6 | − | ND | ND |
| 3.7 | − | ND | − | 4.7 | − | ND | ND |
|  |  |  |  | 2.1 | − | ND | − |
| 10.1 | + | + | + | 1.1 | − | − | − |
| 10.2 | + | + | + | 1.2 | − | − | ND |
| 10.3 | − | − | ND | 1.3 | − | − | ND |
| 10.4 | − | − | − | 1.4 | − | − | ND |
| 10.5 | − | − | − | 1.5 | − | − | ND |
| 10.6 | − | − | − | 1.6 | − | − | ND |
| 10.7 | − | − | − | 1.7 | − | − | ND |
| 10.8 | ND | + | + | 1.8 | − | − | ND |

Key: + = transgenic; − = nontransgenic; ND = not done

The presence of the HPT gene was confirmed in two R2 progeny deriving from a PH1 maternal parent.

Plant PH1.3.1 (see Table 9) was pollinated with Oh43 pollen. Nine seeds derived from this cross were germinated, DNA was prepared from the leaves of four of the progeny plants, and analyzed by Southern blotting using the HPT coding sequence probe. Two of the four plants tested contained the HPT sequence in high copy number. Although the HPT gene was present in two of the plants, expression of the gene could not be detected in the etiolated leaf assay.

Plant PH1.10.8 (Table 9) was used to pollinate B73 and was also selfed. Fifty of the progeny from the out-cross were tested for HPT expression in both root and leaf assays. No expression was detected. Likewise Southern blots on DNA from eight of the progeny did not detect the presence of the HPT gene. In the progeny from the self cross, no evidence for the presence of the gene was obtained in leaf assays of nine progeny, or from Southern blots of the DNA from four of these plants.

The recombinant DNA was only shown to be inherited by progeny when a transgenic plant (both R0 and R1) was used as a female. This is suggestive of maternal inheritance of the recombinant DNA for PH1.

All of the publications and patent documents cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A process for producing a fertile transgenic *Zea mays* plant comprising the steps of (i) bombarding intact regenerable *Zea mays* cells with DNA-coated microprojectiles; wherein said DNA comprises a preselected DNA sequence encoding a *Bacillus thuringiensis* endotoxin, wherein the preselected DNA sequence is adjusted to be more efficiently expressed in *Zea mays* than the native *B. thuringiensis* DNA sequence encoding said endotoxin; (ii) identifying a population of transformed cells comprising said preselected DNA sequence; and (iii) regenerating a fertile transgenic plant therefrom, wherein said preselected DNA sequence is expressed so as to impart insect resistance to said transgenic plant and is heritable.

2. The process of claim 1, wherein the preselected DNA sequence encoding said endotoxin comprises an increased number of maize preferred codons compared to native *Bacillus thuringiensis* endotoxin.

3. The process of claim 1, wherein the preselected DNA sequence further comprises a protease inhibitor.

4. A population of plants obtained by breeding the transgenic plants of claim 1 wherein the preselected DNA sequence from said transgenic plant is transmitted by Mendelian inheritance through both male and female parent plants to the population of plants.

5. The process of claim 1, wherein the preselected DNA sequence further comprises a selectable marker gene or a reporter gene.

6. The process of claim 5, wherein the selectable marker gene confers resistance or tolerance to a compound selected from the group consisting of hygromycin, sethoxydim, haloxyfop, glyphosate, methotrexate, imidazoline, sufolnylurea, triazolopyrimidine, s-triazine, bromoxynil, phosphinotliricin, kanamycin, G418, 2,2-dichloropropionic acid and neomycin.

7. The process of claim 6, wherein the compound is phosphinothricin.

8. The process of claim 6, wherein the compound is kanamycin.

9. The process of claim 6, wherein the compound is hygromycin.

10. The process of claim 5, wherein the DNA sequence encoding the *Bacillus thuringiensis endotoxin is fused in frame with said selectable marker or reporter gene.*

11. The process of claim 5, wherein the preselected DNA sequence encoding said endotoxin comprises an increased number of maize preferred codons compared to native *Bacillus thuringiensis* endotoxin.

12. The process of claim 1 or 5, wherein the fertile transgenic *Zea mays* plant is generated from transformed embryogenic tissue.

13. The process of claim 12, wherein the cells are derived from immature embryos.

14. The process of claim 1 or 5, further comprising obtaining transgenic insect resistant progeny plants of subsequent generations from said fertile transgenic plant.

15. The process of claim 14, further comprising obtaining seed from one of said progeny plants.

16. The process of claim 1 or 5, wherein the preselected DNA sequence encodes the HD73 endotoxin of *Bacillus thuringiensis.*

17. The process of claim 16, wherein the preselected DNA sequence encoding said endotoxin comprises an increased number of maize preferred codons compared to native *Bacillus thuringiensis* endotoxin.

18. The process of claim 1 or 5, wherein the preselected DNA sequence encodes the HD1 endotoxin of *Bacillus thuringiensis.*

19. The process of claim 18, wherein the preselected DNA sequence encoding said endotoxin comprises an increased number of maize preferred codons compared to native *Bacillus thuringiensis* endotoxin.

20. The process of claim 1 or 5, wherein the preselected DNA sequence encodes a truncated endotoxin of *Bacillus thuringiensis.*

21. The process of claim 20, wherein the *Bacillus thuringiensis* endotoxin comprises about the N-terminal 50% of the endotoxin.

22. The process of claim 1 or 5, wherein the preselected DNA sequence comprises an operably linked promoter.

23. The process of claim 5, wherein the preselected DNA sequence further comprises a promoter operably linked to said DNA sequence encoding said endotoxin and a promoter operably linked to said selectable marker gene.

24. The process of claim 22, wherein the preselected DNA sequence further comprises the maize AdhIS first intron or the maize Shrunken-2 first intron positioned between the promoter and the preselected DNA sequence encoding said endotoxin.

25. The process of claim 22, wherein the preselected DNA sequence further comprises a manopine synthase promoter, a nopaline synthase promoter or an octopine synthase promoter operably linked to said preselected DNA sequence.

26. The process of claim 22, wherein the promoter is the CaMV 35S or 19S promoter.

* * * * *